(12) United States Patent
Pereira et al.

(10) Patent No.: US 9,399,675 B2
(45) Date of Patent: *Jul. 26, 2016

(54) METHODS AND COMPOSITIONS FOR DIAGNOSING ALZHEIMER'S DISEASE AND AGE-RELATED MACULAR DEGENERATION

(71) Applicant: The Board of Regents of the University of Oklahoma, Norman, OK (US)

(72) Inventors: Heloise Anne Pereira, Edmond, OK (US); Melva L. Gonzalez, St. Charles, MO (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/835,566

(22) Filed: Mar. 15, 2013

(65) Prior Publication Data
US 2013/0195761 A1 Aug. 1, 2013

Related U.S. Application Data

(63) Continuation-in-part of application No. 12/904,917, filed on Oct. 14, 2010, now Pat. No. 8,450,071, which is a continuation-in-part of application No. 12/697,906, filed on Feb. 1, 2010, now abandoned, which is a continuation of application No. 11/712,028, filed on Feb. 28, 2007, now Pat. No. 7,655,480.

(51) Int. Cl.
  *G01N 33/53* (2006.01)
  *C07K 16/18* (2006.01)
  *G01N 33/68* (2006.01)

(52) U.S. Cl.
  CPC ............ *C07K 16/18* (2013.01); *G01N 33/6893* (2013.01); *G01N 33/6896* (2013.01); *G01N 2333/52* (2013.01); *G01N 2800/2821* (2013.01)

(58) Field of Classification Search
  None
  See application file for complete search history.

(56) References Cited

U.S. PATENT DOCUMENTS

| | | | |
|---|---|---|---|
| 7,655,480 B2 | 2/2010 | Pereira | |
| 8,450,071 B2 | 5/2013 | Pereira | |
| 2003/0139353 A1 | 7/2003 | Jackson et al. | |
| 2003/0157580 A1 | 8/2003 | Hochstrasser et al. | |
| 2003/0158083 A1 | 8/2003 | Peters | |
| 2007/0166768 A1 | 7/2007 | Pereira | |

(Continued)

FOREIGN PATENT DOCUMENTS

| | | |
|---|---|---|
| EP | 11833477 | 2/2014 |
| WO | WO 03/076459 A1 | 9/2003 |
| WO | PCT/US2011/056331 | 2/2012 |

OTHER PUBLICATIONS

Akiyama H. et al.: Inflammation and Alzheimer's disease. Neurobiol of Aging (Jan. 17, 2000), vol. 21, pp. 383-421.

(Continued)

*Primary Examiner* — Gregory S Emch
*Assistant Examiner* — Aurora M Fontainhas
(74) *Attorney, Agent, or Firm* — Dunlap Codding, P.C.

(57) ABSTRACT

Compositions comprising monoclonal antibodies raised against CAP37 (Cationic Antimicrobial Protein of Mr 37 kDa) and isoforms thereof, along with antigen binding fragments thereof, are disclosed. The antibodies are used in the diagnosis and early detection of Alzheimer's disease and Age-Related Macular Degeneration.

9 Claims, 27 Drawing Sheets
(20 of 27 Drawing Sheet(s) Filed in Color)

A

B

(56) References Cited

U.S. PATENT DOCUMENTS

2010/0136574 A1    6/2010    Pereira
2011/0250623 A1    10/2011    Pereira

OTHER PUBLICATIONS

Beran et al., "Heparin-binding protein as a biomarker of circulatory failure during sever infections: A report of three cases" *Scandinavian Journal of Infectious Diseases* (2010) vol. 42, pp. 634-636.

Berkestedt et al., "Elevated plasma Levels of Antimicrobial Polypeptides in Patients with Severe Sepsis" *J. Innate Immun.* (2010) vol. 2, pp. 478-482.

Brackett D.J. et al.: A synthetic lipopolysaccharide-binding peptide based on the neutrophil-derived protein CAP37 prevents endotoxin-induced responses in conscious rats. Infect Immun (1997), vol. 65, pp. 2803-2811.

Changho et al., "Neutrophils in biliary atresia. A study on their morphologic distribution and expression of CAP37" *Pathology-Research and Practice* (2010) vol. 206, pp. 314-317.

Chomczynski P. et al.: Single-step method of RNA isolation by acid guanidinium thiocyanate-phenol-chloroform extraction. Anal Biochem (1987), vol. 162, pp. 156-159.

Corpet F.: Multiple sequence alignment with hierarchical clustering. Nucl Acids Res (1988), vol. 16, pp. 10881-10890.

Diglio C.A. et al.: Angiogenesis in rat aorta ring explant cultures. Lab Invest (1989), vol. 60, pp. 523-531.

☐—☐EQ Chapter \h \r 1Enk C.D. et al: UVB induces IL-12 transcription in human keratinocytes in vivo and in vitro. Photochem Photobio (1996), vol.

Flodgaard H. et al.: Covalent structure of two novel neutrophile leucocyte-derived proteins of porcine and human origin: neutrophil elastase homologues with strong monocyte and fibroblast chemotactic activities. Eur J Biochem (1991), vol. 197, pp. 535-547.

Gautam N. et al.: Heparin-binding protein (HBP/CAP37): A missing link in neutrophil-evoked alteration of vascular permeability. Nat Med (2001), vol. 7, pp. 1123-1127.

Gräbner R. et al.: Flow cytometric determination of E-selectin, vascular cell adhesion molecule-1, and intercellular cell adhesion molecule-1 in formaldehyde-fixed endothelial monolayers. Cytometry (2000), vol. 40, pp. 238-244.

Grammas P.: A damaged microcirculation contributes to neuronal cell death in Alzheimer's disease. Neurobiol Aging (2000), vol. 21, pp. 199-205.

Heinzelmann M. et al.: Endocytosis of heparin-binding protein (CAP37) is essential for the enhancement of lipopolysaccharide-induced TNF-α production in human momocytes. J Immunol (1999), vol. 162, pp. 4240-4245.

Heinzelmann M. et al.: Heparin-binding protein (CAP37) is internalized in monocytes and increases LPS-induced monocyte activation. J Immunol (1998), vol. 160, pp. 5530-5536.

Jaffe A.E. et al.: Culture of human endothelial cells derived from umbilical veins. J Clin Invest (1973), vol. 52, pp. 2745-2756.

Kahn et al.: Contact-system activation in children with vasculitis, The Lancet, vol. 360 (Aug. 17, 2002), pp. 535-541.

Lee et al.: Demonstration of CAP37, a monocyte chemoattractant in endothelial cells, FASEB Journal (Mar. 7, 2001), vol. 15, No. 4, pp. A393.

Lee T.D. et al.: CAP37, a Novel Inflammatory Mediator Its Expression in Endothelial Cells and Localization to Atherosclerotic Lesions. American Journal of Pathology, vol. 160, No. 3, (Mar. 2002), pp. 841-848.

Linder et al. "Heparin-binding protein: A diagnostic marker of acute bacterial meningitis" *PubMed* (Dec. 31, 2010) Abstract (1 page).

Linder et al., "Heparin-Binding Protein: An Early Marker of Circulatory Failure in Sepsis" *Major Article* (Oct. 1, 2009) vol. 49, pp. 1044-1050.

Linder et al., "Roles of Heparin-Binding Protein in Bacterial Infections" *J. Innate Immun.* (2010) pp. 1-8.

Lonnemann G. et al.: Differences in the synthesis and kinetics of release of interleukin 1 alpha, interleukin 1 beta and tumor necrosis factor from human mononuclear cells. Eur J Immunol (1989), vol. 19, pp. 1531-1536.

Morgan J.G. et al.: Cloning of the cDNA for the serine protease homolog CAP37/Azurocidin, a microbicidal and chemotactic protein from human granulocytes. J Immunol (1991), vol. 147, pp. 3210-3214.

McGeer et al., "Activation of the classical complement pathway in brain tissue of Alzheimer patients", Neuroscience Letters, vol. 107 (May 17, 1989) pp. 341-346.

McGeer et al., "Inflammation in the Brain in Alzheimer's Disease:Implications for Therapy", Neuroscience News, vol. 1, No. 2, (No Month, 1998) pp. 29-35.

Olczak et al., "Structural analysis of N-glycans from human neutrophil azurocidin." Biochem. Biophys. Res. Comm. Apr. 26, 2002, No. 293, No. 1, pp. 213-219.

Olofsson A.M. et al.: Heparin-binding protein targeted to mitochondrial compartments protects endothelial cells from apoptosis. J Clin Invest (1999), vol. 104, pp. 885-894.

Østergaard E. et al.: A neutrophil-derived proteolytic inactive elastase homologue (hHBP) mediates reversible contraction of fibroblasts and endothelial cell monolayers and stimulates monocyte survival and thrombospondin secretion. J Leukoc Biol (1992), vol. 51, pp. 316-323.

Pereira H.A. et al.: CAP37, a 37kD human neutrophil granule cationic protein shares homology with inflammatory proteinases. Life Sciences (1990), vol. 46, pp. 189-196.

Pereira H.A.: Cationic Antimicrobial proteing of Mr 37 kDa: a multifunctional inflammatory protein. Chines Medical Journal (2001), vol. 114(I), pp. 9-13.

Pereira H.A, et al.: CAP37, a human neutrophil-derived chemotactic factor with monocyte specific activity. J Clin Invest (1990), vol. 85, pp. 1468-1476.

Pereira H.A. et al.: CAP37, a neutrophil granule-derived protein stimulates protein kinase C activity in endothelial cells. J Leukoc Biol (1996), vol. 60, pp. 415-422.

Pereira H.A. et al.: Expression of CAP37, a novel inflammatory mediator, in Alzheimer's disease. Neurobiol Aging (1996), vol. 17, pp. 753-759.

Pereira H.A. et al.: Synthetic bactericidal peptide based on CAP37: a 37-kDa human neutrophil granule-associated cationic antimicrobial protein chemotactic for monocytes. Proc Natl Acad Sci (USA) (1993), vol. 90, pp. 4733-4737.

Pereira H.A.. et al.: Quantitation of a cationic antimicrobial granule protein of human polymorphonuclear leukocyts by ELISA. J. Immunol. Meth., (1989), vol. 117, pp. 115-120.

Pereira et al., "CAP37, an inflammatory mediator in Alzheimer's disease", The FASEB Journal, vol. 22, No. 1, 67.11 (2008) (abstract).

Pereira et al., Novel isoform of CAP37 Expressed in Endothelial Cells and Localized to Atherosclerotic Lessions, Office of Technology Development, The University of Oklahoma, Oct. 2011, (abstract only).

Pohl J.. et al.: Amino acid sequence of CAP37, a human neutrophil granule-derived antibacterial and monocyte-specific chemotactic glycoprotein structurally similar to neutrophil elastase. FEBS Letters (1990), vol. 272, pp. 200-204.

Rasmussen P.B. et al.: Characterization of recombinant human HBP/CAP37/azurocidin, a pleiotropic mediator of inflammation-enhancing LPS-induced cytokine release from monocytes. FEBS letters (1996), vol. 390, pp. 109-112.

Reining et al.: Cap37 During Cardiopulmonary Bypass, Increase in Plasma Levels Upon Heparin and LMWH, Abstracts of the 16th Annual Congress of the ESICM, Poster Session, Acute Lung Injury, Amsterdam, Netherlands 5-8 (Oct. 2003), p. S87.

Ross R.: Atherosclerosis—an inflammatory disease. N Engl J Med (1999), vol. 340, pp. 115-126.

Sears P. et al.: Enzyme action in glycoprotein synthesis. Cell Mol Life Sci (1998), vol. 54, pp. 223-252.

Shafer W.M. et al.: Cationic antimicrobial proteins isolated from human neutrophil granulocytes in the presence of diisopropyl fluorophosphate. Infect Immun (1984), vol. 45, pp. 29-35.

(56) References Cited

OTHER PUBLICATIONS

Shafer W.M. et al.: Late intraphagosomal hydrogen ion concentration favors the in vitro antimicrobial capacity of a 37-kilodalton cationic granule protein of human neutrophil granules. Infect Immun (1986), vol. 53, pp. 651-655.
Strongin: Laboratory Diagnosis of Viral Invections, Sensitivity, Specificity, and Predictive Value of Diagnostic Tests: Definintions and Clinical Applicatins, Lennette, ed. Marcel Dekker, Inc. New York (1992), pp. 211-219.
Tapper et al.: Secretion of heparin-binding protein from human neutrophils is determined by its localization in azurophilic granules and secretory vesicles, Blood, (Mar. 1, 2002), vol. 99, No. 5, pp. 1785-1793.
Walter M.J. et al.: Interleukin 12 p40 production by barrier epithelial cells during airway inflammation. J Exp Med (2001), vol. 193, pp. 339-351.
Pereira, "Early Detection Marker for Chronic Inflammatory Associated Disease" U.S. Appl. No. 10/384,474, filed Mar. 7, 2003, Office Action Election/Restriction, mailed Jan. 26, 2006, 5 pgs.
Pereira, "Early Detection Marker for Chronic Inflammatory Associated Disease" U.S. Appl. No. 10/384,474, filed Mar. 7, 2003, Response to Election Requirement, mailed Feb. 7, 2006, 5 pgs.
Pereira, "Early Detection Marker for Chronic Inflammatory Associated Disease" U.S. Appl. No. 10/384,474, filed Mar. 7, 2003, Office Action, mailed Apr. 18, 2006, 13 pgs.
Pereira, "Early Detection Marker for Chronic Inflammatory Associated Disease" U.S. Appl. No. 10/384,474, filed Mar. 7, 2003, Amendment and Response, mailed Jun. 5, 2006, 11 pgs.
Pereira, "Early Detection Marker for Chronic Inflammatory Associated Disease" U.S. Appl. No. 10/384,474, filed Mar. 7, 2003, Office Action, mailed Aug. 28, 2006, 10 pgs.
Pereira, "Early Detection Marker for Chronic Inflammatory Associated Disease" U.S. Appl. No. 10/384,474, filed Mar. 7, 2003, Express Abandonment, mailed Feb. 28, 2007.
Pereira, "Method for Predicting Sepsis or an Acute Infectious Inflammatory Response" U.S. Appl. No. 11/712,028, filed Feb. 28, 2007, Office Action Election/Restriction, mailed Oct. 31, 2007, 6 pgs.
Pereira, "Method for Predicting Sepsis or an Acute Infectious Inflammatory Response" U.S. Appl. No. 11/712,028, filed Feb. 28, 2007, Response to Restriction Requirement, mailed Nov. 15, 2007, 2 pgs.
Pereira, "Method for Predicting Sepsis or an Acute Infectious Inflammatory Response" U.S. Appl. No. 11/712,028, filed Feb. 28, 2007, Office Action, mailed Dec. 27, 2007, 6 pgs.
Pereira, "Method for Predicting Sepsis or an Acute Infectious Inflammatory Response" U.S. Appl. No. 11/712,028, filed Feb. 28, 2007, Amendment, mailed Mar. 26, 2008, 5 pgs.
Pereira, "Method for Predicting Sepsis or an Acute Infectious Inflammatory Response" U.S. Appl. No. 11/712,028, filed Feb. 28, 2007, Final Office Action, mailed Jun. 23, 2008, 7 pgs.
Pereira, "Method for Predicting Sepsis or an Acute Infectious Inflammatory Response" U.S. Appl. No. 11/712,028, filed Feb. 28, 2007, Request for Continued Examination and Amendment and Response, mailed Nov. 10, 2008, 11 pgs.
Pereira, "Method for Predicting Sepsis or an Acute Infectious Inflammatory Response" U.S. Appl. No. 11/712,028, filed Feb. 28, 2007, Office Action, mailed Dec. 15, 2008, 10 pgs.
Pereira, "Method for Predicting Sepsis or an Acute Infectious Inflammatory Response" U.S. Appl. No. 11/712,028, filed Feb. 28, 2007, Amendment and Response, mailed Jun. 10, 2009, 9 pgs.
Pereira, "Method for Predicting Sepsis or an Acute Infectious Inflammatory Response" U.S. Appl. No. 11/712,028, filed Feb. 28, 2007, Declaration of H. Anne Pereira, Ph.D. Under 37 CFR 1.132, mailed Jun. 10, 2009 6 pgs.
Pereira, "Method for Predicting Sepsis or an Acute Infectious Inflammatory Response" U.S. Appl. No. 11/712,028, filed Feb. 28, 2007, Office Action, mailed Dec. 27, 2007, 9 pgs.
Pereira, "Method for Predicting Sepsis or an Acute Infectious Inflammatory Response" U.S. Appl. No. 11/712,028, filed Feb. 28, 2007, Office Action, mailed Jun. 23, 2008, 7 pgs.
Pereira, "Method for Predicting Sepsis or an Acute Infectious Inflammatory Response" U.S. Appl. No. 11/712,028, filed Feb. 28, 2007, Request for Continued Examination and Amendment, mailed Nov. 10, 2008, 11 pgs.
Pereira, "Method for Predicting Sepsis or an Acute Infectious Inflammatory Response" U.S. Appl. No. 11/712,028, filed Feb. 28, 2007, Office Action, mailed Dec. 15, 2008, 11 pgs.
Pereira, "Method for Predicting Sepsis or an Acute Infectious Inflammatory Response" U.S. Appl. No. 11/712,028, filed Feb. 28, 2007, Amendment, mailed Jun. 10, 2009, 15 pgs.
Pereira, "Method for Predicting Sepsis or an Acute Infectious Inflammatory Response" U.S. Appl. No. 11/712,028, filed Feb. 28, 2007, Notice of Allowability, mailed Aug. 28, 2009, 4 pgs.
Pereira, "Method for Predicting Sepsis or an Acute Infectious Inflammatory Response" U.S. Appl. No. 11/712,028, filed Feb. 28, 2007, Response to Interview Summary, mailed Sep. 22, 2009, 2 pgs.
Pereira, "Method for Detecting a Chronic Inflammatory-Associated Disease" U.S. Appl. No. 12/697,906, filed Feb. 1, 2010, Office Action, mailed Apr. 14, 2010, 20 pgs.
Pereira, "Method for Detecting a Chronic Inflammatory-Associated Disease" U.S. Appl. No. 12/697,906, filed Feb. 1, 2010, Express Abandonment, mailed Oct. 14, 2010.
Pereira, et al., "Expression of CAP37, a Novel Inflammatory Mediator, in Alzheimer's Disease" Neurobiology of Aging, vol. 17, No. 5, (Jan. 1, 1996) pp. 753-759.

METHODS AND COMPOSITIONS FOR DIAGNOSING ALZHEIMER'S DISEASE AND AGE-RELATED MACULAR DEGENERATION

CROSS REFERENCE TO RELATED APPLICATIONS/INCORPORATION BY REFERENCE STATEMENT

This application is a continuation-in-part of U.S. Ser. No. 12/904,917, filed Oct. 14, 2010, which is a continuation-in-part of U.S. Ser. No. 12/697,906, filed Feb. 1, 2010, now abandoned, which is a continuation of U.S. Ser. No. 11/712,028, filed Feb. 28, 2007, now U.S. Pat. No. 7,655,480. Each of the above-referenced patents and patent applications is hereby expressly incorporated herein by reference in its entirety.

STATEMENT REGARDING FEDERALLY SPONSORED RESEARCH OR DEVELOPMENT

This invention was made with Government support under Public Health Service Grant AI-28018-06 awarded by National Institute of Allergy and Infectious Disease and under Grant EY15534 awarded by the National Eye Institute. The Government has certain rights in the invention.

BACKGROUND

The presently disclosed inventive concept(s) relates to, but is not limited to, anti-CAP37 antibodies, isoforms of CAP37, methods for detecting chronic and acute inflammatory-associated diseases, and methods of treatment using the anti-CAP37 antibodies.

Cationic Antimicrobial Protein of $M_r$ 37 kDa (CAP37) was originally isolated from granule extracts of human polymorphonuclear leukocytes (PMN) in 1984 (1). The amino acid sequence of PMN-CAP37 revealed its relation to members of the serine protease family that have a conserved catalytic active site consisting of his-57, asp-102 and ser-195 in the charge relay system (2). Of these sites, the conserved histidine and serine of the catalytic triad have been replaced with serine and glycine residues, respectively, rendering CAP37 ineffective as a serine protease (2,3). However, CAP37 has been demonstrated to have a diverse and exciting repertoire of functions. It was first analyzed regarding its bactericidal properties against Gram negative bacteria including, but not limited to, *Salmonella typhimurium, Escherichia coli* and *Pseudomonas aeruginosa* (4) and its ability to bind to and neutralize lipopolysaccharide (LPS)(5). Subsequently CAP37 was shown to be a potent chemoattractant for monocytes (6). Additionally, regarding its effects on the monocyte, CAP37 has been reported to stimulate their survival and thrombospondin secretion (7), also to enhance the LPS-stimulated release of prostaglandin E2 (8), interleukin 6 (IL-6)(9) and tumor necrosis factor-alpha (TNFα)(8-10). To add even further to its extensive range of known functions, CAP37 has been demonstrated to stimulate the reversible contraction of fibroblasts and endothelial cells (7) and to activate endothelial cell protein kinase C(PKC)(11). Recently, CAP37 released from stimulated PMN was reported to be taken up and sequestered in nearby endothelial mitochondria and has been suggested to protect against apoptosis (12).

The presence of CAP37 in the endothelium of Alzheimer's brain microvessels has been shown to be induced in rat brain endothelial cells in response to stimulation with the inflammatory molecules TNFα, interleukin 1-alpha (IL-1α) and LPS (13). There is also evidence that both Alzheimer's disease (AD) and atherosclerosis are inflammatory-associated (modulated) diseases (14, 15) in which inflammation and associated mediators can exacerbate or augment the disease.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
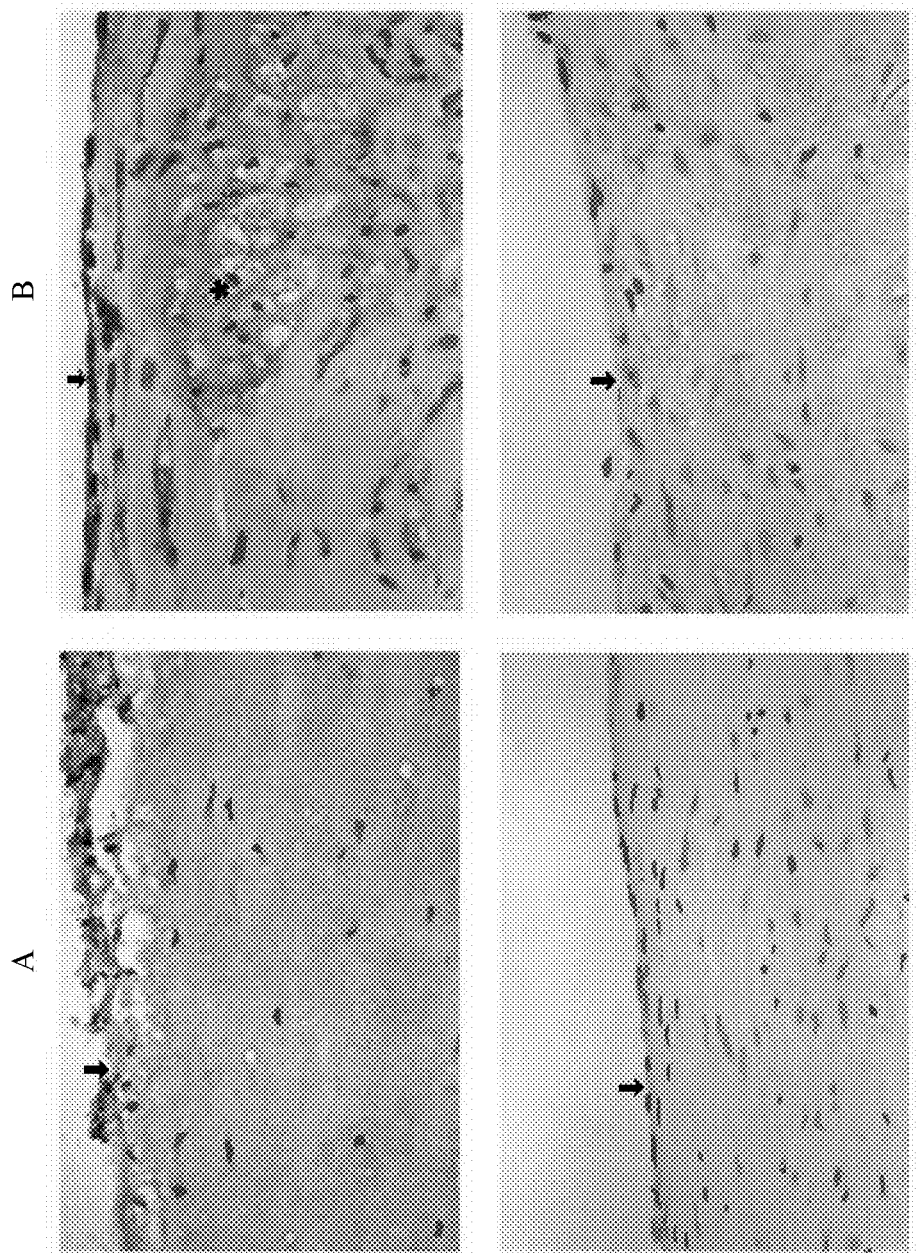
FIG. 1: Localization of CAP37 in formalin-fixed, paraffin embedded carotid artery. A: Immunohistochemistry performed on atherosclerotic lesion present in the carotid artery using antisera to human CAP37 and the VECTASTAIN ELITE technique as described elsewhere herein. Strong staining indicated the presence of CAP37 in the endothelium (×400). B: Detection of CAP37 in advanced atherosclerotic plaque indicating strong positive staining in endothelium and foam cells (×400). C: Normal vessel stained with antisera to CAP37 indicating an absence of CAP37 in "normal" endothelium (×400). D: Atherosclerotic lesion stained using an immunoadsorbed antisera to CAP37 which shows no staining (×400). The lack of staining in D indicates the specificity of the antisera for CAP37 used in these assays. Sections were counterstained with hematoxylin. ↓ indicates endothelium; * indicates foam cell.

Before explaining at least one embodiment of the presently disclosed inventive concept(s) in more detail by way of exemplary description, examples, and results, it is to be understood that the presently disclosed inventive concept(s) is not limited in its application to the details of methods and compositions as set forth in the following description. The presently disclosed inventive concept(s) is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concept(s) may be practiced without these specific details. In other instances features which are well known to persons of ordinary skill in the art have not been described in detail to avoid unnecessary complication of the description.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which the presently disclosed and claimed inventive concept(s) pertains. All publications and patent applications are herein incorporated by reference to the same extent as if each individual publication or patent application was specifically and individually indicated to be incorporated by reference.

All of the compositions and/or methods disclosed and claimed herein can be made and/or executed without undue experimentation in light of the present disclosure. While the compositions and methods of the presently disclosed and claimed inventive concept(s) have been described in terms of particular embodiments, it will be apparent to those of skill in the art that variations may be applied to the compositions and/or methods and in the steps or in the sequence of steps of the method described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The terms "peptide", "polypeptide" and "protein" are used herein to refer to a polymer of amino acid residues. The term "polypeptide" as used herein is a generic term to refer to native protein, protein fragments, or analogs of a polypeptide sequence. Hence, native protein, protein fragments, and analogs are species of the polypeptide genus. The term "isolated peptide/polypeptide/protein" as used herein refers to a peptide/polypeptide/protein of cDNA, recombinant RNA, or synthetic origin or some combination thereof, which by virtue of its origin, or source of derivation, the "isolated peptide/polypeptide/protein": (1) is not associated with peptides/polypeptides/proteins found in nature, (2) is substantially free of other peptides/polypeptides/proteins from the same source, e.g., free of murine proteins, (3) is expressed by a cell from a different species, and/or (4) does not occur in nature.

As used herein, the term "amino acid" embraces all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The terms "polynucleotide", and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The terms "isolated nucleic acid" and "isolated polynucleotide" are used interchangeably; a nucleic acid or polynucleotide is considered "isolated" if it: (1) is not associated with all or a portion of a polynucleotide in which the "isolated polynucleotide" is found in nature, (2) is linked to a polynucleotide to which it is not linked in nature, or (3) does not occur in nature as part of a larger sequence.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

The term "naturally-occurring" as used herein as applied to an object refers to the fact that an object can be found in nature. For example, a polynucleotide or polypeptide sequence that is present in an organism (including viruses) that can be isolated from a source in nature and which has not been intentionally modified by man in the laboratory or otherwise is naturally-occurring. The term "naturally-occurring" may be used interchangeably herein with the term "native".

The term "selectively hybridize" referred to herein means to detectably and specifically bind. Polynucleotides, oligonucleotides and fragments thereof encoding peptides/polypeptides/proteins in accordance with the inventive concept(s) selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the inventive concept(s) and a nucleic acid sequence of interest will be at least 80%, and more typically with increasing homologies of at least 85%, or at least 90%, or at least 91%, or at least 92%, or at least 93%, or at least 94%, or at least 95%, or at least 96%, or at least 97%, or at least 98%, or at least 99%, or 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; particular gap lengths are lengths of 5 or less or 2 or less. Alternatively and typically, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more particularly homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Adv. Appl. Math., 2:482 (1981)), by the homology alignment algorithm of Needleman and Wunsch (J. Mol. Biol., 48:443 (1970)), by the search for similarity method of Pearson and Lipman (Proc. Natl. Acad. Sci. (U.S.A.), 85:2444 (1988)), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages, or by inspection, and the best alignment (i.e., resulting in the highest percentage of homology over the comparison window) generated by the various methods is selected.

The term "sequence identity" means that two polynucleotide or amino acid sequences is identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity.

The term "substantial identity" as used herein denotes a characteristic of a polynucleotide or amino acid sequence, wherein the polynucleotide or amino acid comprises a sequence that has at least 80 percent sequence identity, such as at least 85%, or at least 90%, or at least 91%, or at least 92%, or at least 93%, or at least 94%, or at least 95%, or at least 96%, or at least 97%, or at least 98%, or at least 99%, or 100% sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disbustituted amino acids, N-alkyl amino acids, lactic acid, and other unconventional amino acids may also be suitable components for polypeptides of the presently disclosed and claimed inventive concept(s). Examples of unconventional amino acids include: 4-hydroxyproline, α-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, such as at least 85%, or at least 90%, or at least 91%, or at least 92%, or at least 93%, or at least 94%, or at least 95%, or at least 96%, or at least 97%, or at least 98%, or at least 99%, or 100% sequence identity. Particularly, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Particular conservative amino acids substitution groups are: valine-leucine-isoleucine, phenylalanine-tyrosine, lysine-arginine, alanine-valine, glutamic-aspartic, and asparagine-glutamine.

The term "variant" of a reference polypeptide refers to a polypeptide having one or more amino acid substitutions, deletions or insertions relative to the reference polypeptide. An amino acid substitution may be "conservative" or "non-conservative". A "conservative" amino acid substitution refers to the substitution of an amino acid in a polypeptide with another amino acid having similar properties, such as but not limited to, size and charge. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More particular families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art as explained in further detail below. Particular amino- and carboxy-termini of fragments or analogs occur near boundaries of functional domains. Structural and functional domains can be identified by comparison of the nucleotide and/or amino acid sequence data to public or proprietary sequence databases. Particularly, computerized comparison methods are used to identify sequence motifs or predicted protein conformation domains that occur in other proteins of known structure and/or function. Methods to identify protein sequences that fold into a known three-dimensional structure are known (Bowie et al., Science, 253:164 (1991)). Thus, the foregoing examples demonstrate that those of skill in the art can recognize sequence motifs and structural conformations that may be used to define structural and functional domains in accordance with the presently disclosed and claimed inventive concept(s).

Particular amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (particularly conservative amino acid substitutions) may be made in the naturally-occurring sequence (particularly in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure© (Branden and J. Tooze, eds., Garland Publishing, New York, N.Y. (1991)); and Thornton et al. (Nature 354:105 (1991)), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence. A polypeptide fragment may be any length that is less than the length of the reference polypeptide.

The term "antibody" is used in the broadest sense, and specifically covers monoclonal antibodies (including full length monoclonal antibodies), polyclonal antibodies, multi-specific antibodies (e.g., bispecific antibodies), and antibody fragments so long as they exhibit the desired biological activity. Thus, the terms "Antibody" or "antibody peptide(s)" refer to a full length immunoglobulin molecule (i.e., an intact antibody), or a binding fragment thereof that competes with the intact antibody for specific antigen binding. Binding fragments may be produced by recombinant DNA techniques, or by enzymatic or chemical cleavage of intact antibodies. Binding fragments include Fab, Fab', F(ab')$_2$, Fv, scFv, disulfide linked Fv, Fd, diabodies, single-chain antibodies, single domain antibodies (such as but not limited to, NANOBODIES®) and other antibody fragments that retain at least a portion of the variable region of an intact antibody. See, e.g., Hudson et al. (Nature Med., 9:129-134 (2003)).

The term "antigen-binding fragment" or "antigen-binding portion" of an antibody, as used herein, refers to one or more fragments of an antibody that retain the ability to bind to the antigen of interest, in this case a form of CAP37. The antigen-binding function of an antibody can be performed by fragments of an intact antibody. Examples of binding fragments encompassed within the term "antigen-binding fragment" of an antibody include but are not limited to, Fab, Fab', F(ab')2, Fv, scFv, disulfide linked Fv, Fd, diabodies, single-chain antibodies, single domain antibodies (such as but not limited to, NANOBODIES®), isolated CDRH3, and other antibody fragments that retain at least a portion of the variable region of an intact antibody. These antibody fragments are obtained using conventional recombinant and/or enzymatic techniques and are screened for antigen binding in the same manner as intact antibodies.

The terms "CDR", and its plural "CDRs", refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

The term "epitope" includes any protein determinant capable of specific binding to an immunoglobulin or T-cell receptor. In certain embodiments, an epitope is a region of an antigen that is specifically bound by an antibody. Epitopic determinants usually include chemically active surface groupings of molecules such as amino acids, sugar side chains, phosphoryl, or sulfonyl groups. In certain embodiments, an epitope may have specific three dimensional structural characteristics (e.g., a "conformational epitope"), as well as specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope or closely related epitopes. In certain instances, for example, homologous proteins from different species may comprise the same epitope. In certain embodiments, an antibody specifically binds to an antigen with a dissociation constant of no greater than $10^{-6}$ M, $10^{-7}$ M, $10^{-8}$ M or $10^{-9}$ M.

When an antibody specifically binds to a receptor or ligand (i.e. counterreceptor), it may substantially inhibit adhesion of the receptor to the ligand. As used herein, an antibody substantially inhibits adhesion of a receptor to a ligand when an excess of antibody reduces the quantity of receptor bound to ligand by at least about 20%, 40%, 60% or 80%, 85% or 90% (as measured in an in vitro competitive binding assay).

An "isolated" antibody is one which has been separated and/or recovered from a component of the environment in which it was produced. Contaminant components of its production environment are materials which would interfere with diagnostic or therapeutic uses for the antibody, and may include enzymes, hormones, and other proteinaceous or non-proteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spinning cup sequenator, such as at least 15 residues of sequence; or 3) to homogeneity by SDS-PAGE under reducing or non-reducing conditions using Coomasie blue or silver stain. Isolated antibody includes the antibody in situ within recombinant cells since at least one component of the environment in which the antibody is produced will not be present. Ordinarily, however, isolated antibody will be prepared by at least one purification step. In addition, the "isolated antibody" is substantially free of other antibodies having different antigenic specificities. An isolated antibody may, however, have some cross-reactivity to other, related antigens.

The term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or such as at least 85%, or at least 90%, or at least 91%, or at least 92%, or at least 93%, or at least 94%, or at least 95%, or at least 96%, or at least 97%, or at least 98%, or at least 99% sequence identity.

The term "monoclonal antibody" as used herein refers to an antibody obtained from a population of substantially homogeneous antibodies that specifically bind to the same epitope, i.e., the individual antibodies comprising the population are identical except for possible naturally occurring mutations that may be present in minor amounts. In contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that in one method of production they may be synthesized by a hybridoma culture, and thus are uncontaminated by other immunoglobulins. The modifier "monoclonal" indicates the character of the antibody as being obtained from a substantially homogeneous population of antibodies, and is not to be construed as requiring production of the antibody by any particular method. For example, in one embodiment, the monoclonal antibodies produced in accordance with the presently disclosed and claimed inventive concept(s) may be made by the hybridoma method first described by Kohler and Milstein (Nature, 256:495 (1975)).

The monoclonal antibodies utilized in accordance with the presently disclosed and claimed inventive concept(s) may be produced by any methodology known in the art including, but not limited to, a result of a deliberate immunization protocol; a result of an immune response that results in the production of antibodies naturally in the course of a disease or cancer; phage-derived antibodies; and the like. In addition to the hybridoma production method listed above, the monoclonal antibodies of the presently disclosed and claimed inventive concept(s) may be produced by other various methods such as, but not limited to, recombinant DNA methods (see, e.g., U.S. Pat. No. 4,816,567); isolation of antibody fragments from a phage display library (see, e.g., Clackson et al., Nature, 352: 624-628 (1991); and Marks et al., J. Mol. Biol., 222:581-597 (1991)); as well as various other monoclonal antibody production techniques (see, e.g., Harlow and Lane (1988) Antibodies: A Laboratory Manual (Cold Spring Harbor Laboratory, Cold Spring Harbor, N.Y.)).

Once the antibodies have been obtained, for example once individual B cells have been identified and/or monoclonal antibodies have been produced, the sequences encoding the variable regions of these antibodies can be obtained. The variable region sequences can for example be obtained by first sequencing the antibody protein produced by the hybridoma, B-cell or phage and determining the encoding nucleic acid sequence. In one embodiment, the immunoglobulin variable region (VH and VL) DNA or cDNA may be sequenced instead. Where the antibody is derived from a hybridoma cell line or isolated B-cell, the cDNAs encoding the variable regions may be amplified using PCR by for example the methods described in Babcook et al. (Proc. Natl. Acad. Sci.

USA, 93:7843-7848 (1996)), and in PCT Publication No. WO 92/02551. The contents of both references are expressly incorporated herein by reference in their entirety.

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from one animal fused to a portion of an antibody from a second animal. For example but not by way of limitation, a chimeric antibody may comprise all or portion of a variable region of an antibody derived from a non-human animal fused to a constant region of an antibody derived from a human.

Utilization of the monoclonal antibodies of the presently disclosed and claimed inventive concept(s) may require administration thereof to a subject, such as but not limited to, a human. However, when the monoclonal antibodies are produced in a non-human animal, such as a rodent, administration of such antibodies to a human patient will normally elicit an immune response, wherein the immune response is directed towards the sequence of the antibodies. Such reactions limit the duration and effectiveness of such a therapy. In order to overcome such problem, the monoclonal antibodies of the presently disclosed and claimed inventive concept(s) can be "humanized", that is, the antibodies are engineered such that one or more antigenic portions thereof are removed and like portions of a human antibody are substituted therefore, while the antibody's affinity for the desired epitope is retained. This engineering may only involve a few amino acids, or may include entire framework regions of the antibody, leaving only the complementarity determining regions of the antibody intact. Several methods of humanizing antibodies are known in the art and are discussed in further detail below and in U.S. Pat. Nos. 6,180,370; 6,054,927; 5,869,619; 5,861,155; 5,712,120; and 4,816,567, the specifications of which are all hereby expressly incorporated herein by reference in their entirety.

As mentioned above, a "humanized" antibody refers to a non-human antibody that has been modified so that it more closely matches (in amino acid sequence) a human antibody. A humanized antibody is thus a type of chimeric antibody. As described above, antibodies interact with target antigens predominantly through amino acid residues that are located in the heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific, naturally occurring antibodies by constructing expression vectors in which the CDR sequences from the naturally occurring antibody are grafted into framework sequences from a different antibody with different properties, such as human antibody framework regions. Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24:827-836; the contents of each of which are expressly incorporated herein by reference.

Humanized forms of antibodies are chimeric immunoglobulins, immunoglobulin chains or fragments thereof (such as Fv, Fab, Fab', F(ab')$_2$, or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., 1986; Riechmann et al., 1988; Verhoeyen et al., 1988), by substituting rodent CDRs or CDR sequences for the corresponding sequences of a human antibody. (See also U.S. Pat. No. 5,225,539.) In some instances, $F_v$ framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, 1992).

The prior art is replete with descriptions relating to the generation or use of humanized antibodies. Many of these studies teach useful examples of protocols that can be utilized with the presently disclosed and claimed inventive concept(s), such as but not limited to, Sandborn et al., Gatroenterology, 120:1330 (2001); Mihara et al., Clin. Immunol., 98:319 (2001); Yenari et al., Neurol. Res., 23:72 (2001); Morales et al., Nucl. Med. Biol., 27:199 (2000); Richards et al., Cancer Res., 59:2096 (1999); Yenari et al., Exp. Neurol., 153:223 (1998); and Shinkura et al., Anticancer Res., 18:1217 (1998), all of which are expressly incorporated in their entirety by reference. However, it is to be understood that the presently disclosed and claimed inventive concept(s) is not limited to the treatment protocols described above, and other treatment protocols which are known to a person of ordinary skill in the art may be utilized in the methods of the presently disclosed and claimed inventive concept(s).

The presently disclosed and claimed inventive concept(s) further includes the use of fully human monoclonal antibodies. Fully human antibodies essentially relate to antibody molecules in which the entire sequence of both the light chain and the heavy chain, including the CDRs, arise from human genes. Such antibodies are termed "human antibodies" or "fully human antibodies" herein. "Human antibodies" contain human antibody sequences and do not contain antibody sequences from a non-human animal. In certain embodiments, a human antibody may further contain synthetic sequences not found in native antibodies. The term is not limited by the manner in which the antibodies are made.

Human monoclonal antibodies may be prepared by the trioma technique; the human B-cell hybridoma technique (see Kozbor et al., Hybridoma, 2:7 (1983)) and the EBV hybridoma technique to produce human monoclonal antibodies (see Cole et al., PNAS, 82:859 (1985)). Human monoclonal antibodies may be utilized in the practice of the presently disclosed and claimed inventive concept(s) and may be produced by using human hybridomas (see Cote et al. PNAS, 80:2026 (1983)) or by transforming human B-cells with Epstein Barr Virus in vitro (see Cole et al., 1985).

In addition, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example but not by way of limitation, in U.S. Pat. Nos. 5,545,807; 5,545,806; 5,569,825; 5,625,126; 5,633,425; 5,661,016, and in Marks et al., J. Biol. Chem., 267:16007 (1992); Lonberg et al., Nature, 368:856 (1994); Morrison, 1994; Fishwild et al., Nature Biotechnol., 14:845 (1996); Neuberger, Nat. Biotechnol., 14:826 (1996); and Lonberg and Huszar, Int Rev Immunol., 13:65 (1995).

Human antibodies may additionally be produced using transgenic nonhuman animals which are modified so as to produce fully human antibodies rather than the animal's endogenous antibodies in response to challenge by an antigen. (See PCT Publication No. WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. One embodiment of such a nonhuman animal is a mouse, and is termed the XENOMOUSE™ as disclosed in PCT Publication Nos. WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598, issued to Kucherlapati et al. on Aug. 17, 1999, and incorporated herein by reference. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771, issued to Hori et al. on Jun. 29, 1999, and incorporated herein by reference. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "antigen-binding site" refers to a portion of an antibody capable of specifically binding an antigen. In certain embodiments, an antigen-binding site is provided by one or more antibody variable regions.

As used herein, "substantially pure" or "isolated" means an object species is the predominant species present (i.e., on a molar basis it is more abundant than any other individual species in the composition). Generally, a substantially pure composition will comprise at least about 50% percent of all macromolecular species present in the composition, such as at least about 55%, at least about 60%, at least about 65%, at least about 70%, at least about 75%, at least about 80%, at least about 85%, at least about 90%, at least about 95%, or at least about 99%. In one embodiment, the object species is purified or isolated to essential homogeneity (contaminant species cannot be detected in the composition by conventional detection methods) wherein the composition consists essentially of a single macromolecular species.

The term "agent" refers to a chemical compound, a mixture of chemical compounds, a biological macromolecule, or an extract made from biological materials. In certain embodiments, the "agent" may be a monoclonal antibody in accordance with the presently disclosed and claimed inventive concept(s). The term "antagonist" refers to an agent that reduces an activity of a protein/enzyme. The term "agonist" refers to an agent that increases an activity of a protein/enzyme. The term "patient" or "subject" includes both human and veterinary subjects. In certain embodiments, a patient or subject is a mammal. In certain other embodiments, the patient or subject is a human.

"Treatment" refers to both therapeutic treatment and prophylactic or preventative measures. Those in need of treatment include, but are not limited to, individuals already having a particular condition, disease, or disorder as well as individuals who are at risk of acquiring a particular condition, disease, or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect. A "therapeutic antibody" refers to an antibody or binding fragment thereof that may be administered in vivo to bring about a therapeutic and/or prophylactic/preventative effect.

A "disorder" or "disease" is any condition that would benefit from treatment with the polypeptide. This includes chronic and acute disorders or diseases including those pathological conditions which predispose the mammal to the disorder in question.

"Mammal" for purposes of treatment refers to any animal classified as a mammal, including human, domestic and farm animals including horses, cows, sheep, pigs, llamas, goats, nonhuman primates and monkeys, dogs, cats, mice, rats, rabbits, or any other species with mammary tissue.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The therapeutic effect may include, for example but not by way of limitation, inhibiting and/or neutralizing at least one activity of CAP37. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease/disorder in conjunction with the compositions of the presently disclosed and claimed inventive concept(s). This concurrent therapy can be sequential therapy where the patient is treated first with one drug and then the other, or the two drugs are given simultaneously.

The term "pharmaceutically acceptable" refers to compounds and compositions which are suitable for administration to humans and/or animals without undue adverse side effects such as toxicity, irritation and/or allergic response commensurate with a reasonable benefit/risk ratio. As used herein, "pharmaceutically-acceptable carrier" includes any and all solvents, dispersion media, coatings, antibacterial and antifungal agents, isotonic agents, absorption delaying agents, and the like. Pharmaceutically-acceptable carriers are materials, useful for the purpose of administering the compounds in the methods described herein, which are typically non-toxic, and may be solid, liquid, or gaseous materials, which are otherwise inert and pharmaceutically acceptable, and are compatible with the compounds of the presently disclosed and claimed inventive concept(s). Examples of such carriers include oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The compositions of the presently disclosed and claimed inventive concept(s) may be administered to a patient by any suitable method known in the art, including but not limited to, oral, topical, transdermal, parenteral, subcutaneous, intranasal, intramuscular, intraperitoneal, intravitreal and intravenous routes, including both local and systemic applications. In addition, the compounds of the presently disclosed and claimed inventive concept(s) may be designed to provide delayed, controlled or sustained release using formulation techniques which are well known in the art.

Turning now to the presently disclosed and claimed inventive concept(s), compositions comprising novel anti-CAP37 monoclonal antibodies (raised against CAP37 and CAP37 isoforms) are disclosed, as are hybridomas or cells for producing such antibodies. The presently disclosed and claimed inventive concept(s) further includes a method of detecting a chronic inflammatory-associated disease such as Alzheimer's disease in a subject, a therapeutic method of inhibiting CAP37-mediated cellular activities, and a method for determining the success of a therapeutic treatment by determining levels of CAP37 protein in a sample.

In one embodiment, the detection method comprises the steps of: (1) obtaining a fluid sample (such as serum or plasma) from the subject, typically wherein the subject does not have an acute bacterial or viral infection when the fluid sample is obtained, (2) testing the fluid sample for an isoform of CAP37 protein, and (3) concluding that the subject has a chronic inflammatory-associated disease when the isoform of CAP37 protein is detected in the fluid sample. The fluid sample is typically serum, plasma, or cerebrospinal fluid, for example, or any other body fluid exposed to endothelial, vascular, or neuronal secretions. In one embodiment the chronic inflammatory-associated disease is atherosclerosis. In another embodiment, the chronic inflammatory-associated disease is Alzheimer's disease. In another embodiment, the disease is asthma. In yet another embodiment, Age-Related Macular Degeneration can be detected. In another embodiment, the disease is rheumatoid arthritis. In another embodiment, the disease is atherosclerosis, osteoarthritis and/or psoriasis. In other embodiments, the disease may be an inflammatory disease of the bowel, including but not limited to, Irritable Bowel Syndrome (IBS), Inflammatory Bowel Disease (IBD), or Crohn's disease. The isoform of CAP37 protein typically comprises at least a portion of the protein having the amino acid sequence identified herein as SEQ ID NO: 8. In alternate embodiments, the isoforms have molecular weights of about 135 kDa (±15 kDa) or about 100 kDa (±15 kDa) as assessed by SDS PAGE under reducing conditions.

In another embodiment, the presently disclosed and claimed inventive concept(s) comprises a method of predicting the occurrence of an acute inflammatory response in a subject (patient) due to an infection such as sepsis or other severe acute bacterial infection. In the method, a fluid sample is taken from a patient suspected of having such an infection, or susceptible to having such an infection, for example a hospitalized patient or a patient who has undergone a surgery or other procedure associated with or prone to causing systemic bacterial infections. The fluid sample is tested for CAP37 protein (such as but not limited to, neutrophil-derived CAP37) by combining the sample with a novel anti-CAP37 antibody. When CAP37 protein is detected in the fluid sample, it is predicted that the patient will have sepsis or a severe acute inflammatory response due to bacterial infection. Further, the result can be used to distinguish an acute inflammatory response, which is due to a bacterial infection, from one due to non-infectious causes, particularly in patients for whom it is either too early to obtain accurate microbiological or bacteriological culture data, or wherein treatment decisions must be made before results from such cultures can be obtained. The acute inflammatory response associated with the positive result for CAP37 protein could also be due to acute lung injury or acute respiratory distress syndrome in those individuals having severe acute pulmonary conditions. The present method may be particularly used in patients in Intensive Care Units (ICU) wherein rapid diagnosis is of critical importance.

While the presently disclosed and claimed inventive concept(s) is described below in connection with certain embodiments so that aspects thereof may be more fully understood and appreciated, it is not intended to limit the presently disclosed and claimed inventive concept(s) to these particular embodiments. On the contrary, it is intended to cover all alternatives, modifications and equivalents and other embodiments as described herein may be included within the scope of the presently disclosed and claimed inventive concept(s) as defined by the appended claims. Thus the examples described below, which include particular embodiments, will serve to illustrate the practice of the presently disclosed and claimed inventive concept(s), it being understood that the particulars shown are by way of example and for purposes of illustrative discussion of particular embodiments of the presently disclosed and claimed inventive concept(s) only and are presented in the cause of providing what is believed to be the most useful and readily understood description of procedures as well as of the principles and conceptual aspects of the presently disclosed and claimed inventive concept(s).

The presently disclosed and claimed inventive concept(s) is related to compositions comprising at least one isolated monoclonal antibody (or antigen binding fragment thereof) that specifically binds to CAP37 and isoforms thereof, as explained in further detail below. In one embodiment, the monoclonal antibodies specifically bind to particular epitopes of CAP37 protein, as explained below.

The presently disclosed and claimed inventive concept(s) is also directed to compositions comprising isolated monoclonal antibodies referred to herein as D5F10 and B1B5, and to hybridomas and cells thereof which produce said antibodies. The antibodies are described in further detail below.

The presently disclosed and claimed inventive concept(s) is also directed to hybridoma D5F10, ATCC accession number PTA-122650, as well as compositions comprising same. Said hybridoma was deposited with the American Type Culture Collection Patent Depository (10801 University Boulevard, Manassas, Va. 20110-2209) on Nov. 3, 2015, under the terms of the Budapest Treaty. All restrictions on the availability to the public of the deposited material will be irrevocably removed upon the granting of a patent directed to said mAb, and the deposit will be maintained for 30 years or 5 years after the most recent request (whichever is later). The presently disclosed and claimed inventive concept(s) is also directed to an isolated monoclonal antibody produced by said hybridoma. The mAb produced by said deposited hybridoma will herein after be referred to as D5F10. In addition, the presently disclosed and claimed inventive concept(s) is also directed to a cell of hybridoma D5F10, as well as compositions comprising same.

The presently disclosed and claimed inventive concept(s) is also directed to hybridoma B1B5, ATCC accession number PTA-122649, as well as compositions comprising same. Said hybridoma was deposited with the American Type Culture Collection Patent Depository (10801 University Boulevard, Manassas, Va. 20110-2209) on Nov. 3, 2015, under the terms of the Budapest Treaty. All restrictions on the availability to the public of the deposited material will be irrevocably removed upon the granting of a patent directed to said mAb, and the deposit will be maintained for 30 years or 5 years after the most recent request (whichever is later). The presently disclosed and claimed inventive concept(s) is also directed to an isolated monoclonal antibody produced by said hybridoma. The mAb produced by said deposited hybridoma will herein after be referred to as B1B5. In addition, the presently disclosed and claimed inventive concept(s) is also directed to a cell of hybridoma B1B5, as well as compositions comprising same.

Further, the presently disclosed and claimed inventive concept(s) is also directed to a composition comprising a monoclonal antibody produced by one of the hybridomas D5F10 and B1B5 respectively.

The presently disclosed and claimed inventive concept(s) is also directed to a composition comprising a monoclonal antibody having the same epitope specificity as any of the monoclonal antibodies described herein above. In one embodiment, the mAb has the same epitope specificity as D5F10 or B1B5.

In some embodiments, the antibodies and antigen binding fragments thereof include one or more CDRs that have amino acid sequences identical to a corresponding CDR of D5F10 or B1B5. In some embodiments, certain CDRs of the antibodies or antigen binding fragments thereof have amino acid sequences that are substantially similar, but not identical to, the corresponding CDR of D5F10 or B1B5. In some embodiments, the antibodies and antigen binding fragments thereof have CDR sequences identical to the corresponding CDR sequences of D5F10 or B1B5, except for one or more amino acid mutations in one or more of the CDRs. In some embodiments, the amino acid mutations are present only in at least one of CRDL1, CDRL2, CDRH1 and CDRH2. In some embodiments, the mutations are conservative amino acid substitutions as "conservative" is defined elsewhere herein.

In certain embodiments, the antibodies or antigen binding fragments thereof have a heavy chain variable region having an amino acid sequence that is at least 80%, or at least 85%, or at least 90%, or at least 91%, or at least 92%, or at least 93%, or at least 94%, or at least 95%, or at least 96%, or at least 97%, or at least 98%, or at least 99%, or 100% identical to a heavy chain variable region of D5F10 or B1B5. In certain embodiments, the antibodies or antigen binding fragments thereof have a light chain variable region having an amino acid sequence that is at least 80%, or at least 85%, or at least 90%, or at least 91%, or at least 92%, or at least 93%, or at least 94%, or at least 95%, or at least 96%, or at least 97%, or at least 98%, or at least 99%, or 100% identical to a light chain variable region of D5F10 or B1B5. In some embodiments, the antigen binding antibody fragments do not include a light chain or do not include a heavy chain. For example, in some embodiments the antibody binding fragments are single domain antibodies, such as but not limited to, NANOBODIES® (Ablynx NV, Belgium).

The antibodies or antigen binding fragments thereof can be prepared using an antibody having the $V_H$ and/or $V_L$ sequences of D5F10 and B1B5 as starting material to engineer a modified antibody, which modified antibody may have altered properties from D5F10 and B1B5, but retain the epitope specificity of D5F10 and B1B5, respectively. An antibody or antigen binding fragment thereof can be engineered by modifying one or more residues within one or both variable regions (i.e., the heavy chain variable region or the light chain variable region), for example within one or more CDR regions and/or within one or more framework regions. Additionally or alternatively, an antibody can be engineered by modifying residues within the constant region(s), for example to alter the effector function(s) and/or immunogenicity of the antibody.

The presently disclosed and claimed inventive concept(s) further includes chimeric antibodies that comprise at least a portion of a variable region of and a constant region of an antibody derived from a human. Such antibodies retain D5F10 and B1B5 antigen specificity and ability to bind to CAP37 but have reduced immunogenicity in humans compared to D5F10 and B1B5 antibodies.

As noted above, in some embodiments, the antibodies and antibody fragments are "humanized." Thus, in some embodiments, the antibodies or antigen binding fragments thereof are humanized forms of antibodies or fragments thereof (such as Fv, Fab, Fab', F(ab')2, or other antigen-binding subsequences of antibodies) that are principally comprised of the sequence of a human antibody or antibody fragment but contain all or some of the CDRs from D5F10 and B1B5 antibodies.

Such humanized antibodies or antibody fragments can be generated by substituting the CDRs of D5F10 and BIB5 for the corresponding sequences of a human antibody or antibody fragment. In certain embodiments, a humanized antibody is constructed by replacing CDRs 1-6 of a human antibody with CDRs 1-6 from D5F10 and B1B5. In certain embodiments, a humanized antibody or antibody fragment comprises variable regions in which all of the CDRs correspond to CDRs of D5F10 and B1B5 and all of the framework regions (FRs) correspond to FRs of a human antibody. In some embodiments, the humanized antibody or antibody fragment has a CDRL3 and CDRH3 of D5F10 and B1B5, but retains human sequences for one or more of CDRL1, CDRL2, CDRH1 or CDRH2. In some embodiments, the mutations are conservative sequence modifications. In some instances, certain Fv framework residues of the human immunoglobulin are replaced by corresponding non-human residues. In some embodiments, humanized antibodies can also comprise residues which are found neither in the recipient antibody nor in the imported CDR or framework sequences. Methods of making and/or using humanized monoclonal antibodies can be found, for example, in, Sandborn et al., Gatroenterology, 120:1330 (2001); Mihara et al., Clin. Immunol., 98:319 (2001); Yenari et al., Neurol. Res., 23:72 (2001); Morales et al., Nucl. Med. Biol., 27:199 (2000); Richards et al., Cancer Res., 59:2096 (1999); Yenari et al., Exp. Neurol., 153:223 (1998); and Shinkura et al., Anticancer Res., 18:1217 (1998), all of which are expressly incorporated in their entirety by reference.

In some embodiments, the antibodies or antigen binding fragments thereof are PEGylated. An antibody can be PEGylated, for example, to increase the biological (e.g., serum) half life of the antibody. To PEGylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Typically, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be PEGylated is an aglycosylated antibody. Methods for PEGylating proteins are known in the art and can be applied to the antibodies of the presently disclosed and claimed inventive concept(s). See for example, EP 0 154 316 by Nishimura et al. and EP 0 401 384 by Ishikawa et al.

In some embodiments, the antibodies and antibody fragments have minor variations in the amino acid sequences of antibodies or antigen binding fragments thereof described above, providing that the variations in the amino acid sequence maintain at least 75%, such as at least 80%, 90%, 95%, or 99%, of the original amino acid sequence, and provided that the antibodies/antibody fragments maintain the ability to specifically bind the epitopes of CAP37 described herein. In some embodiments, the modifications are conservative sequence modifications.

The presently disclosed and claimed inventive concept(s) also includes a pharmaceutical composition comprising a therapeutically effective amount of at least one of the monoclonal antibodies or antigen binding fragments thereof described herein and compositions comprising same in combination with a pharmaceutically acceptable carrier. As used herein, a "pharmaceutically acceptable carrier" is a pharmaceutically acceptable solvent, suspending agent or vehicle for delivering the compounds of the presently disclosed and claimed inventive concept(s) to the human or animal. The carrier may be liquid or solid and is selected with the planned manner of administration in mind. Examples of pharmaceutically acceptable carriers that may be utilized in accordance with the presently disclosed and claimed inventive concept(s) include, but are not limited to, PEG, liposomes, ethanol, DMSO, aqueous buffers, oils, and combinations thereof.

The presently disclosed and claimed inventive concept(s) also includes methods of producing the monoclonal antibodies (or antigen binding fragment thereof) described herein above. The monoclonal antibodies and antibody fragments described herein may be produced by any appropriate methodology known or otherwise contemplated within the art. For example but not by way of limitation, preparation of monoclonal antibodies can begin with the production of polyclonal antibodies generated by immunizing a suitable subject (e.g. a mouse) with a polypeptide immunogen (e.g., a polypeptide that includes at least a portion of CAP37 or an isoform thereof). At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natl. Acad. Sci. 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques.

The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387 402; Gefter, M. L. et al. (1977) Somatic Cell Genet. 3:231 36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Once the antibodies have been obtained, for example once individual B cells have been identified and/or monoclonal antibodies have been produced, the sequences encoding the variable regions of these antibodies can be obtained. The variable region sequences can, for example, be obtained by first sequencing the antibody protein produced by the hybridoma, B-cell or phage and determining the encoding nucleic acid sequence. In one embodiment, the immunoglobulin variable region (VH and VL) DNA or cDNA may be sequenced instead. Where the antibody is derived from a hybridoma cell line or isolated B-cell, the cDNAs encoding the variable regions may be amplified using PCR by for example the methods described in Babcook et al. (Proc. Natl. Acad. Sci. USA, 93:7843-7848 (1996)), and in PCT Publication No. WO 92/02551. The contents of both references are expressly incorporated herein by reference in their entirety.

Thus, the antibodies and antigen binding fragments described herein can be generated using a method of producing a monoclonal antibody or antigen binding fragment thereof that includes the steps of providing a cell that produces a monoclonal antibody or antigen binding fragment thereof described herein and culturing the cell under conditions that permit production of the monoclonal antibody or antigen binding fragment thereof. In some embodiments, the cell is the hybridoma having ATCC accession no. or ATCC accession no.

As an alternative to preparing monoclonal antibody-secreting hybridomas, a monoclonal antibody (or fragment thereof) specific for CAP37 or an isoform thereof can be identified and isolated by screening a recombinant combinatorial immunoglobulin library (e.g., an antibody phage display library or an antibody yeast display library) with the appropriate polypeptide to thereby isolate immunoglobulin library members that bind the polypeptide (see, e.g., Clackson et al., Nature, 352: 624-628 (1991); and Marks et al., J. Mol. Biol., 222:581-597 (1991), each of which is incorporated by reference).

Additionally, using antibody and antigen binding fragment sequences provided herein and known in the art, the monoclonal antibodies and antigen binding fragments, including chimeric or humanized monoclonal antibodies, can be made using standard recombinant DNA techniques. Such monoclonal antibodies and antibody fragments can be produced, for example, using methods described in U.S. Pat. No. 4,816,567; U.S. Pat. No. 5,565,332; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060, or U.S. Pat. No. 5,916,771, each of which is hereby incorporated by reference in its entirety.

The presently disclosed and claimed inventive concept(s) also includes isolated nucleic acid molecules encoding the amino acid sequence of any of the monoclonal antibodies (or fragments thereof) described herein above, including but not limited to, the heavy and/or light chain variable domains of said monoclonal antibodies as well as one or more CDRs of said heavy/light chain variable domains. In one embodiment, the presently disclosed and claimed inventive concept(s) comprises isolated nucleic acid molecules encoding at least one of (a) a heavy chain variable region having a CDR1 of antibody D5F10 or B1B5; (b) a heavy chain variable region having a CDR2 of antibody D5F10 or B1B5; (c) a heavy chain variable region having a CDR3 of antibody D5F10 or B1B5; (d) a light chain variable region having a CDR1 of antibody D5F10 or B1B5; (e) a light chain variable region having a CDR2 of antibody D5F10 or B1B5; and (f) a light chain variable region having a CDR3 of antibody D5F10 or B1B5.

Nucleic acids of the presently disclosed and claimed inventive concept(s) can be obtained using standard molecular biology techniques. For antibodies expressed by hybridomas (e.g., hybridomas prepared as described above), cDNAs encoding the light and heavy chains of the antibody made by the hybridoma can be obtained using standard PCR amplification or cDNA cloning techniques. For antibodies obtained from an immunoglobulin gene library (e.g., using phage display techniques), nucleic acid encoding the antibody can be recovered from the library. In some embodiments the isolated nucleic acid molecules have at least 80%, 85%, 90%, 95% or 100% sequence identity to the nucleic acid molecules described above.

The presently disclosed and claimed inventive concept(s) also comprises a vector comprising any of the isolated nucleic acid molecules described herein above. The presently disclosed and claimed inventive concept(s) further include a host cell comprising said nucleic acid molecule(s) and/or said vector. The presently disclosed and claimed inventive concept(s) also comprises a cell or cell line expressing the monoclonal antibodies described herein above, including but not limited to, antibody D5F10 or B1B5.

In certain embodiments of the presently disclosed and claimed inventive concept(s), the novel antibodies or binding fragments thereof are labeled so as to be made detectable via standard imaging techniques such as magnetic resonance imaging (MRI), positron emission tomography (PET) and other such medical imaging techniques known in the art. Such labeled antibodies can be used to diagnose Alzheimer's disease by detecting the presence of CAP37 protein therein.

As is known in the art, MRI is a diagnostic technique in which radio waves generated in a strong magnetic field are used to provide information about hydrogen atoms in different tissues within a human body. A computer uses this information to produce two and three dimensional images of the tissues in many different planes. For example, human tissues that are well-visualized using MRIs include soft tissues such as the brain and spinal cord, abdomen, and joints.

As is known in the art, PET is a type of nuclear medicine imaging in which very small amounts of radioactive materials are used to diagnose diseases. A radioactive tracer is injected into a vein, swallowed by mouth or inhaled as a gas or administered by another suitable route and eventually collects in the area of a human body being examined, where it gives off energy in the form of gamma rays. This energy is detected by a PET scanner. These devices work together with a computer to measure the amount of radio active tracer absorbed by a body and to produce special pictures offering details on both the structure and function of organs and other internal body parts. PET scans measure important body functions, such as blood flow, oxygen use, and sugar metabolism, to help doctors evaluate how well organs and tissues are functioning.

In one embodiment of the presently disclosed and claimed inventive concept(s), at least one of the atomic moieties of a D5F10 or B1B5 antibody or binding fragment thereof is replaced with a non-radioactive ($^{18}$F), paramagnetic ($^{17}$O), or radioactive (e.g., $^{15}$O, $^{13}$N, $^{11}$C, $^{18}$F) isotope of the same or physiochemically related moiety. In one embodiment, replacement atoms include, but are not limited to, replacement atoms in which $^{15}$O atoms are used to replace $^{16}$O atoms, $^{13}$N atoms are used to replace $^{14}$N atoms, $^{11}$C atoms are used to replace $^{12}$C atoms, or hydrogens on the methyl moieties are replaced with $^{18}$F atoms to be used for PET imaging.

Radionuclides which may be used as labels herein in the antibodies or binding fragments thereof, include, but are not limited to, $^{15}$O, $^{13}$N, $^{11}$C, $^{18}$F, $^{76}$Br, $^{77}$Br, $^{123}$I, $^{124}$I, $^{125}$I, $^{99m}$Tc, $^{68}$Cu, $^{62}$Cu, $^{64}$Cu, $^{67}$Ga, $^{68}$Ga, $^{82}$Rb, $^{111}$In, $^{201}$Tl, and $^{123}$Xe. In one embodiment, a kit according to the presently disclosed and claimed inventive concept(s) contains from about 1 to about 50 mCi of the radionuclide-labeled amyloid imaging agent described herein, in combination with a pharmaceutically-acceptable carrier. The diagnostic imaging amounts are typically, but are not limited to, about 1-30 millicuries (mCi) for a 70 kg normal adult, more typically being about 3-20 mCi for a 70 kg normal adult. The amyloid imaging agent and carrier may be provided in solution or in lyophilized form. When the amyloid imaging agent and carrier of the kit are in lyophilized form, the kit may optionally contain a sterile and physiologically acceptable reconstitution medium such as water, saline, buffered saline, and the like. PET imaging is accomplished with the aid of tracer compounds labeled with a positron-emitting isotope (Goodman, M. M. Clinical Positron Emission Tomography, Mosby Yearbook, 1992, K. F. Hubner et al., Chapter 14). These tracer compounds can be labeled with a positron-emitting radionuclide as described herein for example. In general, a PET label, is a label which is covalently attached to the remainder of a molecule and should have a half life of at least about 5-20 minutes, typically about 60 minutes or more.

The imaging agents (i.e., the labeled antibodies or binding fragments thereof) of the presently disclosed and claimed inventive concept(s) may be used in the following manner. An effective amount of an imaging agent comprising at least one targeting molecule and a nuclide (from 1 to 50 mCi) may be combined with a pharmaceutically-acceptable carrier for use in imaging studies. In accordance with the presently disclosed and claimed inventive concept(s), "an effective amount" of the imaging agent is defined as an amount sufficient to yield an acceptable image using equipment which is available for clinical use. An effective amount of the imaging agent may be administered in more than one injection or administration. Effective amounts of the imaging agent will vary according to factors such as the degree of susceptibility of the individual, the age, sex, and weight of the individual, idiosyncratic responses of the individual, and the dosimetry. Effective amounts of the imaging agent will also vary according to instrument and film-related factors. Optimization of such factors is well within the level of skill in the art.

While it is well known that the blood brain barrier presents challenges for the delivery of imaging molecules into the brain, a number of techniques have been developed to enable such molecules as labeled antibodies to be able to pass across the barrier to enable them to be detected by brain imaging techniques when the labeled antibodies bind to target molecules therein. For example, the molecule can be fused with a carrier molecule such as an "angiopep" peptide, (sequences of which are disclosed for example in U.S. Published Applications 2011/0129418 and 2012/0277158), which serves to facilitate the passage of the antibody across the blood brain barrier. There are other means known for facilitating passage of molecules across the blood brain barrier, for example, exposing the brain to focused ultrasound to briefly open up small areas of the blood brain barrier, injecting a hyperosmotic solution into the carotid arteries which causes the blood brain barrier to open briefly by causing the endothelial cells of the barrier to shrink briefly, and administering certain erectile dysfunction drugs such as sildenafil and vardenafil which inhibit phosphodiesterase, thereby increasing the permeability of the barrier. It is thus considered that passage of the antibodies described herein across the blood brain barrier into the brain can be facilitated by methods known to persons having ordinary skill in the art, such as those methods described hereinabove The formulations used in the presently disclosed and claimed inventive concept(s) may also contain pharmaceutically-acceptable carriers, stabilizers, preservatives, buffers, antioxidants, or other additives known to those of skill in the art. The use of such media and agents for pharmaceutically-active substances is well known in the art. Supplementary active compounds can also be incorporated into the imaging agent of the presently disclosed and claimed inventive concept(s). The imaging agent of the presently disclosed and claimed inventive concept(s) may further be administered to an individual in an appropriate diluent or adjuvant, co-administered with enzyme inhibitors or in an appropriate carrier such as human serum albumin or liposomes. Pharmaceutically-acceptable diluents include sterile saline and other aqueous buffer solutions.

As mentioned above, CAP37 protein is involved in a number of cellular phenomonae, both in normal conditions and abnormal. Application to PET diagnosis is thus possible by labeling a CAP37-specific antibody with a radioisotope for example according to the description provided herein, administering the labeled antibody or labeled binding fragment into a body, and performing imaging by detecting the radiation by a PET apparatus. Also, PET diagnosis may possibly be performed by administering an antibody modified by biotin for example, into a body in advance by a pretargeting method, thereafter administering avidin for example that has been modified by a radioisotope, and performing imaging, for example, by detecting the emitted radiation by a PET apparatus. The radioactive isotope may be bound to the antibody directly or indirectly via a chelator or other compound using a known method.

EXAMPLES

Examples of the presently disclosed and claimed inventive concept(s) are provided hereinbelow. However, the presently disclosed and claimed inventive concept(s) is to be understood to not be limited in its application to the specific experimentation, results and laboratory procedures. Rather, the examples are simply provided as one of various embodiments and are meant to be exemplary, not exhaustive.

Example 1

Methods and Materials of Example 1

Human Tissues:
Sections of atherosclerotic vessels (carotid, iliac, coronary and femoral arteries, and aorta) were obtained from the Department of Pathology, University of Oklahoma archival tissue bank.

Cell Culture:
RAECs were isolated and maintained in Dulbecco's Modified Eagle's Medium (DMEM, MEDIATECH, Herndon, Va.) supplemented with 10% fetal bovine serum (HYCLONE, Logan, Utah), as previously described (16). Cells were used within the first 15 passages.

HUVECs were isolated from umbilical cords at the University Hospital, Oklahoma City, Okla., according to methods modified from Jaffe (17). Umbilical veins were washed, flushed with PBS, and the lumen filled with 0.125% trypsin/DMEM for 15 minutes. The cell suspension was centrifuged for 5 minutes at 250×g, and the pellet resuspended in Endothelial Growth Media (EGM, CLONETICS, San Diego, Calif.) supplemented with bovine brain extract (CLONETICS). The cells were passaged at a 1 to 4 split ratio and were used in the first six passages.

Human lung microvessel endothelial cells (HMVEC-L) were purchased from CLONETICS and maintained in ENDOTHELIAL GROWTH MEDIA-2 (CLONETICS). Cells were used within passages 4-11.

Immunochemistry:
Immunohistochemistry on human atherosclerotic tissue sections was performed using published methodology (13). The antiserum used was previously characterized by ELISA and shown to be specific for CAP37(13). Briefly, five μm sections were incubated at 37° C. with the primary anti- CAP37 antiserum (1:500 to 1:2000), followed by biotinylated goat anti-rabbit antiserum (VECTASTAIN ELITE), and then incubated in ABC reagent (VECTASTAIN ELITE). Color was developed with diaminobenzidine (RESEARCH GENETICS, Huntsville, Ala.) for 2-6 minutes. Sections were counterstained with hematoxylin. Antibody controls included normal rabbit serum and immunoadsorbed rabbit anti-CAP37 antiserum, as described previously (13).

For immunocytochemical analysis of rat aorta cells the media was removed and replaced with serum-free DMEM overnight prior to start of the experiment. RAEC were incubated with 10 µg/ml S. minnesota LPS (SIGMA, St. Louis, Mo.) for 0.5, 2, 4, 6 and 24 hours. Untreated cells at each time point were included as a control. The adherent cells on the LAB TEK slides were immunostained for CAP37 as described above (13) except the RAEC slides were fixed in ice-cold 100% methanol and the primary rabbit anti-human CAP37 antiserum was used at a 1:10 dilution.

For immunocytochemical analysis of surface expressed and cell-associated CAP37 in human endothelial cells, the media was replaced with serum free EBM (CLONETICS) 6 h prior to the start of the experiment. HUVECs were incubated in the absence or presence of 10 ng/ml TNFα for 10 and 18 h. Samples were either fixed only or fixed and permeabilized essentially as described by Gräbner (18). Cells were stained as above using commercially-available normal donkey serum (5%) (JACKSON IMMUNORESEARCH LABORATORIES, INC, (West Grove, Pa.) to block nonspecific binding, rabbit anti-human CAP37 (1:750) at room temperature, biotin-sp-donkey F(ab')$_2$ anti-rabbit IgG, (JACKSON, 1:500) and peroxidase-conjugated streptavidin (JACKSON, 2 µg/ml) for amplification of signal. Staining using normal rabbit serum was included as a control.

Northern Blot Analysis:

Total cellular RNA was isolated from RAECs (19). Thirty µg total RNA per well were run on a 1% agarose/formaldehyde gel at 80 mA for 1.5 hours. The RNA was transferred to nylon membrane overnight in SSC (3 M sodium chloride, 0.3 M sodium citrate) transfer buffer and crosslinked to the membrane with a UV crosslinker. CAP37 mRNA was detected by hybridizing a $^{32}$P-labeled CAP37 cDNA probe (6.5 µg probe at 50 µCi/blot), prepared with the PRIME-IT II RANDOM PRIMER KIT (STRATAGENE, La Jolla, Calif.), by incubating with the membrane at 60° C. overnight. Following a low (2×SSC buffer, 0.1% SDS, room temperature) and high (0.1× SSC buffer, 0.1% SDS, 60° C.) stringency wash the membrane was exposed to autoradiograph film at −80° C. To demonstrate the integrity and relative amounts of sample RNA, total cellular RNA (5 µg) was run on a 1% agarose/formaldehyde gel and visualized by ethidium bromide staining.

Western Blot Analysis:

HUVECs were grown to confluency, serum-starved for 6 h prior to start of the experiment, and treated for 12 h with 10 ng/ml TNFα (BOEHRINGER-MANNHEIM, Indianapolis, Ind.). Cells were lysed in 1% SDS/TE (1% SDS, FISHER; TE, 1M Tris, 0.5 M EDTA, pH 8) and 50 µg lysate were loaded per lane onto a 12.5% SDS-PAGE gel and transferred to nitrocellulose membrane (SCHLEICHER and SCHUELL, Keene, N.H.) for Western analysis (6). Briefly, blots were probed for CAP37 using a monospecific polyclonal rabbit antisera against human CAP37 (1:1000) and alkaline-phosphatase conjugated donkey anti-rabbit IgG at 1:1000 (JACKSON), and color developed with Nitro BT/5-Bromo-4-Chloro-3-Indolyl phosphate p-Toluidine salt (FISHER, Fair Lawn, N.J.). An identical blot was probed with normal rabbit serum to show specificity of the reaction. 20 µg PMN extract was included as a positive control for CAP37.

Flow Cytometry:

HUVECs that were serum starved for 6 h were incubated in the absence or presence of 10 ng/ml TNFα for 10 h and 18 h. Permeabilized and non-permeabilized cells were fixed and stained essentially as described by Gräbner (18). The cells were first blocked with 4% normal donkey serum (JACKSON), then incubated at 4° C. with rabbit anti-human CAP37 antisera (1:300), and followed by biotin-sp-donkey F(ab')$_2$ anti-rabbit IgG, (JACKSON, 1:200) at 4° C. For detection the cells were incubated with fluorescein (DTAF)-conjugated streptavidin (JACKSON) at 2 µg/ml at 4° C. Cells were analyzed by flow cytometry (FACSCALIBUR, BECTON DICKINSON, San Jose, Calif.). Unstained cells and cells stained with normal rabbit serum were included as controls.

RT-PCR:

HUVECs from four donors were incubated for 1 to 24 hours at 37° C. with 10 ng/ml TNFα (BOEHRINGER-MANNHEIM, Indianapolis, Ind.). The supernatant was aspirated and the cells homogenized with TRIZOL (GIBCOBRL, Gaithersburg, Md.) according to the manufacturer's instructions for total RNA isolation.

cDNA was prepared using Superscript II reverse transcriptase and oligo $dt_{12-18}$ (GIBCOBRL) essentially according to the manufacturer's protocol with an additional 30 minute incubation at 50° C. prior to termination of the reaction. cDNA was amplified in the polymerase chain reaction with primers designed for a 468 bp internal fragment (5'-GTGCTGGGTGCCTATGACCTGAGG-3' (SEQ ID NO:1) and 5'-AAGAGCGCCACTCGGGTGAAGAA-3' (SEQ ID NO:2)) flanking exons and introns of HL60-CAP37. The PCR reaction mix (1.5 mM MgCl$_2$, 0.3 mM dNTPs, 0.3 units Taq polymerase (GIBCOBRL), 0.4 µM primer mix, and cDNA in a 25 µl total volume) was amplified for 30 cycles on a BIOMETRA T GRADIENT THERMOCYCLER followed by visualization on a 1% agarose gel with 0.5 µg/ml ethidium bromide. RNA samples with no reverse transcriptase were included in the PCR reaction to demonstrate lack of genomic DNA contamination.

Cloning and Sequencing of E-CAP37:

RT-PCR was performed essentially as above using primers designed for an internal (5'-CAGAATCAAGGCAGGCACT-TCTGC-3' (SEQ ID NO:3) and 5'-GAGAACACCATC-GATCCAGTCTCG-3' (SEQ ID NO:4)) 597 bp fragment of CAP37. The products were excised and eluted from the agarose gel with GENE CLEAN II (B10101, Vista, Calif.) and ligated into a pCR2.1 vector (The ORIGINAL TA CLONING KIT, INVITROGEN, Carlsbad, Calif.), and cloned in INVαF' E. coli (ONE SHOT CHEMICALLY COMPETENT E. coli, INVITROGEN, Carlsbad, Calif.) according to the manufacturer's protocol. Plasmids from transformants were sequenced by the Oklahoma Medical Research Foundation Sequencing Facility in both forward and reverse directions using the T7 and M13 reverse primers for 4 clones from 3 separate induction experiments. The resulting sequences were aligned using Pole Bio-Informatique Lyonnais, Network Protein Sequence @nalysis (20) for DNA and the consensus sequence blasted against the HL60-CAP37 cDNA sequence.

Extraction, Purification and Sequencing of CAP37 Isoforms:

CAP37 proteins from endothelial, neuronal, and other sources can be purified and sequenced, in particular for identifying C- and/or N-terminal portions which extend from the SEQ ID NO:7 portion of the CAP37 protein. For example, Rapid Amplification of cDNA ends (RACE) can be used to identify C- or N-terminal sequences of inducible isoforms of CAP37.

RACE enables the amplification of either 5' or 3' end of a specific cDNA starting from a mRNA population. The GIBCO BRL 5' and 3' RACE system can be used, for example. Total cellular RNA is isolated from stimulated endothelial and neuronal cells with Trizol reagent (GIBCO-BRL) and contaminating DNA removed by DNaseI treatment. For 5' RACE, neuronal and endothelial-CAP37 cDNA is synthesized using a CAP37 specific primer 5' CTGCAGAGGCAGTGGCAGTATCGT 3' (SEQ ID NO:5) and Superscript II, an RNase H derivative of Moloney Murine Leukemia Virus Reverse Transcriptase. After the first strand cDNA synthesis, the template mRNA is removed by RNase H treatment and the remaining cDNA purified on a spin cartridge. An oligo-dC sequence is added to the 3' end of the cDNA and amplified by PCR using an Abridged Anchor Primer (GIBCO-BRL) and a second, nested CAP37 specific primer (5' GCAGAAGTGCCTGCCTTGATTCTG 3' (SEQ ID NO:6). The cDNA is re-amplified with the same nested CAP37 specific primer and either the Abridged Universal Amplification or the Universal Amplification Primer. 3' RACE is performed similarly. First strand cDNA synthesis primed with an adapter primer, followed by purification of the cDNA by digesting with RNase H. Amplification is performed using a new CAP37 specific primer (5' CGAGACTGGATCGATGGTGTTCTC 3' (SEQ ID NO: 7), and an oligo dT specific adapter primer. The PCR product may be reamplified using the Abridged Universal Amplification Primer. 5' RACE controls include the omission of RT. Specificity of the anchor primer for the oligo-dC tail is examined by performing amplification reactions with cDNA subjected to dC-tailing both in the presence and absence of TdT. Additional controls that amplify dC-tailed cDNA using each primer individually may be required to identify non specific products that result from mispriming. The PCR products are analyzed by agarose gel electrophoresis (1.4%) and visualized with ethidium bromide staining. A single prominent band on agarose gel is produced by the procedures.

Additional rounds of PCR using successively nested CAP37 specific primers and either the Universal Amplification Primer or the Abridged Universal Amplification Primer may be required. A dilution of the original PCR is used as target. The nested primer is composed of sequences located 3' to the original CAP37 primer. For 5' RACE this is an antisense primer that anneals closer to the mRNA 5' end.

After amplification, 5' RACE products are cloned. Cloning from as little as 1 to 10 pg of the PCR product has been obtained with the CloneAmp pAMP1 system. An alternative cloning technique using the 3' to 5' exonuclease activity of the T4 DNA polymerase may also be used. The PCR products are cloned into the pCR 2.1 plasmid.

DNA Sequencing:

Sequencing is performed using standard methods, such as the Sequencing Core Facility (Oklahoma Medical Research Foundation) using an ABI automated sequencer which can then determine the sequence homology between CAP37 isoforms and PMN-CAP37.

An alternate method of solubilizing and extracting CAP37 isoforms is to use a combination of reverse phase and hydrophobic interaction HPLC to separate functionally active CAP37 from PMN granule extracts using 0.1M glycine pH 3.0 to solubilize and extract the proteins. The extract is applied over a C4 reverse phase column equilibrated in solvent A (0.1% trifluoroacetic acid/2% acetonitrile/98% water). The purification is performed in a two-step gradient. A linear gradient is run to 20% solvent B in 0.4 min, followed by a second linear gradient from 20-75% in 40 min. Solvent B consists of 0.08% TFA/90% acetonitrile/10% water. The fractions are then screened by dot blot for positive reactions with anti-CAP37 antiserum. Further purifications may be performed on a Biogel TSK phenyl, 5PW hydrophobic-interaction HPLC column. In one embodiment, CAP37 can be released into the supernatant by treating the cells with increasing concentrations of heparin as has been shown for certain heparin-releasable proteins that are also heparin binding. In other cases, CAP37 solubilization can be achieved by using solutions of varying salt concentration (0.15 to 0.5 M NaCl) and pH (acidic buffers of pH 3-5, or basic buffers of pH 8-12). EDTA and EGTA may need to be added to destabilize bonds that are enhanced by $Ca^{2+}$ or $Mg^{2+}$.

Alternatively, solubilization may be performed by detergent extraction typical for an amphipathic protein, prior to purification. Crude membrane fractions are prepared by freeze thawing the cells followed by further mechanical disruption using homogenization. A cocktail of protease inhibitors (PMSF at 75 µg/ml, leupeptin at 1-10 µg/ml, pepstatin A at 1-10 µg/ml and/or a combination of 1 mM EDTA and 1 mM EGTA) is incorporated in this step. A series of non-ionic detergents can be used such as NP-40, Triton X-100 or Triton X-114. Further extraction of the pellet at pH 11 for 10-30 min may be required. As for certain $Ca^{2+}$ binding proteins like the annexins, further extractions may be required using octylglucoside or 1% zwitterionic detergents such as CHAPS. Once extraction is achieved, gel filtration followed by one or more of the described purification techniques will be used to purify the CAP37 protein.

Depending on the detergent of choice, a mixture of detergent-protein micelles, detergent-lipid protein-micelles and small membrane fragments will be obtained. Large pore resins such as Sephacryl S-300 and S-400 are used since protein-detergent complexes are substantially larger than the protein alone. The eluted fractions are screened by ELISA, followed by SDS-PAGE and Western blot and those fractions reacting with the CAP37 antiserum are further isolated/purified using affinity chromatography and HPLC as described below:

Affinity Chromatography Using a Rabbit Anti-CAP37 Column:

Extracts are applied to rabbit anti-CAP37 affinity column or mouse anti-CAP37 column. The fractions are eluted and monitored at $A_{214}$ nm (CAP37 is not well detected at $A_{280}$ nm) for protein and then assayed by ELISA for positive fractions.

Affinity Chromatography Using a Bovine Pancreatic Trypsin Inhibitor (BPTI) Column:

CAP37 binds with high affinity to BPTI. The sample is applied to 1 ml column consisting of Mini-Leak (KEN EN TEC BIOTECHNOLOGY) coupled with 30 mg BPTI. CAP37 is eluted using 0.1M glycine pH 3.0.

Reverse-Phase and Hydrophobic Interaction HPLC:

These methods have been used previously for the purification of PMN-CAP37 (2, 3, 6, 21). Additional modifications with RP-HPLC are the use of 60% (v/v) formic acid in the application buffer and a mixture of 60% (v/v) 2-propanol and 40% (v/v) formic acid in the elution buffer. The use of either formic or acetic acid in these buffer systems improves resolution and yield of hydrophobic proteins. Fractions that react positively in dot blots from any one of the above methods are analyzed by silver-stained SDS-PAGE, and western blot to determine extent of purification.

Amino Acid Sequence Analysis of Proteins:

When homogeneous protein is obtained, sequencing is performed by desalting by reverse phase HPLC and the N-terminus sequence determined using the 470A gas phase protein sequencer. The phenylthiohydantoin (PTH)-amino acids are determined on-line with the PTH analyzer. If protein preparations are not sufficiently homogeneous, the sequence of the N-termini can be determined with sufficient separation of the proteins on SDS-PAGE. Samples are run on SDS-PAGE, transferred onto IMMOBILON P membrane and stained with Coomassie Blue. The relevant bands are cut out of the membrane, and directly subjected to sequencing. If the amino terminus is blocked, the proteins are subjected to in-gel and/or in-membrane tryptic digestion. The peptides produced are separated by purification on a UMA micro HPLC system, a technique used to obtain sequence information on N-terminally blocked proteins.

Production of Monoclonal Antibodies (MAbs) Against CAP37:

MAbs were produced by immunizing 3 female, 6-8 weeks old, BALB/c mice (NCI, Bethesda, Md.) with 20 µg of cleaved recombinant CAP37 (rCAP37) emulsified in RIBI (Corixa, Hamilton, Mont.) according to the vendor's instructions, in a total volume of 100 µl, intraperitoneally (i.p.). Cleaved rCAP37 was obtained by treating rCAP37 with Factor Xa (Pierce) at an enzyme to substrate ratio of 1:10 to remove the HPC4 epitope. The mice were immunized 3 times as above, with a 4 week interval between each immunization. Four weeks after the final i.p. injection of cleaved rCAP37 in RIBI, the mice received 20 µg cleaved rCAP37 intravenously in 200 µl of saline solution. The mice were euthanized three days later and the spleens removed for fusion.

Hybridomas were produced by fusing spleen cells from the immunized BALB/c mice with the mouse plasmocytoma cell line SP2-0 in 50% polyethylene glycol (Sigma, St. Louis, Mo.). Hybridomas were selected with hypoxanthine-aminopterine-thymidine (HAT) medium (Sigma) and positive clones producing IgG against CAP37 were detected by ELISA using cleaved rCAP37 and neutrophil lysate as antigens. Stable reactive hybridomas were selected and cloned at least three times by limiting dilution. The MAbs were then purified, from tissue culture supernatants using a Protein-G Sepharose 4 Fast Flow column (Amersham Pharmacia Biotech, Piscataway, N.J.) following the manufacturer's protocol. The purity of MAbs was observed by gel electrophoresis stained with CodeGel Blue Stain Reagent (PIERCE). A total of 9 culture supernatants demonstrated antibodies against CAP37. From these, two hybridoma cell lines were stabilized and continuously monitored and were found to continue to secrete anti-CAP37 antibodies after 3 sub clonings by limiting dilution. These monoclonal antibodies and the hybridomas which produce them were designated as D5F10 and B1B5, respectively. Both antibodies recognized the native and recombinant forms of CAP37.

To determine the specificity of the monoclonal antibodies for CAP37, ELISA and Western blot analysis were used according to standard protocols. The antibodies were tested for cross reaction against other neutrophil-derived proteins, including myeloperoxidase, lactoferrin, defensins, cathepsin G, and elastase. Both techniques indicated that the monoclonal antibodies D5F10 and B1B5 only recognized the rCAP37 and native CAP37 protein, with no cross reaction with the other proteins.

The monoclonal antibodies were isotyped using an ELISA isotyping kit (PIERCE). Monoclonal antibody D5F10 was an IgG1 antibody and monoclonal antibody B1B5 was an IgG3 antibody. Both of them contained k light chains.

In addition to demonstrating the specific reaction with recombinant CAP37 and native CAP37, the different epitopes or domains of the CAP37 molecule that were recognized by the two monoclonal antibodies were identified. Peptides based on the native CAP37 sequence were synthesized so as to span the full length of the molecule. The peptides were designated as 1-25, 20-44, 38-53, 50-77, 70-97, 95-122, 120-146, 140-165, 160-185, 180-202, and 197-222, and named according to the number of the amino acid of the native CAP37 molecule. Dot blot analysis with D5F10 and B1B5 was performed according to standard protocols. Monoclonal antibody D5F10 recognized an epitope between amino acids 20-44, a region known to be involved with the bactericidal property of CAP37, plus additional epitopes located between amino acids 180-202 and 197-222. Monoclonal antibody B1B5 recognized an epitope between amino acids 95 and 122, a region involved in the chemotactic effect of CAP37, plus an epitope in the C-terminal region corresponding to amino acids 197-222. Immunohistochemical staining showed that monoclonal antibodies D5F10 and B1B5 reacted with the granule contents of human peripheral blood neutrophils, which is the location of constitutively expressed neutrophil-CAP37. The monoclonal antibodies did not stain other peripheral blood leukocytes which included eosinophils, monocytes and lymphocytes. A control mouse isotype antibody did not stain human neutrophils, indicating the specificity of the two monoclonal antibodies for CAP37.

Monoclonal antibody, D5F10 which recognized the CAP37 epitope between amino acids 20-44 inhibited bactericidal activity of the recombinant CAP37 and native CAP37. Monoclonal antibody B1B5 which reacted with peptide 95-122, inhibited the chemotactic activity of native and recombinant CAP37 for human monocytes and human corneal epithelial cells.

Results of Example 1

The results in summary indicate that (1) CAP37 is present in atherosclerotic plaques, (2) CAP37 can be induced in cultured endothelial cells, (3) a predominant portion of endothelial derived CAP37 (referred to herein as E-CAP37) is identical to PMN-CAP37, and (4) E-CAP37 is mainly cell-associated.

Tissue sections from human atherosclerotic lesions showed strong staining for CAP37 in the endothelium associated with the plaque area (FIG. 1A). CAP37 was also detected in and around foam cells and cholesterol clefts in plaques with advanced disease (FIG. 1B). Normal endothelium away from the injured endothelium associated with the plaque did not stain for CAP37 (FIG. 1C). Antibody controls using immunoadsorbed antisera to CAP37 (13) showed no staining for CAP37 (FIG. 1D) indicating the specificity of the reaction obtained in FIGS. 1A, 1B and 1C.

Since CAP37 was detected in the endothelium of atherosclerotic plaques but not in normal endothelium, it was hypothesized that CAP37 was induced in response to injurious and/or inflammatory mediators. To explore this possibility, endothelial cells were obtained from various vascular beds including rat aorta (RAECs), human umbilical vein (HUVECs), and human lung microvessel (HMVEC-L) and treated these cell cultures with LPS and cytokines including TNFα and IL-1. Immunocytochemical, Northern blot analysis, and RT-PCR were used to detect CAP37. The immunocytochemical data presented here (FIG. 2) were obtained from RAECs. CAP37 protein was detected in LPS-treated endothelial cells as early as 2 h. Maximum staining was obtained between 4 h (FIG. 2A) and 6 hours. Staining was reduced, but still evident at 24 hours. Untreated cells (FIG. 2B) did not stain at any of the time points with anti CAP37 antiserum. Antibody controls using normal rabbit serum showed virtually no background staining. Similar studies using HUVECs and HMVEC-Ls indicated expression of CAP37 in response to LPS (data not shown).

Figure 3:
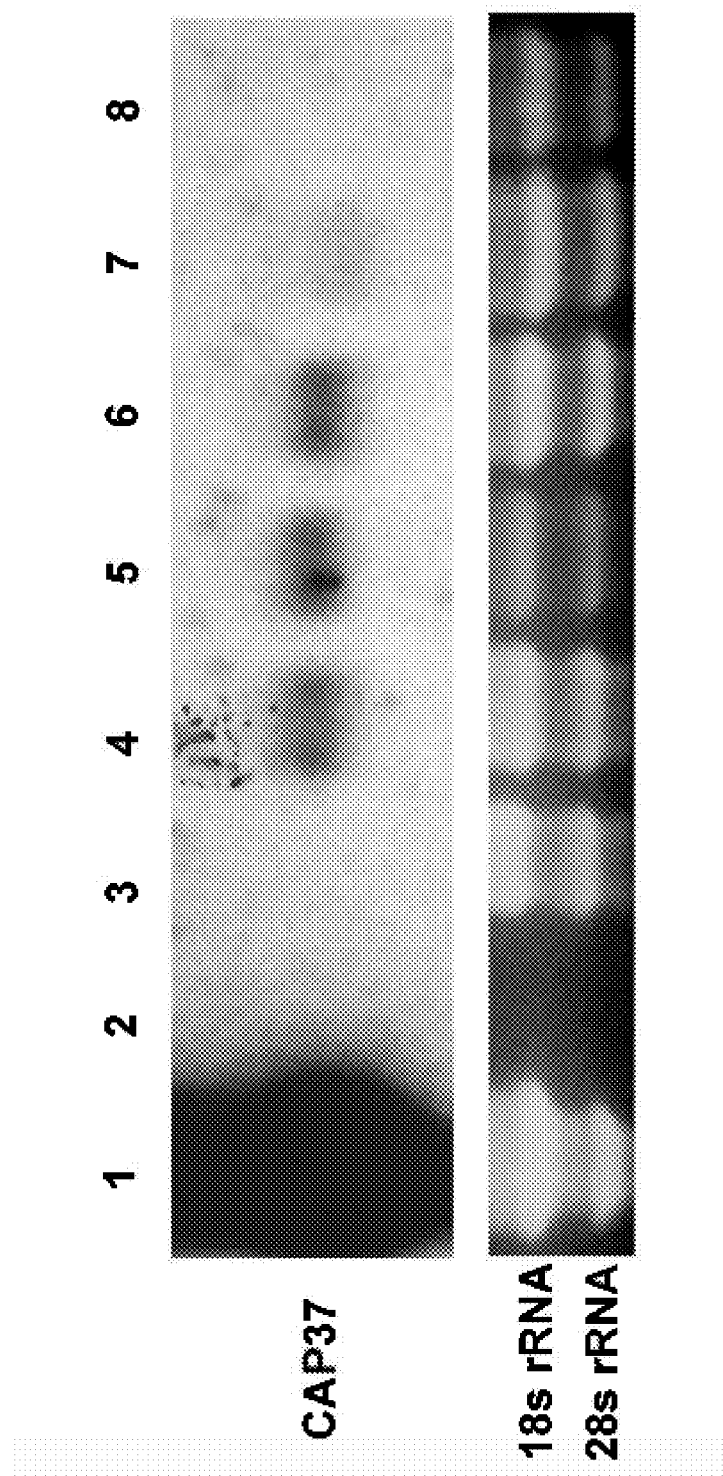
FIG. 3: Northern blot analysis of CAP37 mRNA in RAEC. Rat aorta endothelial cells were stimulated for 0 (Lane 3), 0.5 (Lane 4), 2 (Lane 5), 4 (Lane 6), 6 (Lane 7) and 24 hours (Lane 8) with *Salmonella minnesota* LPS and the Northern blot performed on total RNA from each time point using the $^{32}$P-labeled CAP37 cDNA probe as described in text. An HL-60 cell line (Lane 1) used as a positive control indicated presence of CAP37 mRNA (1000 bp). 18S and 28S rRNA (lower panel) of total cellular RNA demonstrating the integrity and relative amounts of RNA. Lane 2 is empty.

To further corroborate our immunocytochemical data, total cellular RNA was isolated from unstimulated RAECs and RAECs stimulated with 10 μg/ml S. minnesota LPS over a time course spanning 30 minutes to 24 hours and performed Northern blot analysis to identify CAP37 mRNA. Using a $^{32}$P-labeled CAP37 cDNA probe, CAP37 mRNA was detected at 30 minutes in LPS-stimulated cultures. CAP37 mRNA was also present in 2, 4 and 6 hour stimulated cultures but was not detected at 24 hour (FIG. 3). CAP37 mRNA was not detected in unstimulated cultures at any time point. An HL-60 cell line (abundant in CAP37 mRNA)(21) was used as a positive control.

Figure 4:
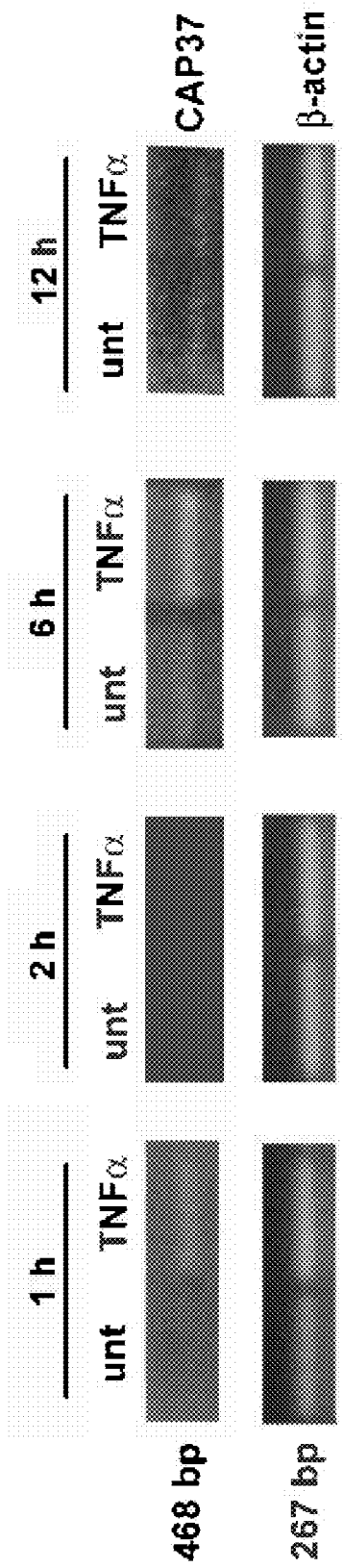
FIG. 4: RT-PCR analysis of human umbilical vein endothelial cells (HUVECs) for CAP37 mRNA. Human umbilical vein endothelial cells were incubated with 10 ng/ml TNFα (TNFα) or left untreated (unt) for the indicated times and CAP37 mRNA expression (upper panel, 468 bp) determined by RT-PCR. cDNA integrity was assessed with β-actin primers (lower panel, 267 bp). This is a representative figure of five independent experiments.

In addition to the above studies with LPS-treated RAECs, the induction of CAP37 was demonstrated in HUVECs in response to the inflammatory cytokine TNFα. These studies were performed by incubating HUVECs in the absence or presence of 10 ng/ml TNFα. CAP37 mRNA induction was assessed by RT-PCR. Kinetic studies performed over a 24 hour time period indicated that CAP37 mRNA significantly increased following TNFα stimulation. Initial upregulated expression was observed as early as 1 hr and in general persisted for a 6 hr time period (FIG. 4). In certain experiments, upregulated expression of CAP37 was observed as late as 12 h. In contrast to the northern blot data using RAECs, constitutive CAP37 mRNA expression was observed in HUVECs using RT-PCR. RT-PCR was performed with primers designed to flank exons and introns of CAP37 so that any genomic DNA contamination would be readily apparent (appearing as a PCR product much larger than that obtained from cDNA). In addition, the control PCR reactions using RNA samples containing no reverse transcriptase did not detect genomic DNA contamination.

Final confirmation that we were in fact dealing with CAP37 was obtained from sequence data. An extensive region of E-CAP37 was cloned, and the cDNA sequence thereof was compared to the known HL60-CAP37 (21) sequence. This comparison demonstrated complete identity with amino acids 19-217 (SEQ ID NO:8) of PMN-CAP37.

To determine whether the induced form of CAP37 was cell associated or released, a series of experiments was undertaken that included immunocytochemistry, flow cytometry, ELISA and western blot analysis. In the immunocytochemical studies, HUVECs were treated with TNFα, and the staining pattern for CAP37 was compared in fixed cells with permeabilized cells. FIG. 5A indicates that there is virtually no CAP37 detected when cells are fixed but not permeabilized indicating that there is very minimal, if any, cell surface expressed CAP37. This is true regardless of whether cells are treated with TNFα (FIG. 5A) or remain untreated (FIG. 5B). On the other hand, when TNFα treated cells are permeabilized, dramatic staining for CAP37 was observed, indicating that a major component of endothelial CAP37 is cell associated (FIG. 5C). The staining is punctate throughout the cytoplasm with visible perinuclear localization. Untreated cells indicate a minimal amount of intracellular staining (FIG. 5D) in comparison to the treated cells. Antibody controls using normal rabbit serum show absence of staining in TNFα treated cells (FIG. 5E).

Figure 5:
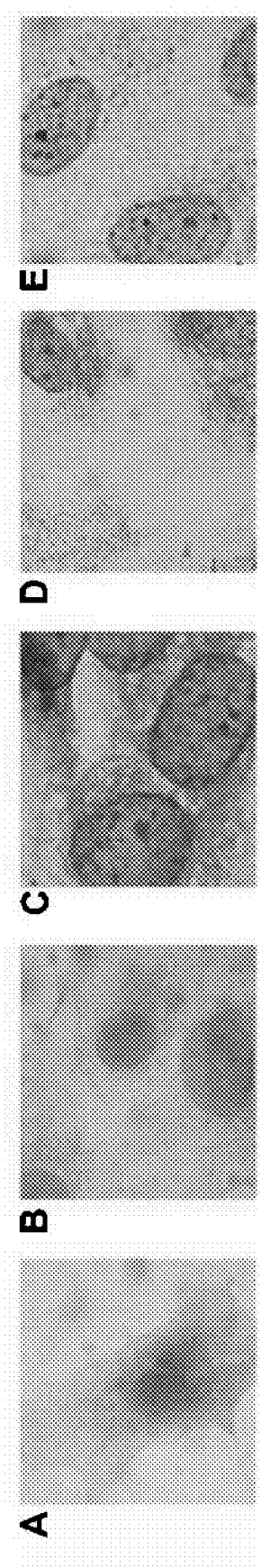
FIG. 5: Immunocytochemical assessment of surface bound and cell-associated CAP37 in HUVECs. A: HUVECs incubated with TNFα for 10 h, fixed (but not permeabilized), and stained with antisera to CAP37 indicating no staining for CAP37 on the outer surface of the cell (×1000). B: Untreated HUVECs, fixed but not permeabilized and stained with antisera to CAP37 indicating lack of staining (×1000). C: HUVECs incubated with 10 ng/ml TNFα for 10 h, permeabilized and stained with antisera to CAP37 indicating strong cytoplasmic and perinuclear staining for CAP37 (×1000). D: HUVECs incubated with media alone for 10 h, permeabilized, and stained with antisera to CAP37 indicating light intracellular staining (×1000). E: HUVECs incubated with media alone for 10 h, permeabilized, and stained with normal rabbit serum indicating no staining (×1000).
Figure 6:
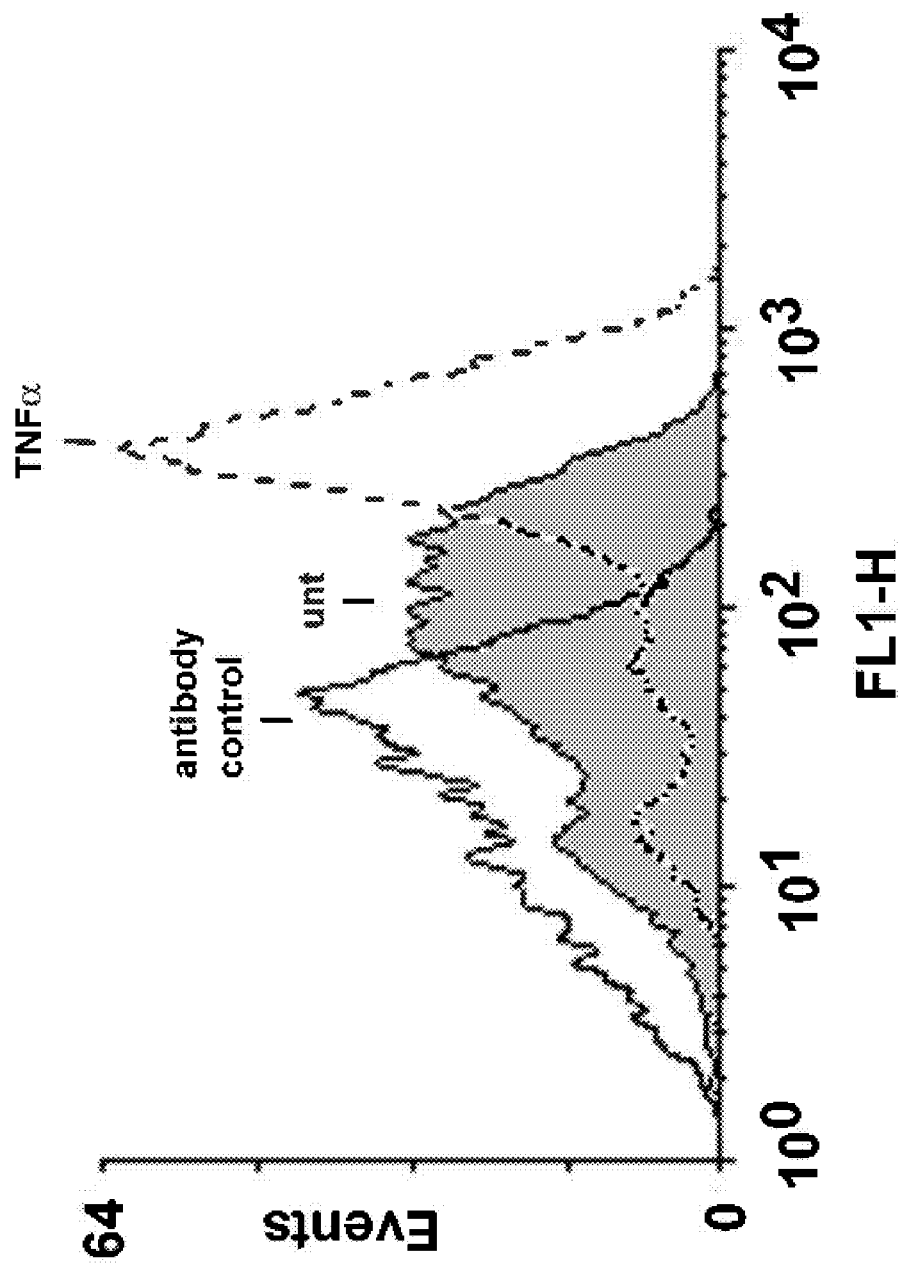
FIG. 6: Flow cytometric analysis of cell associated CAP37 in HUVECs. HUVECs were incubated 18 h in the absence (unt) or presence of 10 ng/ml TNFα (TNFα), permeabilized and labeled with antisera to human CAP37 or normal serum control. Cells were permeabilized to determine intracellular levels of CAP37. A representative histogram from two independent experiments. The shift due to FITC-staining indicates increased expression of CAP37 in TNFα stimulated cells. Also indicated is a low level of constitutive CAP37 expression (unt).

Flow cytometry confirmed the studies described in FIG. 5. TNFα treated cells that were permeabilized indicated up to a 5-fold increase of CAP37 expression over untreated cells (FIG. 6). Once again, the data indicated that there is a low level of constitutive expression of CAP37 protein in HUVECs. No detectable surface expression of CAP37 was observed in non-permeabilized cells using flow cytometry irrespective of whether cells were treated or untreated (data not shown). To determine whether CAP37 is released from treated endothelial cells, ELISA was used to analyze supernatants from TNFα treated HUVEC cultures. Levels of released CAP37 from treated HUVECs were two-fold over untreated cells (data not shown). It was clear that the amount and proportion of CAP37 released from HUVECs was in general much less than the amount and proportion of CAP37 released from PMN (6). Almost 90% of total CAP37 is released from PMN following phagocytosis (6).

Figure 7:
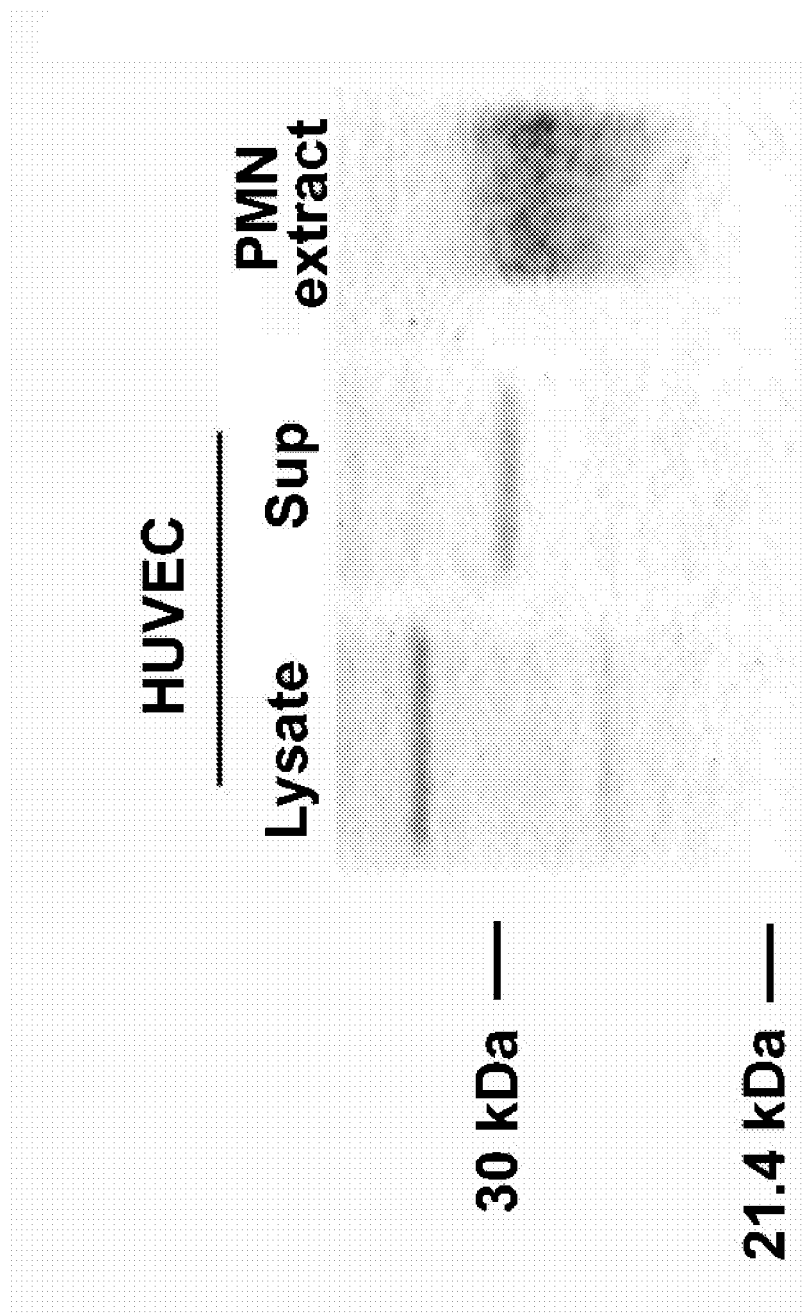
FIG. 7: Western blot analysis of HUVECs for CAP37 protein. Human umbilical vein endothelial cells were incubated with TNFα. 50 μg total protein was loaded into each lane. CAP37 protein expression, both cell associated (lysate) and released (sup), was determined using rabbit antisera to human CAP37. PMN extract (20 μg) included as a positive control for CAP37 staining.

Western blot analysis of HUVEC lysates and supernatants from TNFα treated cells was performed to provide information regarding the molecular mass and processing of the various CAP37 species. FIG. 7 indicates an extremely interesting finding. The released form of CAP37 from HUVECs appears to have a molecular mass closely correlating with the major form of PMN-derived protein, and is clearly a single species. However, there are two forms of the cell associated form of endothelial CAP37, one that migrates with a molecular mass of approximately 26 kDa and another stronger band at approximately 33 kDa. Due to the differential glycosylation of PMN-derived CAP37, the protein migrates as a smear on SDS-PAGE with a range of molecular mass between 24 to 37 kDa. Normal rabbit serum, used as a control antibody to probe an identical blot showed no reaction with HUVEC lysate, supernatant, or PMN extract indicating the specificity of the antiserum used (data not shown).

Example 2

In addition to the expression of CAP37 in atherosclerosis, its expression in an inflammatory mediated disease of the central nervous system, viz Alzheimer's disease (AD) has further been demonstrated.

CAP37 is expressed in hippocampal neurons exhibiting granulovacuolar degeneration (FIG. 8A). Fine granular deposits throughout the neurophil also stained positive for CAP37. AD Brains from individuals with Alzheimer's disease which were stained with normal mouse serum (FIG. 8B) showed no staining in neurons, indicating the specificity of the staining for CAP37. Normal age-matched control brains from non-demented persons showed extremely weak to no staining for CAP37 in neurons (FIG. 8C) microvasculature, and neurophil. Antibody controls using normal mouse serum showed no staining (FIG. 8D). Immunohistochemical staining performed on sections form patients with other neuropathologic conditions showed no staining for CAP37 in neurons. Further studies performed on Alzheimer's disease and Vascular Dementia cortical brain tissue from temporal and parietal lobes stained with mouse monoclonal anti-CAP37 IgG D5F10 showed strong staining in the Alzheimer's Disease neuron cell bodies. Staining for CAP37 varied from localized staining in pyramidal layers 3 & 5 to a diffuse cortical distribution. Vascular Dementia patients showed little to no neuronal CAP37 staining with monoclonal antibody D5F10.

Figure 9:
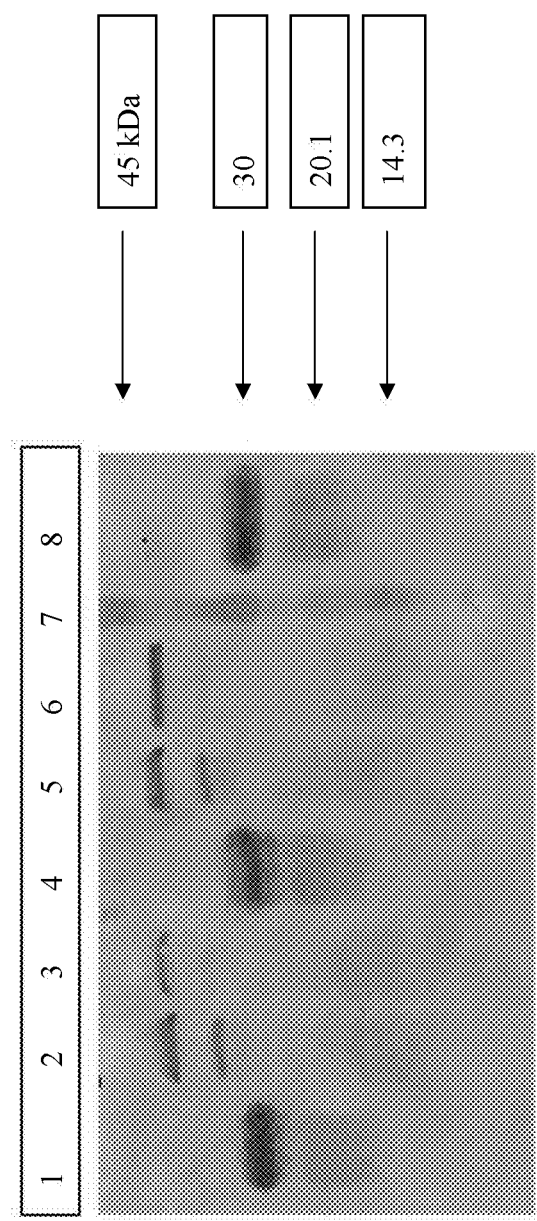
FIG. 9: Western blot analysis of extracts of AD brains and normal age-matched controls with anti-CAP37 antiserum. Lane 1, PMN CAP37; lane 2, AD patient #1; lane 3, control #1; lane 4, PMN CAP37; lane 5 AD patient #2; lane 6, control #2; lane 7, m.w. markers; lane 8, PMN CAP37. Equivalent amounts of protein (4.6 μg) loaded in AD and control lanes and 300 ng of purified CAP 37.

Western blot analysis on extracts of brain tissue from two different Alzheimer's disease patients and two age-matched controls (FIG. 9) indicated the reaction of two molecular species in Alzheimer's disease patients with the anti-CAP37 antiserum. One band migrated at approximately 46 kDa and the other at approximately 40 kDa. The larger band was present in age-matched controls as well; however, the 40 kDa band was specific to Alzheimer's disease patients. The 40 kDa band is a neuronal CAP37 having a slightly greater molecular weight than PMN CAP37. In addition to detecting the 40 kDa band in the brain, the D5F10 antibody may also be able to detect the high MW CAP37 (~100 kDa) in serum, plasma, and/or CSF.

Figure 10:
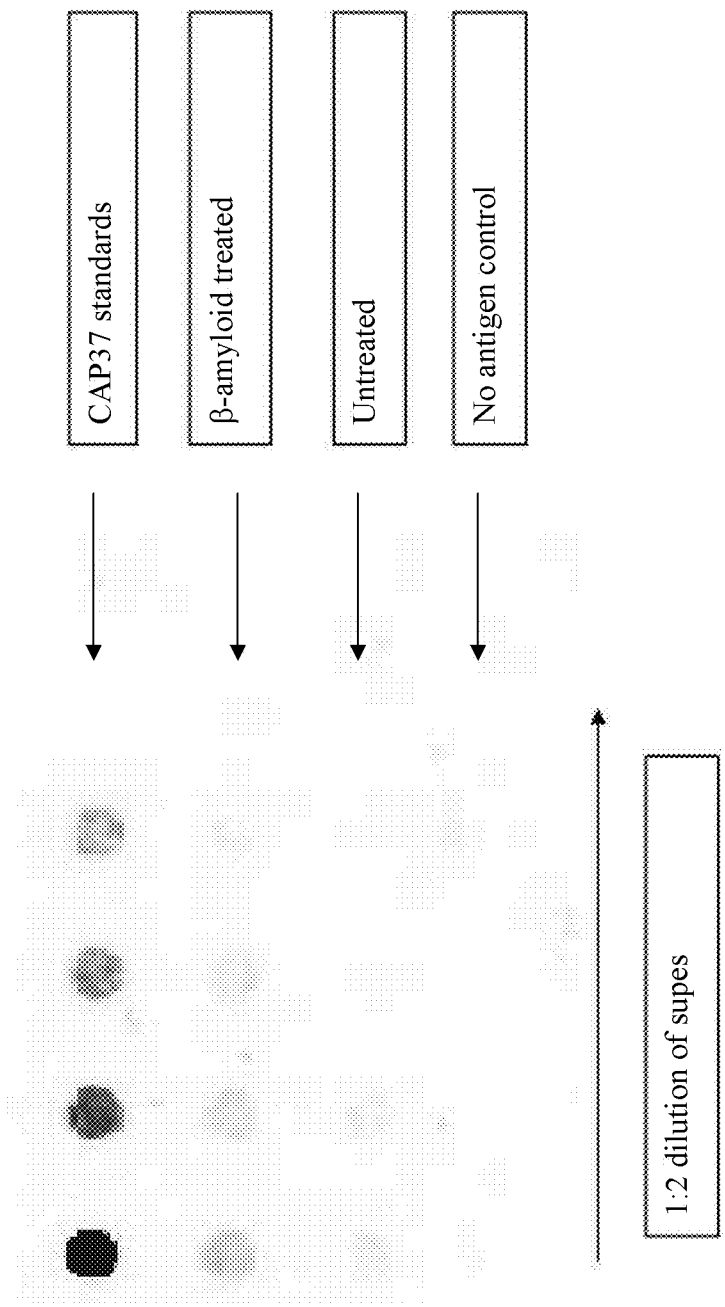
FIG. 10: Dot blot analysis of supernatants from human neuronal cells in vitro with anti-CAP37 antiserum. Top row (from left to right) consists of CAP37 standards, at 20, 10, 5 and 2.5 μg/ml. $2^{nd}$ row consists of doubling dilutions of supes from β-amyloid treated neuronal cultures. Row 3 consists of doubling dilutions of supes from untreated neuronal cultures. Row 4-no antigen/control.
Figure 11:
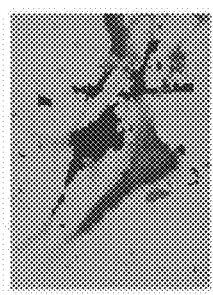
FIG. 11: Immunocytochemical localization of CAP37 in cultured human neurons. A. HCN-1A neurons were cultured and treated with β-amyloid (75 μg/ml) and stained with anti-CAP37 antiserum. Strong staining was obtained within cells after 12 hr of treatment. B. Neurons treated with β-amyloid and reacted with normal mouse serum show no staining for CAP37. C. Untreated cells with anti-CAP37 antiserum also show no staining indicating that CAP37 is not constitutively expressed in neurons but is induced (×400).
Figure 11:
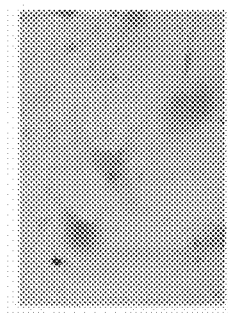
Figure 11:
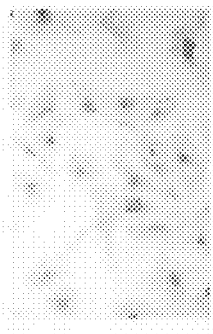

The expression of CAP37 in neurons was further corroborated using in vitro culture. Human neuronal cells (ATCC, HCN-1A) were cultured according to specifications, transferred to serum-free medium for 6 hr and treated with β-amyloid fragment 1-42 (75 μg/ml), control peptide 40-1 (75 μg/ml), and media for 12 hrs. Supernatants were analyzed by dot blot for presence of released CAP37 (FIG. 10) and cells stained with anti-CAP37 antiserum (FIG. 11A) and normal mouse serum (FIG. 11B) to determine cell-associated CAP37. As can be seen CAP37 is not present in untreated neurons (FIG. 11C), but is strongly expressed in cells treated with β-amyloid, and can be detected as a released (secreted) form in supernatants at a concentration of approximately 2.5 μg/ml.

The association of CAP37 with diseases such as Alzheimer's disease, osteoarthritis, and atherosclerosis, as shown herein, indicates that CAP37 is an important mediator of inflammation leading to the exacerbation or augmentation of chronic inflammatory responses observed in inflammatory-associated (mediated) diseases such as Alzheimer's disease, osteoarthritis, atherosclerosis, psoriasis, and others described herein.

The presently disclosed and claimed inventive concept(s) therefore comprises in one embodiment a diagnostic test for atherosclerosis, osteoarthritis, psoriasis, Alzheimer's disease, and other chronic inflammatory-associated (mediated) diseases including asthma, rheumatoid arthritis, and inflammatory diseases of the bowel such as Crohn's disease, Ulcerative colitis, Irritable bowel syndrome and Inflammatory bowel disease.

Figure 8:
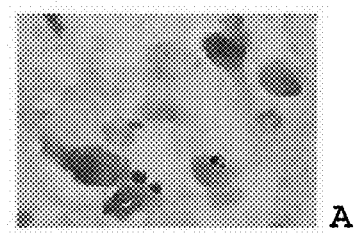
FIG. 8: Immunocytochemical localization of CAP37 in AD (A & B) and normal control brain (C & D). Sections were stained using monospecific mouse anti-human CAP37 antiserum (1:1000) and normal mouse serum (1:1000) and the VECTASTAIN-ABC-PEROXIDASE technique. A. AD brain with anti-CAP37 serum showing strong positive stain in neurons (×400). B. AD brain with normal mouse serum showing negative stain in neurons (×200). C. Normal age-matched control brain with mouse anti-CAP37 antiserum showing lack of staining in neurons (X 200). D. Normal age-matched control with normal mouse serum (×200).
Figure 8:
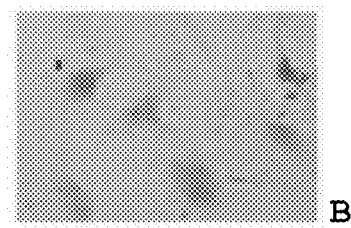
Figure 8:
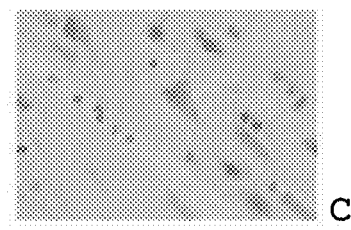
Figure 8:
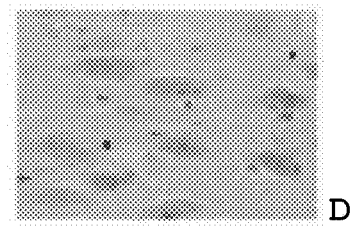

The results shown herein demonstrate novel and important observations about the inflammatory mediator CAP37. Firstly, its presence in atherosclerotic lesions and in and round foam cells, and cholesterol clefts in complex plaques has convincingly been demonstrated. Secondly, its presence in vascular endothelium and neurons of Alzheimer's disease patients has also been demonstrated (FIG. 8). Thirdly, the presence of induced forms of CAP37 in endothelial cells and neuronal cells in response to cytokines and injurious mediators such as LPS and TNFα which are related to inflammatory diseases has also been demonstrated. This is the first demonstration of endogenous endothelial or vascular CAP37 and of a secreted neuronal CAP37.

Sequence analysis demonstrated substantial homology between E-CAP37 and PMN-CAP37, with a complete match of 199 amino acids from residue 19 through residue 217 (SEQ ID NO:8, which is encoded by the cDNA SEQ ID NO:9). This homologous region includes coding sequence for the domains of PMN-CAP37 reported to have bactericidal (22) and endotoxin neutralizing (5) activity. The region reported to activate PKC (11) in endothelial cells is also included within this region. Mature PMN-CAP37 is a 222 amino acid molecule (including SEQ ID NO:8) and having a calculated molecular mass of approximately 24 kDa (3). Molecular masses ranging from 37 kDa to 24 kDa have been observed on SDS-PAGE due to its differential glycosylation (3). Based on the calculated molecular mass of one form of endothelial CAP37 observed on our Western blots one would expect to find differences/extensions at the amino- and/or carboxy terminus end of the molecule. It is not unusual for inducible and constitutively expressed forms of the same molecule to have variations in size and amino acid sequence. This has been well documented for IL-12 (23,24).

In addition to the differences in molecular mass between inducible E-CAP37 and PMN-derived CAP37, our results suggest differences relating to the processing of E-CAP37. Previous findings from our laboratory indicate that PMN-derived CAP37 is easily released from the granules of the PMN on activation, with almost 90% of total CAP37 detected in supernatant fluids (6). On the other hand, E-CAP37 comprises distinct cell-associated and released forms. The cell-associated protein migrated as a higher kDa band while the released protein migrated equivalently to the PMN-derived protein. The two isoforms of IL-1, for example, also demonstrate a differential pattern of extracellular release, IL-1β is easily released, whereas IL-1α is not (25).

Figure 2:
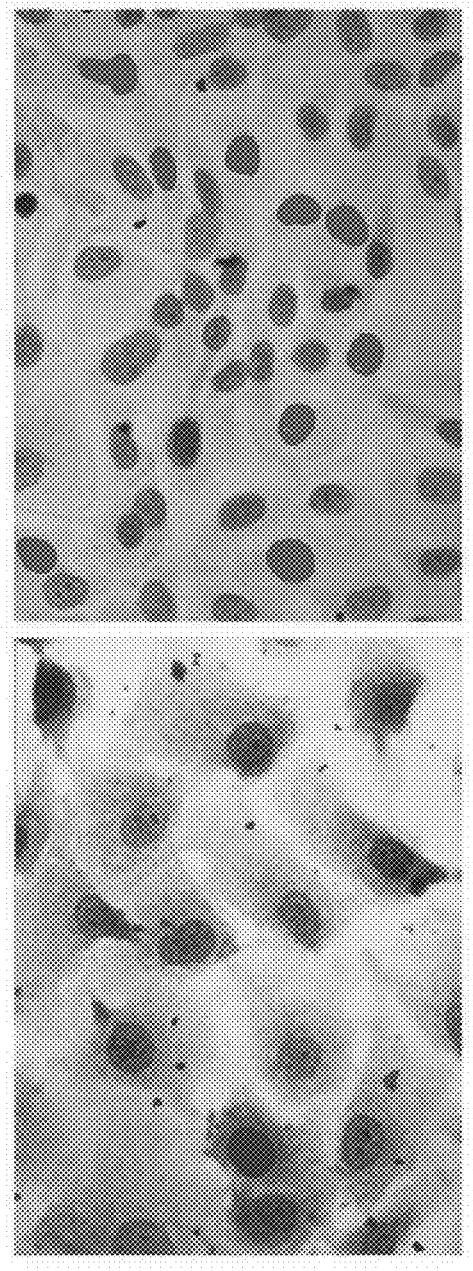
FIG. 2: Induction of CAP37 protein in rat aorta endothelial cells (RAECs). A: Immunocytochemistry of RAECs stimulated with 10 μg/ml LPS for 4 hours and stained with antisera to CAP37 using the VECTASTAIN ELITE ABC technique indicating strong staining for CAP37 (×400). B: RAECs incubated with media alone and stained with antisera to CAP37 shows no positive reaction, indicating that E-CAP37 is not constitutively expressed in RAECs (×200). Sections were counterstained with hematoxylin.

To explore the identity of the mediators involved in the induction of CAP37 in endothelium, a series of in vitro studies were undertaken. In FIG. 2, it has been demonstrated immunohistochemically that CAP37 is induced in endothelial cells in response to the injurious mediator, LPS. Kinetic studies showed that CAP37 protein was induced in rat aorta endothelial cells in vitro by LPS as early as 30 minutes, peaked at 4-6 hours, and subsided by 24 hours. Corroborative studies using Northern blot analysis demonstrated the expression of CAP37 mRNA to follow a similar time course in which expression is no longer detected at 24 hours of LPS stimulation. The antiserum used for these experiments was raised against human CAP37 (13), and the probes used for the northern blot analysis were based on the human CAP37 sequence (21) indicating that there is significant conservation of CAP37 across species (6,11,27). The present studies were performed using rat aorta endothelial cells since it was believed that endothelial cells derived from the aorta would be the most appropriate site for studies dealing with atherosclerosis. It is important to note that this induction of CAP37 in endothelial cells does not appear to be limited to the aorta. Other studies from our laboratory indicate that TNF-α and IL-1α can induce CAP37 in cultured endothelial cells from rat cerebral microvessel endothelial cells (13) and as described in FIGS. 4 through 7 can also be induced in HUVECs and in HMVEC-Ls. It's particularly interesting that PMN-CAP37 is entirely constitutive and cannot be induced. In fact, mature PMN lack mRNA for CAP37 (21). In endothelial cells the constitutive expression of basal mRNA and protein levels appeared to vary. As seen in the figures with rat aorta, no constitutive levels were found, even at the mRNA or protein level, whereas the study with HUVECs and HMVEC-Ls indicated some constitutive expression. This may reflect the species from which the cells are obtained, since rat cerebral vessel showed no constitutive expression either (13).

Our immunohistochemical data on atherosclerotic lesions demonstrate that the expression of CAP37 protein is not confined solely to the endothelium but is also detected throughout the cholesterol clefts, foam cells, and proliferating smooth muscle cells in the subintimal area of advanced lesions. Our data further indicate that the CAP37 expressed in the endothelium is endogenous E-CAP37. The CAP37 in the smooth muscle cells is of endogenous origin, since ongoing studies in our laboratory indicate that CAP37 is expressed in proliferating smooth muscle cells. Following injury to the endothelium, platelets and/or PMN will adhere to it due to upregulation of various adhesion molecules, and on activation will release CAP37. In addition, CAP37 is induced in endothelial cells in response to inflammatory cytokines. The presence of exogenous and endogenous CAP37 sets up a chemotactic gradient across the endothelium which ensures recruitment and migration of monocytes. CAP37 could also contribute to endothelial contraction (7) further influencing the transmigration of leukocytes across the endothelium.

As shown herein, a neuronal form of CAP37 has been identified in the neurons of patients dying from Alzheimer's disease. In vitro tissue culture assays performed in our laboratory using human neuronal cell lines show that CAP37 in induced in human neurons in response to the toxic 42-amino acid beta-amyloid peptide. This was assayed by immunohistochemistry using mouse anti-CAP37 antiserum and by dot blot assay. The dot blot assay was performed on supernatants collected from the cell cultures and indicates that the CAP37 is liberated into the supernatants without any physical or mechanical perturbation of the cells. Thus it is evident that neuronal CAP37 of subjects suffering from Alzheimer's disease is easily released into the extracellular milieu wherein the neuronal CAP37 can be identified and assayed in either in the cerebrospinal fluid or in the patient's plasma or serum.

Example 3

Osteoarthritis

Figure 12:
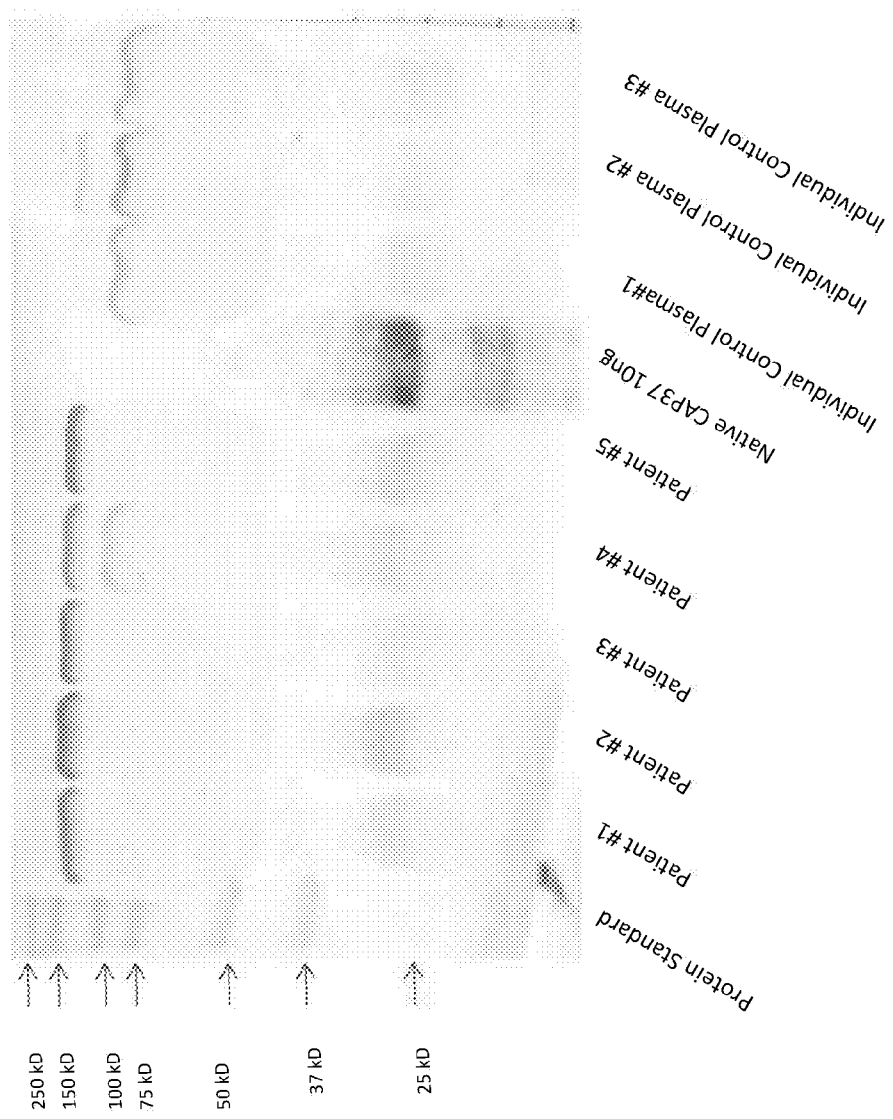
FIG. 12 is an image of a Western blot analysis of plasma samples from five patients diagnosed with osteoarthritis which shows the presence of a high molecular weight (~135 kDa) isoform of CAP37 protein in the plasma samples. The CAP37 isoform is captured by polyclonal rabbit anti-CAP37 IgG antibody (2.5 mg/ml, 1:50,000). Native CAP37 protein is shown in a band of about 28-37 kDa. Molecular weights of the CAP37 isoforms were determined by measuring the distance migrated from the origin of the gel of each isoform and comparing this distance in mm to the distance migrated by known molecular weight markers that were electrophoresed side-by-side on a 10% SDS polyacrylamide gel. Molecular weight markers (Precision Plus Protein Standards, Kaleidoscope™ from BioRad with a molecular weight range of 250 kDa to 10 kDa) were electrophoresed according to standard conditions along with the plasma samples. The proteins were transferred to nitrocellulose membranes for Western blots analysis. The distance migrated of each molecular weight marker and the isoforms were measured and a graph was plotted with the logarithm of the molecular weight on the X-axis and the distance migrated on the Y-axis.
Figure 13:
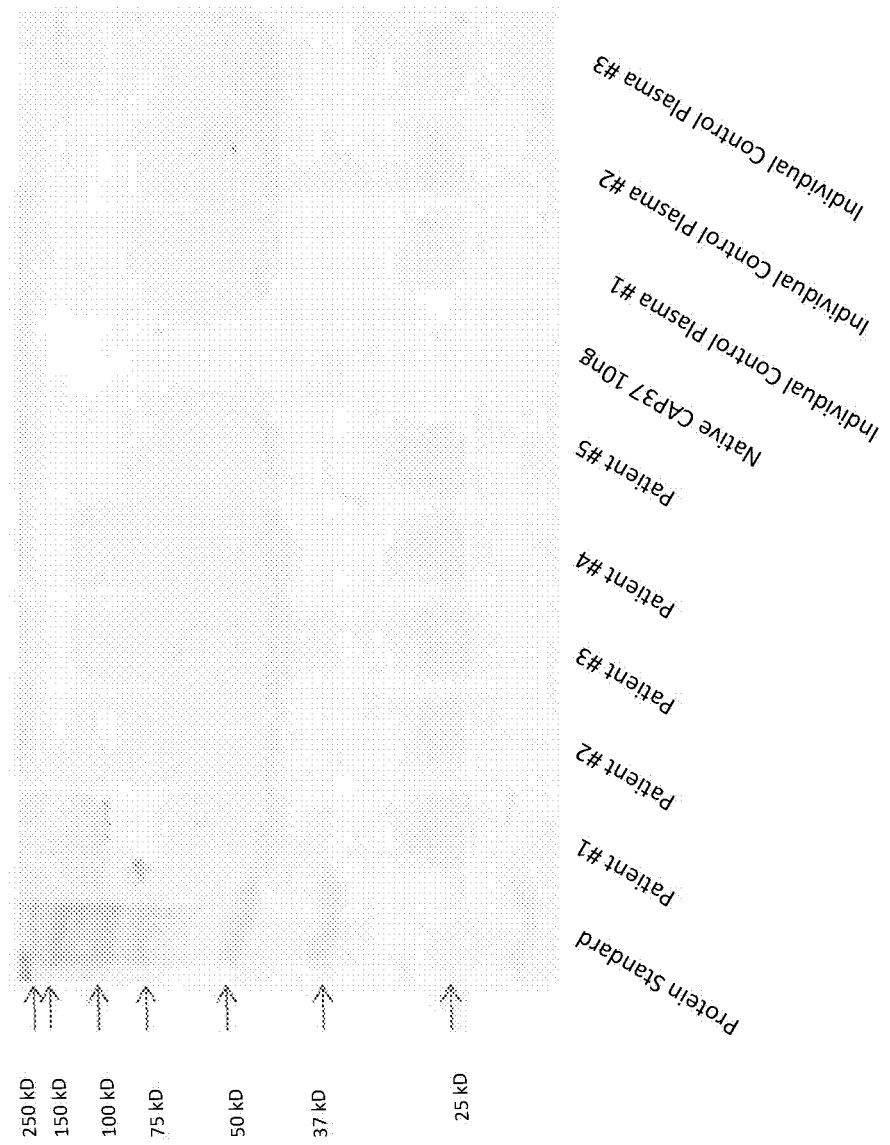
FIG. 13 is an image of a Western blot control which corresponds to the Western blot of FIG. 12 which uses normal rabbit IgG antibody.
Figure 14:
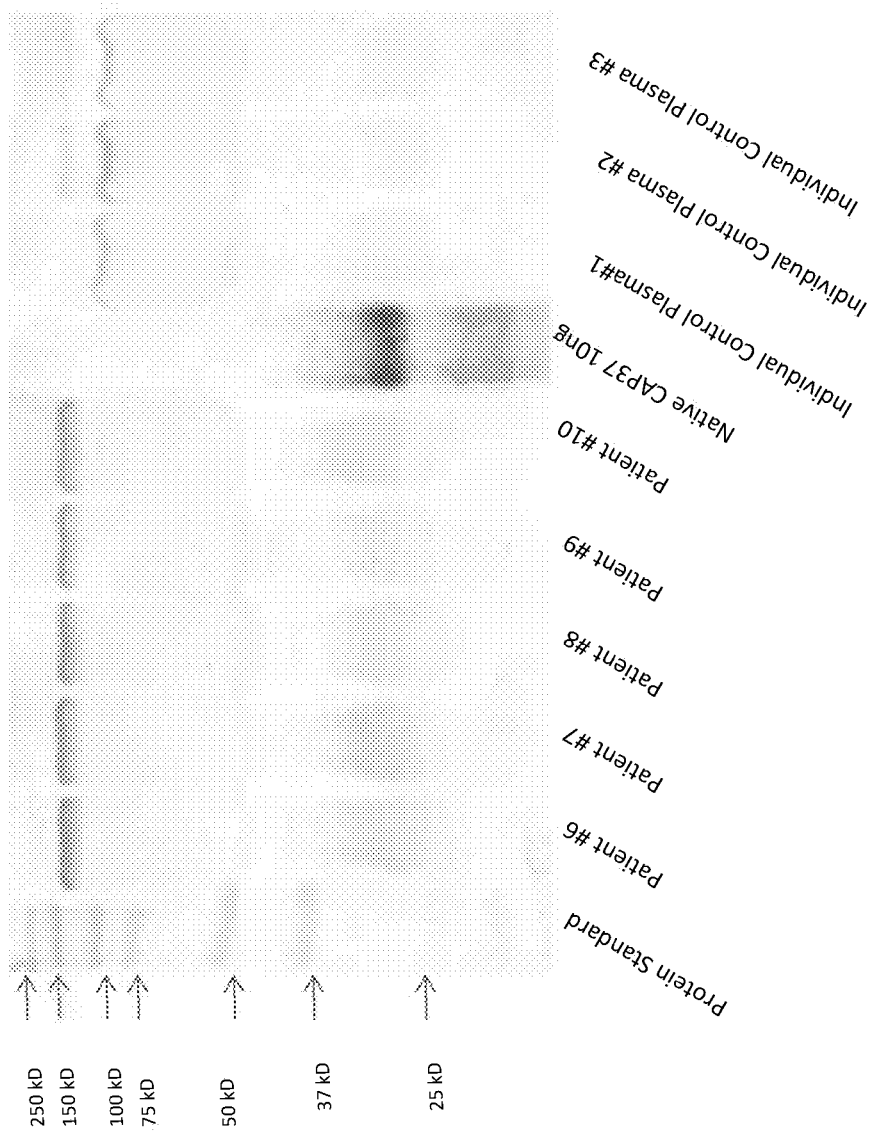
FIG. 14 is an image of a Western blot analysis of plasma samples from five additional patients diagnosed with osteoarthritis which shows the presence of a high molecular weight (~135 kDa) isoform of CAP37 protein in the plasma samples. The CAP37 isoform is captured by polyclonal rabbit anti-CAP37 IgG antibody (2.5 mg/ml, 1:50,000). Native CAP37 protein is shown in a band of about 28-37 kDa.
Figure 15:
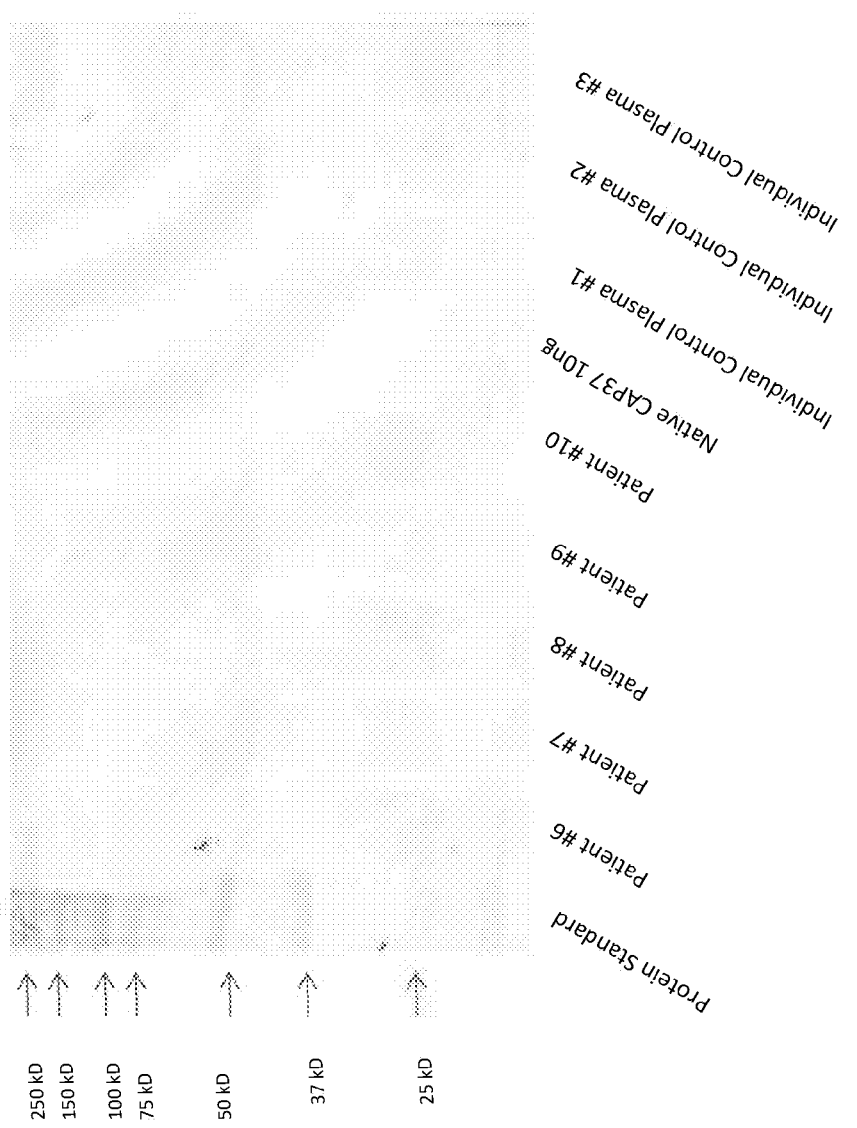
FIG. 15 is an image of a Western blot control which corresponds to the Western blot of FIG. 14 which uses normal rabbit IgG antibody.
Figure 16:
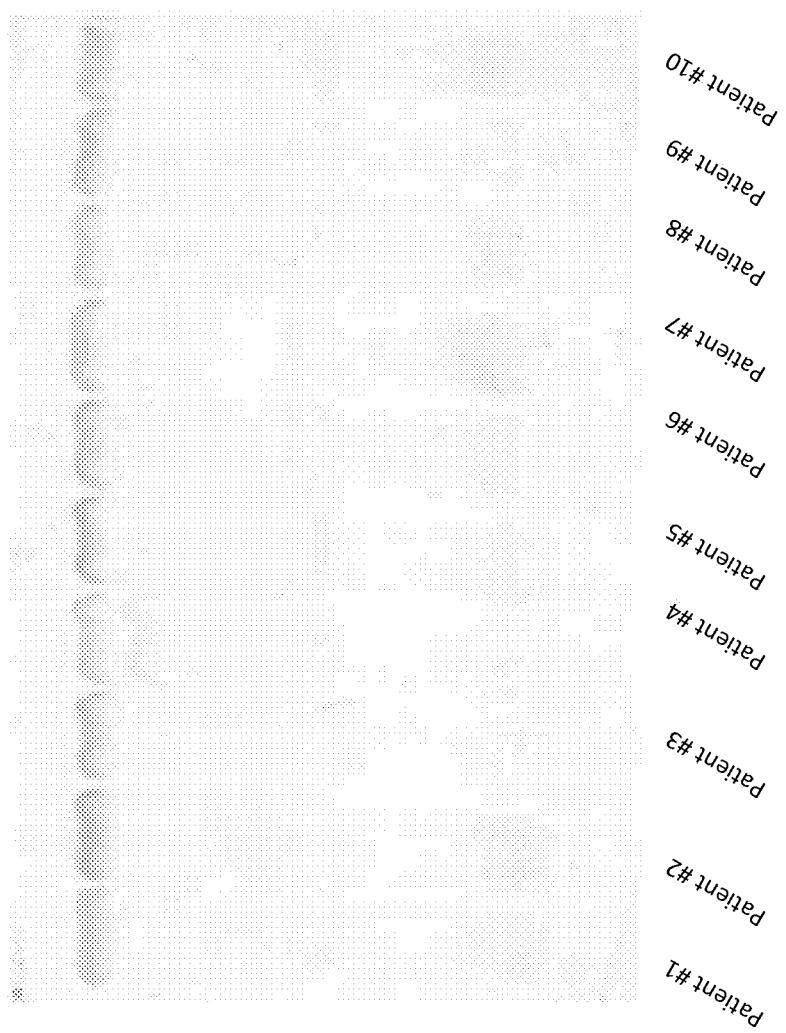
FIG. 16 is an image of a Western blot analysis showing the results for all 10 osteoarthritic patients of FIGS. 12 and 14 wherein the results showing the presence of the isoform is replicated.

Plasma samples from 10 patients who were diagnosed with osteoarthritis (and who did not have an active acute infection) were analyzed using SDS-PAGE under reducing conditions followed by Western blot analysis (using the techniques described previously). The only difference in the Western blot procedure of Examples 3 and 4 versus that used in Examples 1 or 2 was that the purified IgG fraction of the rabbit antibody to CAP37 was used, and was used at a much higher dilution (1:50,000) in the Western blots (wherein the prior blots used the primary antibody at 1:1,000). These samples were obtained from BioServe Biotechnologies Ltd, Beltsville, Md. These patients were also diagnosed with psoriasis, another chronic inflammatory-associated disease. "Control" plasma samples were taken from 3 individuals who were asked if they had an active acute infection (and answered negatively) but they were not explicitly asked if they had been diagnosed with osteoarthritis. Gels were loaded with patient samples and control samples and following electrophoresis were transferred to nitrocellulose for western blot analysis. The blots were probed with polyclonal rabbit anti-CAP37 IgG (2.5 mg/ml-1:50,000) (FIGS. 12, 14 and 16). The control western blots (FIGS. 13 and 15) were probed with normal rabbit IgG (0.2 mg/ml-1:4,000). The lack of reactivity in the control blots showed that the rabbit anti-CAP37 antibody was specific for CAP37. The results revealed strong bands corresponding to an apparent molecular weight (MW) of about 135 kDa (±15 kDa) in all ten osteoarthritis patients (FIGS. 12, 14 and 16). These bands constitute isoforms of CAP37 protein which are distinguished from polymorphonuclear (neutrophil-derived) CAP37 ("native CAP37" on the gels) which has a MW of 29-37 kDa, depending on its glycosylation level.

Control samples from individuals (C1, C2 and C3) in FIGS. 12 and 14, show a lower band comprising a CAP37 isoform having an apparent molecular weight of about 100 kDa (±15 kDa). One patient sample (P4) comprised this ~100 kDa isoform, and one individual control sample (P2) comprised the ~135 kDa isoform (indicating that this control individual may have some level of osteoarthritis or other chronic inflammatory-associated disease such as atherosclerosis).

Figure 17:
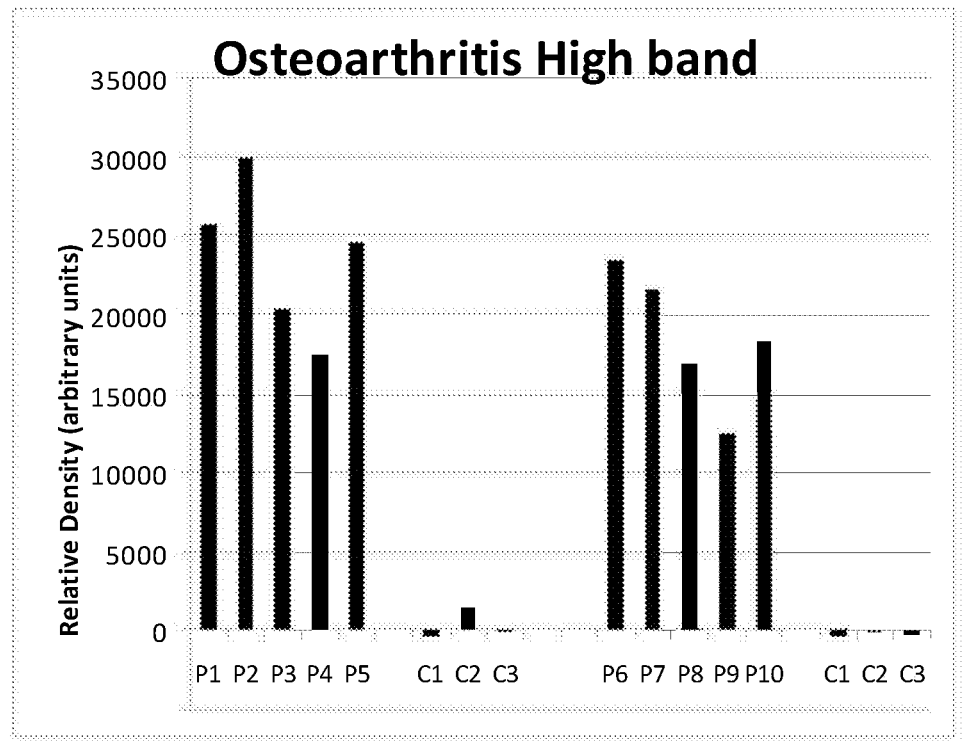
FIG. 17 are graphs showing densitometer readings in the relative units for the "high band" (~135 kDa) and "low band" (~100 kDa) results of FIGS. 12 and 14 for the 10 patients (P1-P10) and the three individual control samples ($C_1$-$C_3$).
Figure 17:
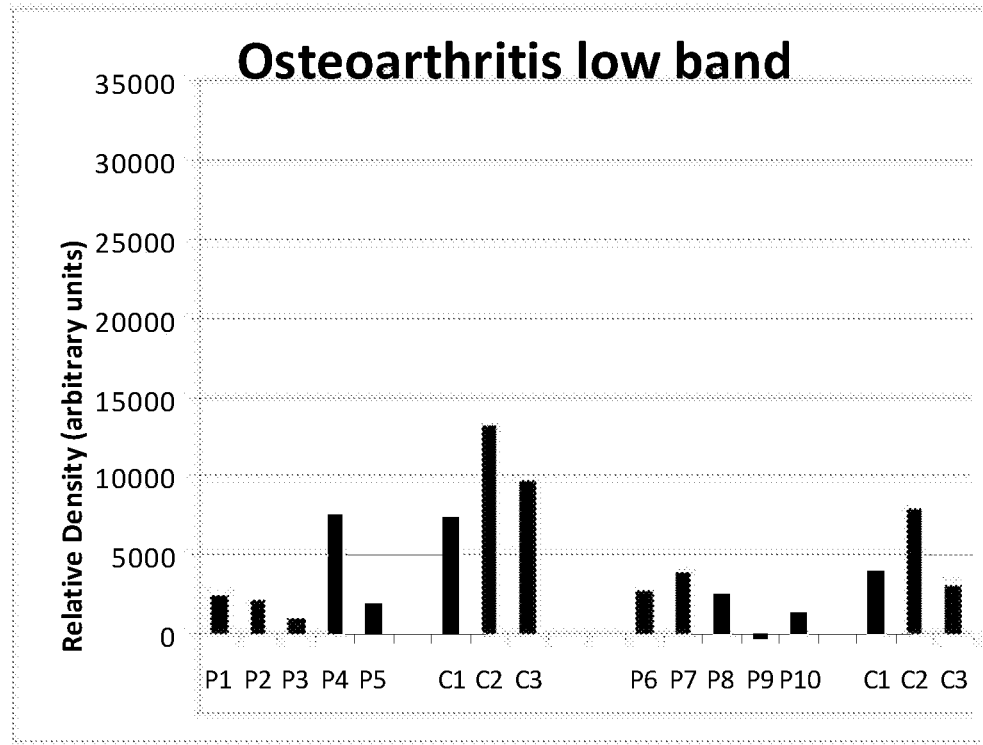

The data are summarized in FIG. 17 where it is shown that amounts of the ~135 kDa isoform ("High Band") in the patient samples (P1-P10) are substantially greater than any amounts of this isoform found in the control samples (C1-C3).

Normal rabbit IgG used for the Western blots came from Jackson ImmunoResearch Laboratories, Inc., WestGrove, Pa. The product is referred to in their catalog as ChromPure Rabbit IgG, whole molecule. The secondary antibody used in the Western blots also cam from Jackson ImmunoResearch Laboratories, Inc. The product is referred to as Alkaline Phosphatase-conjugated affiniPure Donkey anti-rabbit IgG (heavy and light chain). The primary antibody rabbit anti-CAP37 IgG was prepared in-house according to standard procedures.

Example 4

Atherosclerosis

Plasma samples from 9 patients who were diagnosed with atherosclerosis (and who did not have an active acute infection) were analyzed using SDS-PAGE under reducing conditions followed by Western blot analysis (using the techniques described previously for Example 3). These samples were obtained from Asterand, plc Detroit, Mich. Gels were loaded with the patient samples and the control samples and following electrophoresis were transferred to nitrocellulose for western blot analysis. The blots were probed with polyclonal rabbit anti-CAP37 IgG (2.5 mg/ml-1:50,000) (FIGS. 18, 20, 22 and 23). The control blots (FIGS. 19 and 21) were probed with normal rabbit IgG (0.2 mg/ml-1:4,000). The lack of reactivity in the control blots showed that the rabbit anti-CAP37 antibody was specific for CAP37. The results revealed strong bands corresponding to an apparent molecular weight (MW) of about 135 kDa (±15 kDa) in 6 of the 9 atherosclerosis patients (FIGS. 18, 20, 22 and 23). These bands, as for Example 3 above, constitute isoforms of CAP37 protein which are distinguished from polymorphonuclear (neutrophil-derived) CAP37 ("native CAP37" on the gels) which has a MW of 29-37 kDa, depending on its glycosylation level.

Figure 18:
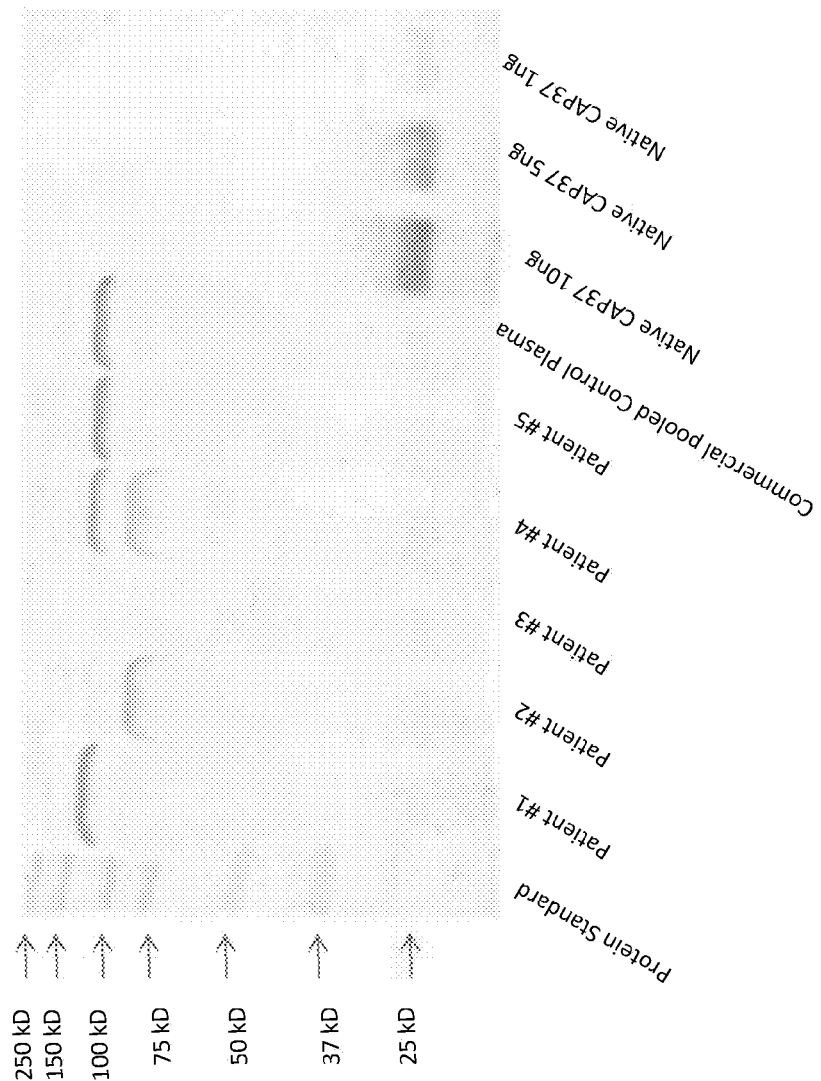
FIG. 18 is an image of a Western blot analysis of plasma samples from five patients diagnosed with atherosclerosis which show the presence therein of the high molecular weight isoform of CAP37 protein (~135 kDa) in the plasma samples of three of the five patients. The CAP37 protein isoform is captured as described above.
Figure 19:
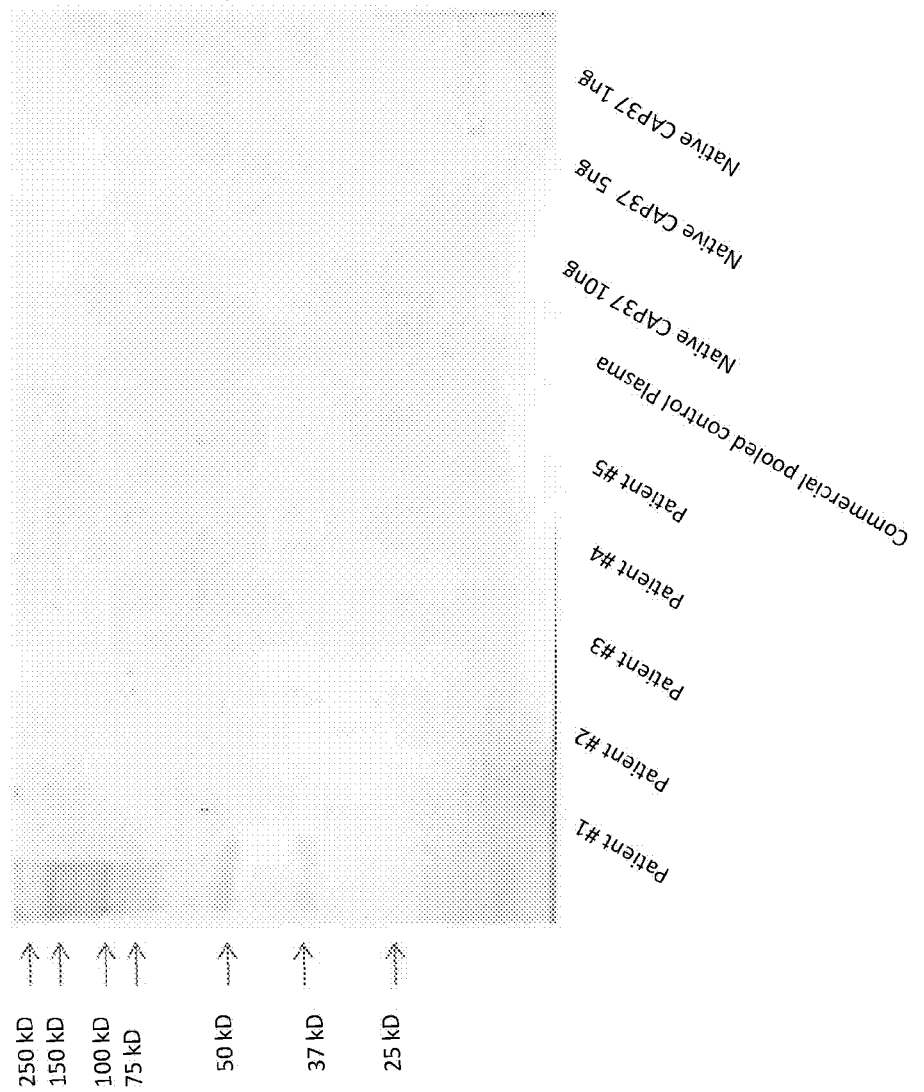
FIG. 19 is an image of a Western blot control which corresponds to the Western blot of FIG. 18 and which uses normal rabbit IgG antibody.
Figure 20:
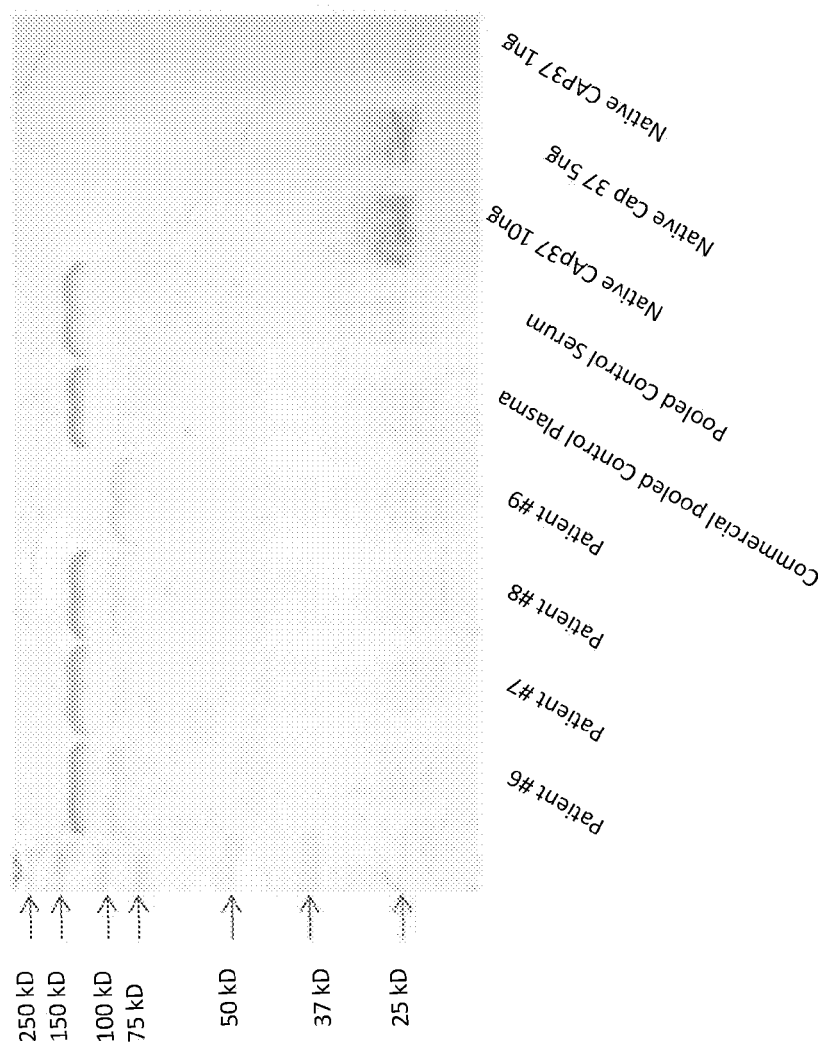
FIG. 20 is an image of a Western blot analysis of plasma samples from four additional patients diagnosed as atherosclerotic which shows the presence of the ~135 kDa CAP37 isoform in three of the four patient samples. Two "control" samples labeled as "Commercial Pooled Control Plasma" and "Pooled Control Serum" both show the presence of the ~135 kDa isoform and are suspected of being insufficiently characterized as to the source of the sample, that is, it is likely the two "control" samples may comprise plasma and serum from patients with a chronic inflammatory-related disease.
Figure 21:
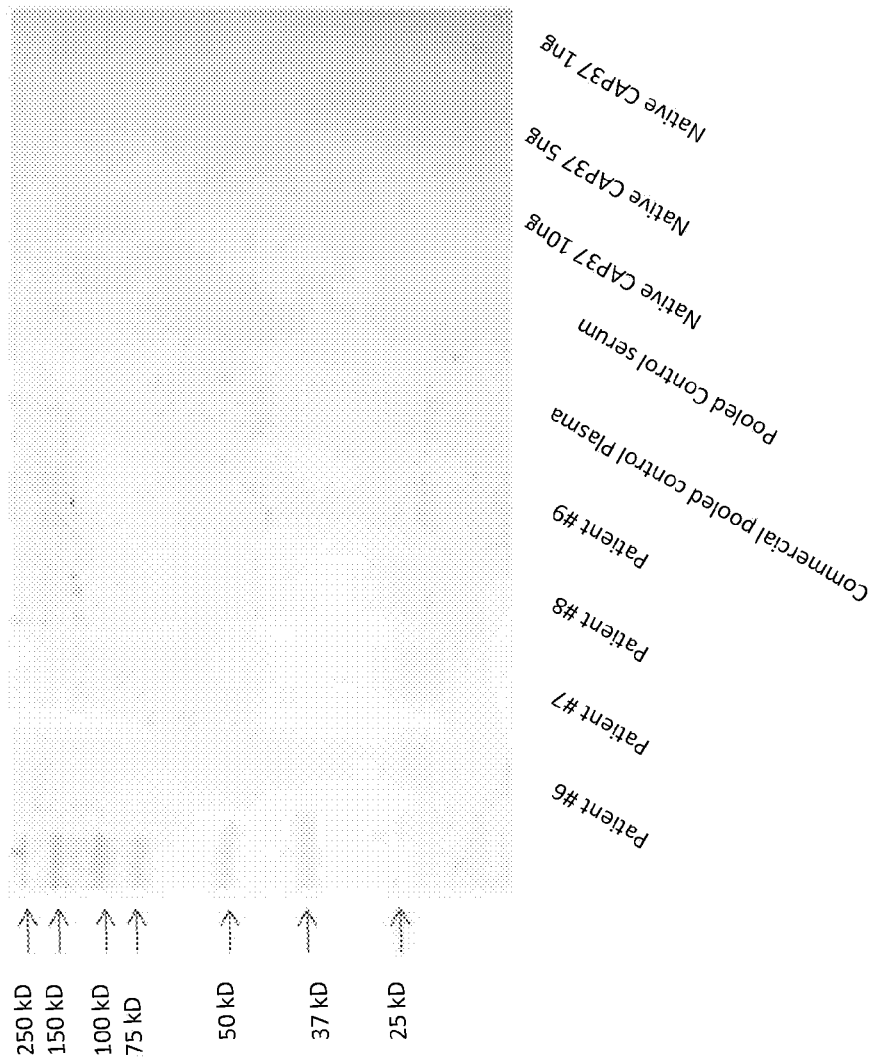
FIG. 21 is an image of a Western blot control which corresponds to the Western blot of FIG. 20 and which uses normal rabbit IgG antibody.

Samples from patients P2, P3 and P9 did not show bands of the ~135 kDa CAP37 isoform (FIGS. 18 and 20). It is suspected that these patients, who had previously been diagnosed with atherosclerosis had diminished levels of the ~135 kDa isoform due to treatment with an anti-inflammatory/immunosuppressive medication regime.

Two pooled control samples obtained from commercial sources in FIGS. 18 and 20 show an upper band comprising a CAP37 isoform having an apparent molecular weight of about 135 kDa (±15 kDa). These pooled samples were apparently not characterized as to whether or not they had a chronic inflammatory-associated disease. Thus at least one of the samples used in each pooled sample apparently had some level of a chronic inflammatory-associated disease such as atherosclerosis. These pooled control samples are thus suspect.

Figure 22:
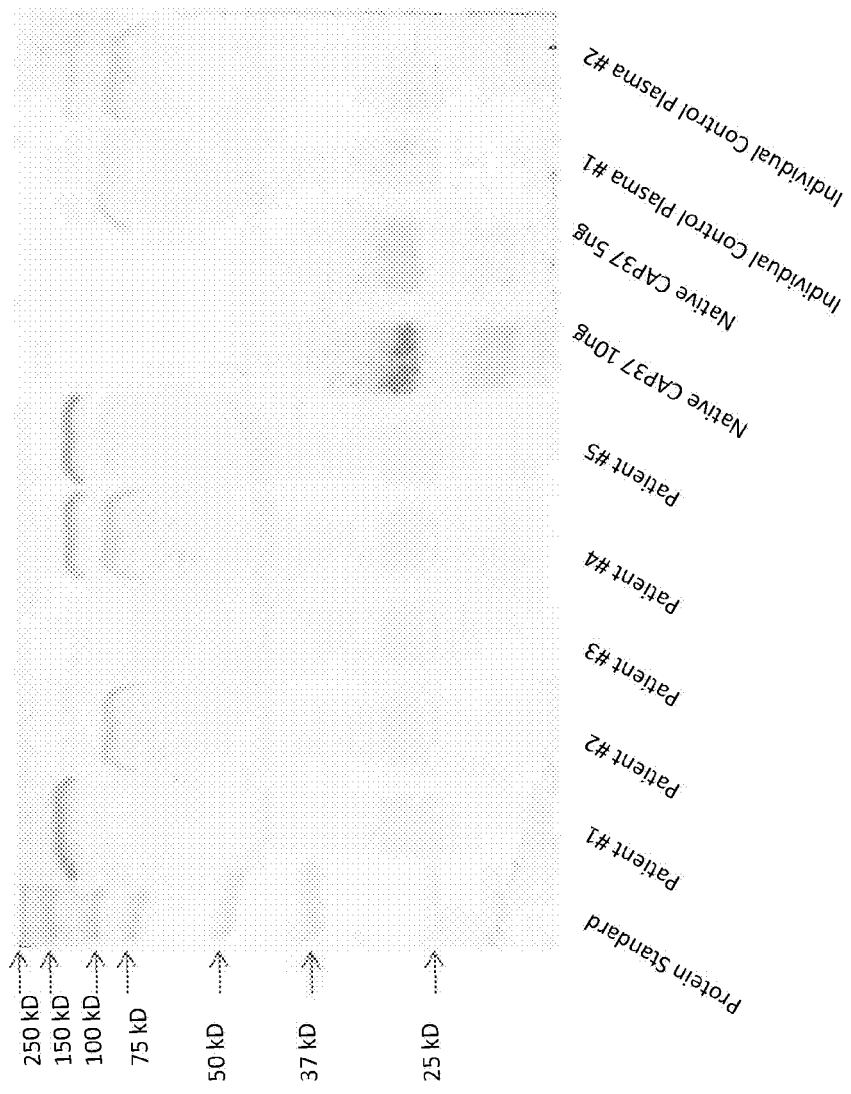
FIG. 22 is an image of a Western blot analysis which repeats the five patients from FIG. 18 against control plasma samples from two individuals. Only a faint amount of the ~135 kDa isoform of CAP37 protein appears in control sample 2 and none is apparent in control sample 1.
Figure 23:
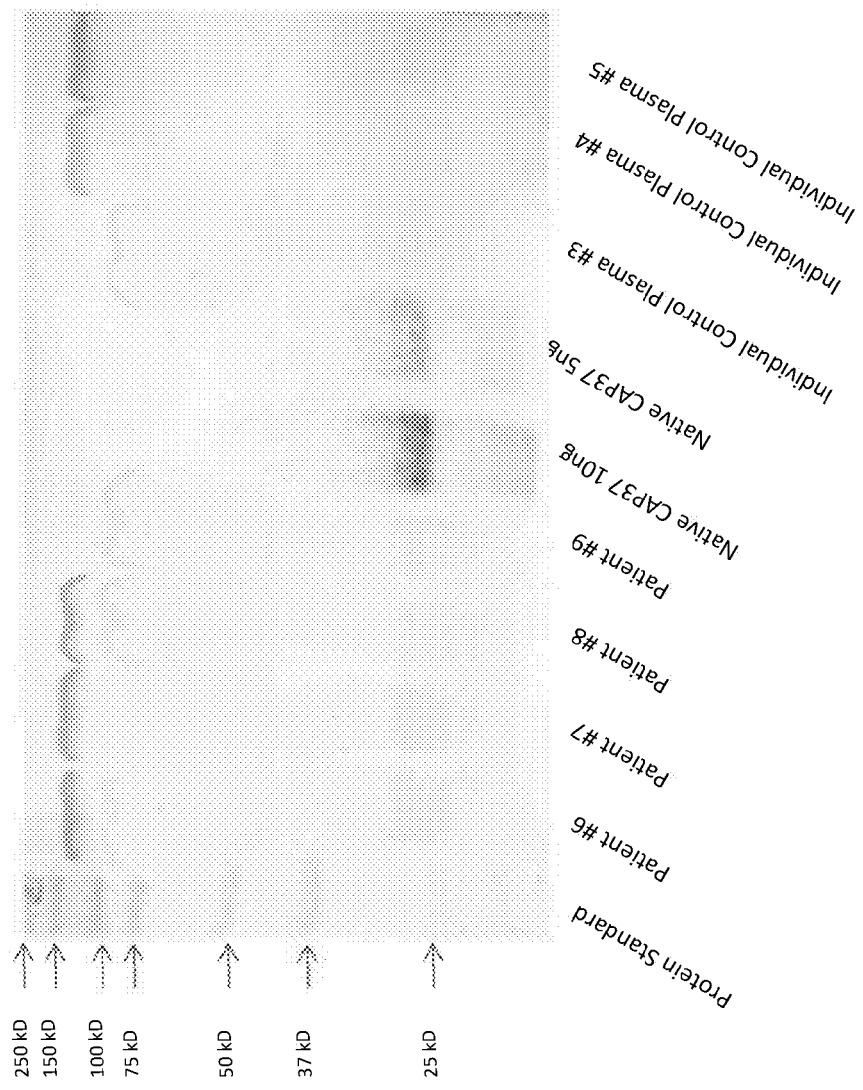
FIG. 23 is an image of a Western blot analysis which repeats the four patients of FIG. 20 against three additional control samples. Individual control sample No. 3 shows no visible amount of the ~135 kDa isoform while control samples No. 4 and No. 5 both show the presence of the ~135 kDa isoform. Again, control samples No. 4 and No. 5 were characterized only as to age (they were between 18 and 65 years of age) and not as to whether or not they had been diagnosed with a chronic inflammatory-associated disease (it is likely both suffered from a chronic inflammatory-associated disease, thus these samples are likely not true controls).

Five control samples (C1-C5) from individuals were analyzed (FIGS. 22 and 23). A slight amount of the ~135 kDa isoform was seen in the results for control sample C2 (FIG. 22). Dense bands for the isoform were present in the control samples C4 and C5. However, the disease history associated with these two controls was unknown. According to the research protocol of the study, no medical history could be asked, except for whether they had an active bacterial or viral infection. Samples were de-identified immediately and no identifiers were kept that could relate back to the sample according to the consenting protocol passed by the Institutional Review Board. It is likely that these two subjects had an undiagnosed or non-symptomatic chronic inflammatory-associated disease. These two control samples were thus suspect.

Figure 24:
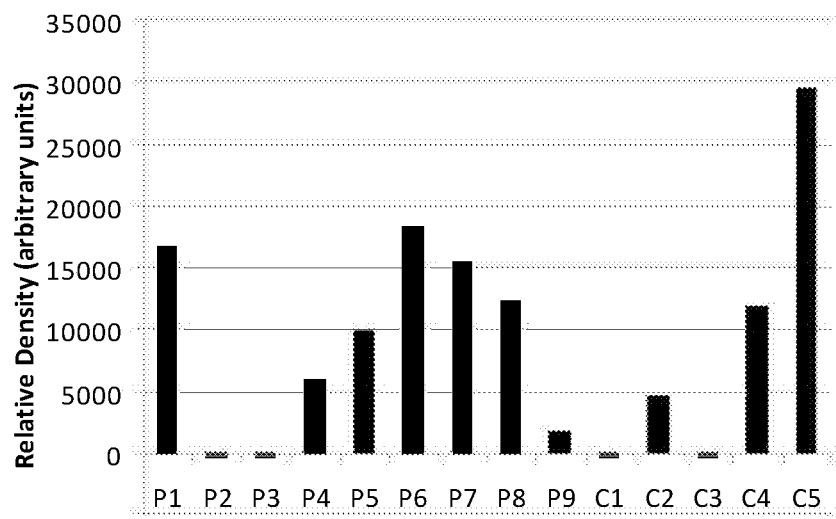
FIG. 24 are graphs showing densitometer readings in relative units for the ~135 kDa (high) and ~100 kDa (low) isoforms using the results from FIGS. 18, 20, 22 and 23.
Figure 24:
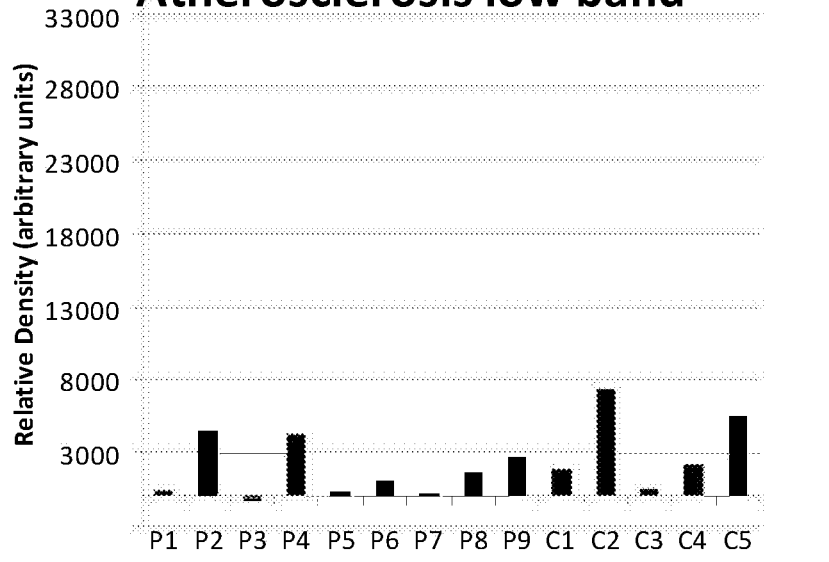

These data are summarized in FIG. 24 which show that the level of the ~135 kDa CAP37 isoform is substantially greater in the majority of the patient population studied as compared to a control population which comprised individual samples.

These data demonstrate that the isoform of CAP37 protein having a MW of ~135 kDa is consistently present in patients who suffer from a chronic inflammatory-associated disease such as osteoarthritis or atherosclerosis. In one embodiment, a subject is considered to have a chronic inflammatory-associated disease such as osteoarthritis or atherosclerosis if a plasma or serum sample therefrom comprises the ~135 kDa isoform of CAP37 protein, or has at least twice (2×) the amount calculated as an average of said isoform found in a control population.

Utility

In one embodiment, the presently disclosed and claimed inventive concept(s) is directed to a novel anti-CAP37 monoclonal antibody or binding fragment thereof, as well as a hybridoma for producing such antibody or fragment. Another embodiment of the presently disclosed and claimed inventive concept(s) is directed to a method of producing any of the monoclonal antibodies of fragments thereof as described or otherwise contemplated herein, by culturing a cell capable of expressing the monoclonal antibody/fragment (such as but not limited to, any of the hybridomas described herein) under conditions that permit production of the monoclonal antibody or antigen binding fragment thereof. Yet another embodiment of the presently disclosed and claimed inventive concept(s) is directed to a method of detecting, in a subject, a chronic inflammatory-associated disease, such as Alzheimer's disease. The method comprises (1) obtaining a fluid sample from the subject, (typically the subject does not have an acute bacterial or viral infection when the fluid sample is obtained), (2) testing the fluid sample for an isoform of CAP37 protein (a biomarker) for example by using a CAP37-specific monoclonal antibodies (e.g., D5F10 or B1B5) in an ELISA or Western blot test for example, and (3) concluding that the subject has a chronic inflammatory-associated disease when an isoform of CAP37 protein having an apparent molecular weight of about 135 kDa (or another CAP37 isoform as described herein) is detected in the fluid sample. The fluid sample may comprise serum, plasma, or cerebrospinal fluid, for example, or any other body fluid exposed to endothelial, vascular, or neuronal secretions. In certain embodiments, the chronic inflammatory-associated disease is selected from the group consisting of atherosclerosis, Alzheimer's disease, asthma, rheumatoid arthritis, osteoarthritis, and inflammatory diseases of the bowel such as Crohn's disease, Ulcerative colitis, Irritable bowel syndrome and Inflammatory bowel disease, as well as any combination of the above. The CAP37 isoform may be endothelial CAP37, vascular CAP37, neuronal CAP37, or neutrophil-derived, for example. The isoform of CAP37 protein (characterized elsewhere herein according to molecular weight) comprises at least a portion of the protein having the amino acid sequence identified herein as SEQ ID NO: 8.

The use of CAP37 as an early marker for detection of inflammatory associated diseases can be used in concert with medical symptoms associated with a given disease. For example, CAP37 as an early marker of atherosclerosis would be determined in patients at risk for heart disease having one or more risk factors including smoking, obesity, family history, chest pain and/or diabetes. CAP37 as an early marker of Alzheimer's disease would be determined in patients at risk for this disease which would include the elderly, changes in cognitions, and in persons with a family history of Alzheimer's disease. CAP37 as an early marker for asthma would be indicated in adults and children with associated symptoms of wheezing, shortness of breath and allergic reactions, for example. CAP37 as an early marker of osteoarthritis and or rheumatoid arthritis would be best determined in patients presenting swollen joints, pain in joints or stiffness in joints, for example. CAP37 as a marker of inflammatory diseases of the bowel would be best determined in patients with changes in bowel habits, extended periods of discomfort, acid reflux, bloating, and cramping and other symptoms typical of persons with inflammatory diseases of the bowel.

Plasma for use in a diagnostic test can be obtained, for example, by collecting peripheral venous blood (approximately 5 ml) from a subject by venipuncture into a sterile tube containing EDTA or sodium citrate. EDTA and sodium citrate serve as anticoagulants and stop the blood from clotting. The anti-coagulated blood may be centrifuged at the regulation speed of 1500 r.p.m. for 10 min. This permits the cellular components of the blood to settle to the bottom of the tube. The plasma can be aspirated from the top of the tube and used immediately in the assay or can be stored indefinitely in sterile tubes at −20° C. for later analysis.

Serum can be obtained, for example, by collecting peripheral venous blood (e.g., approximately 4 ml) by venipuncture into a sterile tube without any anticoagulant. The tube may be stored at room temperature until the blood clots. The tube can be centrifuged at 1500 r.p.m. for 10-15 min. The straw colored liquid on top of the clot is the serum. The serum is aspirated and can be used immediately in the assay or can be stored indefinitely at −20° C. for future analysis. Any trained phlebotomist, technician, nurse, or physician can perform the venipuncture, for example.

Cerebrospinal fluid can be collected by standard practice generally known as a spinal tap by an authorized health practitioner. The spinal fluid (for example, approximately 2-4 ml) can be used immediately in the assay or may be aliquoted and stored at −20° C. for later analysis.

The neuronal CAP37, endothelial CAP37, vascular CAP37, and neutrophil-derived CAP37 isoforms can be detected from the fluid sample using CAP37-specific monoclonal or polyclonal antibodies, such as described elsewhere herein, e.g., D5F10 or B1B5, in a standard ELISA method well known to those of ordinary skill in the art, for example, as described in Pereira et al., 1989 (30) which is expressly incorporated herein by reference in its entirety, or the neuronal CAP37, endothelial CAP37, or vascular CAP37 may be detected by any other suitable method known in the art, for example PCR, as described elsewhere herein. Rabbit antisera and mouse antisera which are specific for CAP37 can be prepared using standard methods well known to those of ordinary skill in the art, for example, as in Pereira et al., 1996a (11) and Pereira et al., 1996b (13) which are expressly incorporated herein by reference in their entirety.

In another embodiment, the presently disclosed and claimed inventive concept(s) comprises a method of making an early prediction of the occurrence of an acute inflammatory response in a subject (patient) due to an infection such as sepsis or other severe acute bacterial infection. In the method, a fluid sample is taken from a patient suspected of having such an infection, or susceptible to having such an infection, for example a hospitalized patient or a patient who has undergone a surgery or other procedure associated with or prone to causing systemic bacterial infections. The fluid sample is tested for CAP37 protein isoform such as neutrophil-derived CAP37 by binding the protein with a CAP37-specific monoclonal antibody such as D5F10 or B1B5. When CAP37 protein is detected in the fluid sample, it is predicted that the patient will have sepsis or a severe acute inflammatory response due to bacterial infection. Further, the result can be used to distinguish an acute inflammatory response which is due to a bacterial infection from one due to non-infectious causes, particularly in patients in which it is either too early to obtain accurate microbiological or bacteriological culture data or wherein treatment decisions must be made before results from such cultures can be obtained. The acute inflammatory response associated with the positive result for CAP37 protein could also be due to acute lung injury or acute respiratory distress syndrome in those individuals having severe acute pulmonary conditions. The present method may be particularly used in patients in Intensive Care Units (ICU) wherein rapid diagnosis is of critical importance. Further, the test may be used in tandem with detection or measurement of another inflammatory marker, such as, but not limited to, C-reactive protein, IL-1, IL-6, or tumor necrosis factor alpha, to improve the predictability of the method.

As discussed above, in a particular embodiment, the presently disclosed and claimed inventive concept(s) comprises isoforms of CAP37 protein (e.g., the ~135 kDa, ~100 kDa, ~46 kDa, ~40 kDa, ~33 kDa, and ~27 kDa isoforms) which may be used as biomarkers or to generate monoclonal antibodies against the CAP37 isoform protein described herein using methods well known in the art, which may be used in assays used in the detection method as described herein. Such antibodies against the isoforms of CAP37 protein are also considered to be embodiments of the presently disclosed and claimed inventive concept(s) as claimed herein. The isoforms may also be used in screening methods for identifying inhibitors of these proteins. The presently disclosed and claimed inventive concept(s) further comprises nucleic acids, e.g., cDNAs which encode the endothelial CAP37 protein isoforms, vascular CAP37 protein isoforms, neutrophil-derived CAP37 isoforms, and neuronal CAP37 protein isoforms. The presently disclosed and claimed inventive concept(s) further comprises those amino acid portions of the endothelial CAP37, vascular CAP37, neuronal CAP37, or neutrophil-derived CAP37 proteins which do not comprise SEQ ID NO:8, i.e., the N-terminal or C-terminal portions extending N-terminally and/or C-terminally from SEQ ID NO:8.

Examples of diagnostic kits and tests for identifying the endothelial CAP37 protein isoforms in fluid samples include, but are not limited to, the examples described below.

1) Western blot test to determine the presence of the CAP37 isoform in plasma, serum, or other body fluid.

A mono-specific rabbit antibody to the CAP37 isoform or a mouse monoclonal antibody to the CAP37 isoform is produced according to standard protocols. To produce the monoclonal and/or polyclonal antibody, the band corresponding to the CAP37 isoform can be cut out of the gel, homogenized and used as the "antigen" to immunize rabbits or mice. The standard protocol for generating polyclonal monospecific antiserum in rabbits is utilized or the standard protocols for generating monoclonal antibodies in mice are utilized. The preparation of polyclonal or monoclonal antibodies is conventional and well known to persons of ordinary skill in the art. Alternatively, the protein can be purified according to standard Reverse phase HPLC protocols to separate the CAP37 isoform from the plasma of patients. The purified protein can be used to generate the antibodies in rabbits or mice. The test comprises providing the purified CAP37 isoforms at a known concentration and the corresponding purified antibody that reacts specifically with the CAP37 isoform and of performing standard SDS-PAGE gel electrophoresis of the patient samples and the known CAP37 isoform control protein. Samples are transferred to nitrocellulose or PVDF membranes and western blot performed using the primary antibody to the CAP37 provided with the kit. Various options from commercial vendors are available for use as secondary antibodies. These include antibodies that could be used with chemiluminescence or the blots can be developed using secondary antibodies conjugated to alkaline phosphatase or other standard enzymatic reactions. Reaction with the antibody at a band corresponding in molecular weight to the known control indicates the presence of the corresponding CAP37 isoform in the patient sample.

2) ELISA to determine the presence of CAP37 isoform in plasma, serum or other body fluid.

Monoclonal antibody and polyclonal rabbit antisera is produced as above. The purified CAP37 isoform is also obtained as above. A sandwich ELISA uses the mouse monoclonal antibody as a capture antibody and the rabbit antiserum as a detection antibody (as described elsewhere herein). A standard curve can include the purified CAP37 isoform in a dose range from 0-200 ng/ml, for example. The patients' plasma is added undiluted or diluted at 1:4, for example, and the ELISA is developed according to standard protocols. The amount of CAP37 isoform present in the patients sample is determined from the values obtained on the standard curve.

By purifying the CAP37 isoform and making antibodies that are specific to this large molecular weight band, the test is specific for this isoform and does not detect the neutrophil-derived CAP37 protein which is found at a molecular weight range of 29-37 kDa. As used herein, the "affinity" of an antibody for a CAP37 isoform is characterized by its $K_d$, or disassociation constant. A stronger affinity is represented by a lower $K_d$ while a weaker affinity is represented by a higher $K_d$. As such, an antibody of the presently disclosed and claimed inventive concept(s) may have an affinity for its corresponding antigen represented by a $K_d \leq 100$ nM, or $\leq 50$ nM, or a $K_d \leq 25$ nM, or a $K_d \leq 10$ nM, or a $K_d \leq 5$ nM.

Figure 25:
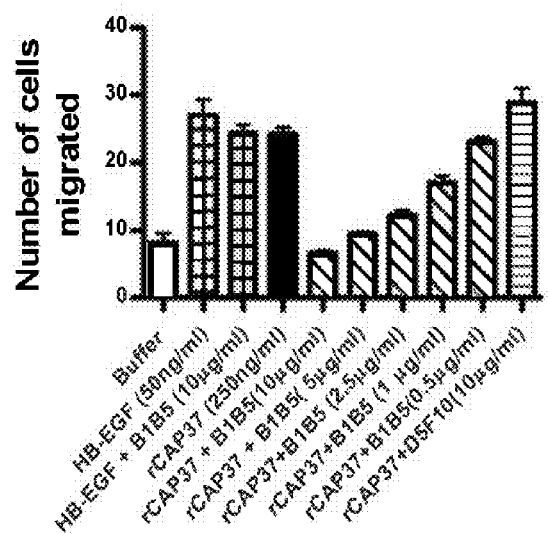
FIG. 25 illustrates the inhibition of HCEC migration in response to CAP37 using monoclonal antibodies to CAP37. Chemotaxis was performed using 250 ng/ml of rCAP37 and heparin-binding—epidermal growth factor (HB-EGF, 50 ng/ml). Monoclonal antibody B1B5 was used at 0.5-10 µg/ml and monoclonal antibody D5F10 at 10 µg/ml to inhibit migration. Dose response inhibition was significant with B1B5 at 2.5-10 µg/ml. D5F10 did not inhibit migration. Data are mean±SEM of three independent experiments performed in triplicate.
Figure 26:
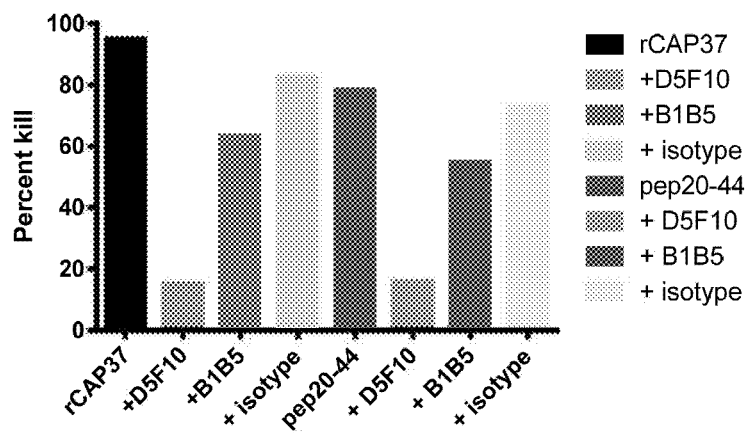
FIG. 26 shows the inhibitory effect of MAb D5F10 and MAb B1B5 on the bactericidal function of CAP37 and on the bactericidal function of peptide 20-44. *Salmonella typhimurium* SH 9178 was exposed to rCAP37, to rCAP37 incubated with MAb D5F10, to rCAP37 incubated with MAb B1B5 and to rCAP37 incubated with mouse isotype control. This figure represents the average of two independent experiments. *p<0.05 by the Student t-test for unpaired data.

In another embodiment of the presently disclosed and claimed inventive concept(s), the novel antibody B1B5 or binding fragments thereof (such as humanized versions) can be administered to a subject to inhibit, reduce, mitigate, or otherwise modulate the effect of endogenous CAP37 on the migration, activation, and/or proliferation of monocytes, microglia, smooth muscle cells, and corneal epithelial cells in vivo (see FIGS. 25 and 26). The activation and migration of monocytes and smooth muscle cells plays a key role in the development of atherosclerotic plaques. By blocking CAP37 the activation and migration of monocytes and smooth muscle cells can be reduced thereby delaying the progression of atherosclerosis. B1B5 antibody can also be used to block CAP37 from activating microglia, thereby dampening the activation of microglia in the brain thereby slowing down the progression of a disease such as AD. B1B5 therefore can be used to stop or dampen a deleterious effect of chronic inflammation that involves cells such as monocytes, smooth muscle cells, microglia and corneal epithelial cells. As noted, typically humanized B1B5 antibodies or antigen-binding fragments thereof are used.

The antibody or binding fragment thereof can be administered to the subject in any suitable dosage such as, but not limited to, 1-1000 mg/adult dose, or approximately 0.015-15 mg/kg per dose or per daily dosage. The dosage may be provided in single or multiple doses. The amount will vary depending on age, weight, and severity of the condition and will be selected by the attending physician or other person of skill in the art. The dosage may be provided orally, parenterally, intravenously, or by any other suitable method.

Figure 27:
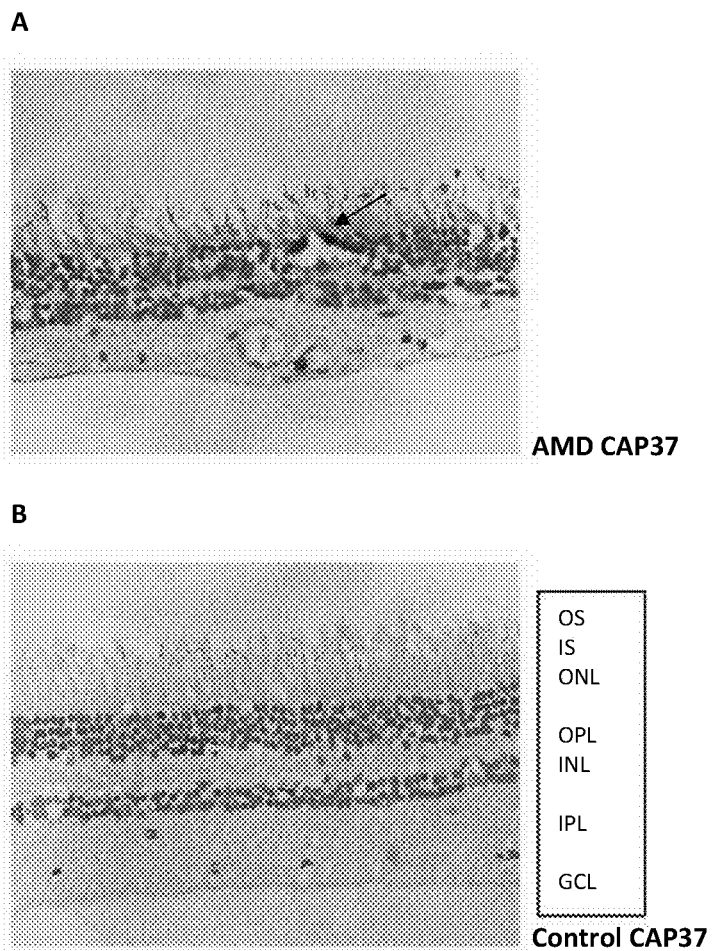
FIG. 27 illustrates CAP37 localization in the retina of subjects with Age-Related Macular Degeneration (AMD). (A) AMD patient, (B) Normal age-matched control. Paraffin embedded sections were stained using the HiDefDetection™ Polymer System (Cell Marque). A) AMD section stained with anti-CAP37 mouse monoclonal antibody D5F10. Note staining that occurs primarily within the photoreceptor inner segments (black arrows). B) Age-matched control stained with anti-CAP37 mouse monoclonal antibody D5F10. Pictures were taken at ×400 magnification. OS; photoreceptor outer segment, IS; photoreceptor inner segment, ONL; outer nuclear layer, OPL; outer plexiform layer, INL; inner plexiform layer, IPL; inner plexiform layer, GCL; ganglion cell layer.
Figure 28:
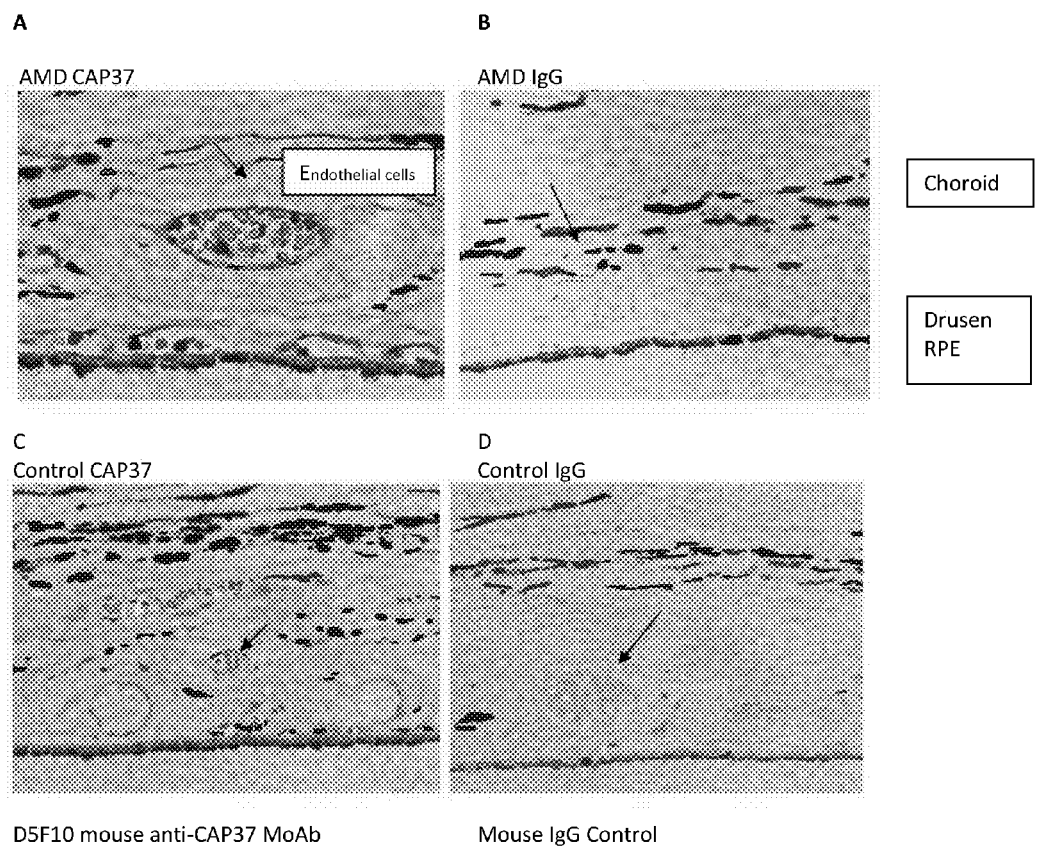
FIG. 28 shows the localization of CAP37 in RPE and Choroid of subjects with AMD. (A-B) AMD patient, (C-D) Normal age-matched control. Paraffin Embedded sections were stained using the HiDef Detection Polymer System (Cell Marque). A) AMD Retinal Pigment Epithelium (RPE) and overlaying drusen and choroid stained with anti-CAP37 mouse monoclonal antibody. Note the staining that occurs within the endothelial cells lining the choroid vessels (arrow). B) AMD section stained with Mouse IgG control. Note absence of staining of the choroid vessels. C) Age-matched control stained with anti-CAP37 mouse monoclonal antibody. Note the intact Bruch's membrane and absence of drusen and choroid vessels staining. D) Age-matched control stained with Normal Mouse IgG control antibody. Pictures were taken at X400 magnification.

In one embodiment of the presently disclosed and claimed inventive concept(s), the novel antibodies or binding fragments thereof can be used to detect Age-Related Macular Degeneration (AMD) in the eyes of a subject. CAP37 protein has been found to be present in the photoreceptor inner segments of the eye (FIG. 27) and in the choroid and retinal pigment epithelium (FIG. 28). Anti-CAP37 antibodies such as D5F10 and B1B5 can be labeled, for example with $^{18}$F or other labels described herein and administered topically, intravitreally, intravenously, or by other suitable routes, into a subject to be assessed for AMD. The eyes of the subject can be examined by PET scanning or MRI or other suitable method known to those of ordinary skill in the art for the presence of the labeled antibodies in the eye, which would indicate the existence of AMD in the subject.

In another embodiment of the presently disclosed and claimed inventive concept(s), the novel antibodies or binding fragments thereof can be used to diagnose Alzheimer's disease (AD) in a subject by administering a labeled anti-CAP37 antibody (e.g., D5F10 or B1B5) and examining the brain of the subject for the presence of CAP37 protein via an imaging method such as described herein, for example, PET or MRI. The presence of beta amyloid may also be assessed by using a drug which targets beta amyloid such as Amyvid® or Fluorbetapir$^{18}$F®. In a case wherein the subject is positive for both CAP37 and beta amyloid in the brain, a diagnosis of an advanced case of AD can be made, while in a case in which CAP37 is determined to be present in the retina but is not present in the brain, the subject can be diagnosed as having an early stage of AD.

In another embodiment of the presently disclosed and claimed inventive concept(s), the novel antibody D5F10 and/or B1B5 or binding fragments thereof can be used in an assay to monitor disease progression and treatment effectiveness, that is, to determine how well a particular therapeutic is working. CAP37 is a mediator released in many acute and chronic infections, therefore by monitoring the levels of the CAP37 protein in blood, plasma, CSF, urine or other tissue samples, a decrease in the levels of CAP37 would be an indication that the inflammatory situation was in remission or was being successfully treated by the therapeutic. This would indicate success for a particular treatment of, for example, sepsis, an acute inflammation, or a chronic inflammation. Alternatively, in the event levels of CAP37 did not decrease (i.e., remained constant or increased), it would be an indication that the particular treatment was not working effectively and that an alternative treatment should be considered.

In certain embodiments, the presently disclosed and claimed inventive concept(s) is directed to isolated antibodies or antigen-binding fragment thereof, which specifically bind to an epitope of CAP37 protein, wherein the isolated antibody is designated as D5F10 or B1B5. The isolated monoclonal antibody or antigen-binding fragment may comprise a light chain variable region CDR1, CDR2, and CDR3 of at least one of monoclonal antibody D5F10 and monoclonal antibody B1B5; and a heavy chain variable region CDR1, CDR2, and CDR3 of at least one of monoclonal antibody D5F10 and monoclonal antibody B1B5. The isolated monoclonal antibody or antigen-binding fragment thereof may be a full length immunoglobulin molecule, an scFv, a Fab fragment, an Fab' fragment, an F(ab')2, an Fv, a disulfide linked Fv, and combinations thereof. The isolated monoclonal antibody or antigen binding fragment thereof may be humanized. The isolated monoclonal antibody or antigen binding fragment thereof may bind to the CAP37 epitope with a dissociation constant of less than or equal to about $10^{-7}$ M. In another embodiment, the presently disclosed and claimed inventive concept(s) includes a pharmaceutical composition comprising the monoclonal antibody or antigen-binding fragment thereof described herein and a pharmaceutically acceptable carrier. In another embodiment, the presently disclosed and claimed inventive concept(s) is directed to a hybridoma which produces monoclonal antibody D5F10 or B1B5, or to and isolated nucleic acid molecule encoding at least one CDR of a light chain variable region or heavy chain variable region of at least one of monoclonal antibody D5F10 and monoclonal antibody B1B5.

In another embodiment, the presently disclosed and claimed inventive concept(s) is directed to a method of diagnosing inflammation and neuronal damage in the brain of a subject, comprising (1) administering a labeled CAP37-specific antibody or labeled binding fragment thereof to the subject and (2) using a brain imaging technique to assess the brain for the presence of the labeled CAP37-specific antibody or labeled binding fragment in the cortical and hippocampal areas of the brain, wherein presence of the labeled CAP37-specific antibody or labeled binding fragment in the cortical and hippocampal areas of the brain indicates a diagnosis of inflammation and neuronal damage in the brain. The labeled CAP37-specific antibody may be D5F10 or B1B5 or a binding fragment thereof. The diagnosis may indicate Alzheimer's disease in the subject. The determination of presence of the labeled CAP37-specific antibody or labeled binding fragment may be made when the imaging technique detects at least two areas of labeled CAP37-specific antibody or labeled binding fragment in the cortical and hippocampal areas of the brain. The diagnosis of Alzheimer's disease may be made for the subject when the brain is positive for both (1) the labeled CAP37-specific antibody or labeled binding fragment and (2) beta amyloid and/or tau protein.

In another embodiment, the presently disclosed and claimed inventive concept(s) is directed to a method of detecting Alzheimer's disease in a subject suspected of having Alzheimer's disease, comprising: (1) analyzing a serum, plasma, cerebrospinal fluid sample obtained from the subject to detect an isoform of neuronal CAP37 protein in the sample, wherein the isoform of neuronal CAP37 protein is isolated by binding to at least one of monoclonal antibody D5F10 and B1B5; and (2) correlating the detection of the neuronal isoform of CAP37 protein with the presence of Alzheimer's disease in the subject. The presence of the isoform of the neuronal CAP37 protein may be correlated with the presence of Alzheimer's disease in the subject when the isoform of the neuronal CAP37 protein is present in an amount which is at least twice an amount of the isoform calculated as an average of said isoform found in a control population.

In another embodiment, the presently disclosed and claimed inventive concept(s) is directed to a method of detecting Age-Related Macular Degeneration (AMD) in a subject suspected of having AMD, comprising administering a labeled CAP37-specific antibody or binding fragment thereof to the subject and assessing the eye for the presence of the labeled CAP37-specific antibody or binding fragment in the choroid, retinal pigment epithelium, or photoreceptor inner segment of the eye, wherein presence of the labeled CAP37-specific antibody or binding fragment in the choroid, retinal pigment epithelium, or photoreceptor inner segment of the eye indicates a diagnosis of AMD. The labeled CAP37-specific antibody may be D5F10 or B1B5 or a binding fragment thereof.

In another embodiment, the presently disclosed and claimed inventive concept(s) is directed to an isolated protein, comprising an isoform of CAP37 protein having an apparent molecular weight, as assessed by SDS PAGE under reducing conditions, selected from the group consisting of about 27 kDa, 33 kDa, 40 kDa, 46 kDa, 100 kDa±15 kDa, and 135 kDa±15 kDa. In another embodiment, the presently disclosed and claimed inventive concept(s) is directed to a therapeutic method of using at least one of (1) monoclonal antibody D5F10, (2) monoclonal antibody B1B5, and (3) an antigen-binding fragment of either of monoclonal antibodies D5F10 or B1B5, to inhibit, mitigate, or modulate at least one cellular activity involving CAP37 protein, wherein the at least one cellular activity involving CAP37 protein is selected from the group consisting of cell migration, cell activation, and cell proliferation, and the cell conducting the cellular activity is at least one of the cells in the group consisting of a monocyte, microglial cell, smooth muscle cell, and corneal epithelial cell.

All references, articles and patents cited herein are hereby incorporated herein in their entirety by reference.

Changes may be made in the various compositions, methods, components, kits, and assemblies described herein or in the steps or the sequence of steps of the methods described herein without departing from the spirit and scope of the presently disclosed and claimed inventive concept(s) as described herein.

REFERENCES

The following references, to the extent that they provide exemplary procedural or other details supplementary to those set forth herein, are specifically incorporated herein by reference.

1. Shafer W M, Martin L E, Spitznagel J K: Cationic antimicrobial proteins isolated from human neutrophil granulocytes in the presence of diisopropyl fluorophosphate. Infect Immun 1984, 45:29-35.
2. Pereira H A, Spitznagel J K, Pohl J, Wilson D E, Morgan J, Palings I, Larrick J W: CAP37, a 37 kD human neutrophil granule cationic protein shares homology with inflammatory proteinases. Life Sciences 1990, 46:189-196.
3. Pohl J, Pereira H A, Martin N M, Spitznagel J K: Amino acid sequence of CAP37, a human neutrophil granule-derived antibacterial and monocyte-specific chemotactic glycoprotein structurally similar to neutrophil elastase. FEBS Letters 1990, 272:200-204.
4. Shafer W M, Martin L E, Spitznagel J K: Late intraphagosomal hydrogen ion concentration favors the in vitro antimicrobial capacity of a 37-kilodalton cationic granule protein of human neutrophil granules. Infect Immun 1986, 53:651-655.
5. Brackett D J, Lerner M R, Lacquement M A, He R, Pereira H A: A synthetic lipopolysaccharide-binding peptide based on the neutrophil-derived protein CAP37 prevents endotoxin-induced responses in conscious rats. Infect Immun 1997, 65:2803-2811.
6. Pereira H A, Shafer W M, Pohl J, Martin L E, Spitznagel J K: CAP37, a human neutrophil-derived chemotactic factor with monocyte specific activity. J Clin Invest 1990, 85:1468-1476.
7. Ostergaard E, Flodgaard H: A neutrophil-derived proteolytic inactive elastase homologue (hHBP) mediates reversible contraction of fibroblasts and endothelial cell monolayers and stimulates monocyte survival and thrombospondin secretion. J Leukoc Biol 1992, 51:316-323.
8. Heinzelmann M, Mercer-Jones M A, Flodgaard H, Miller F N: Heparin-binding protein (CAP37) is internalized in monocytes and increases LPS-induced monocyte activation. J Immunol 1998, 160:5530-5536.
9. Rasmussen P B, Bjørn S, Hastrup S, Nielsen P F, Norris K, Thim L, Wiberg F C, Flodgaard H: Characterization of recombinant human HBP/CAP37/azurocidin, a pleiotropic mediator of inflammation-enhancing LPS-induced cytokine release from monocytes. FEBS letters 1996, 390: 109-112.
10. Heinzelmann M, Platz A, Flodgaard H, Polk Jr H C, Miller F N: Endocytosis of heparin-binding protein (CAP37) is essential for the enhancement of lipopolysaccharide-induced TNF-α production in human monocytes. J Immunol 1999, 162:4240-4245.
11. Pereira H A, Moore P, Grammas P: CAP37, a neutrophil granule-derived protein stimulates protein kinase C activity in endothelial cells. J Leukoc Biol 1996 a, 60:415-422.
12. Olofsson A M, Vestberg M, Herwald H, Rygaard J, David G, Arfors K-E, Linde V, Flodgaard H, Dedio J, Müller-Esterl W, Lundgren-Åkerlund E: Heparin-binding protein targeted to mitochondrial compartments protects endothelial cells from apoptosis. J Clin Invest 1999, 104:885-894.
13. Pereira H A, Kumar P, Grammas P: Expression of CAP37, a novel inflammatory mediator, in Alzheimer's disease. Neurobiol Aging 1996 b, 17:753-759.
14. Ross R: Atherosclerosis—an inflammatory disease. N Engl J Med 1999, 340:115-126.
15. Akiyama H, Barger S, Barnum S, Bradt B, Bauer J, Cole G M, Cooper N R, Eikelenboom P, Emmerling M, Fiebich B L, Finch C E, Frautschy S, Griffin W S T, Hampel H, Hull M, Landreth G, Lue L-F, Mrak R, Mackenzie I R, McGeer P L, O'Banion K, Pachter J, Pasinetti G, Plata-Salaman C, Rogers J, Rydel R, Shen Y, Streit W, Strohmeyer R, Tooyoma I, Van Muiswinkel F L, Veerhuis R, Walker D, Webster S, Wegrzyniak B, Wenk G, Wyss-Coray T: Inflammation and Alzheimer's disease. Neurobiol Aging 2000, 21:383-421.
16. Diglio C A, Grammas P, Giacomelli F, Wiener J: Angiogenesis in rat aorta ring explant cultures. Lab Invest 1989, 60:523-531.
17. Jaffe A E, Nachman R L, Becker C G, Minick C R: Culture of human endothelial cells derived from umbilical veins. J Clin Invest 1973, 52:2745-2756.
18. Gräbner R, Till U, Heller R: Flow cytometric determination of E-selectin, vascular cell adhesion molecule-1, and intercellular cell adhesion molecule-1 in formaldehyde-fixed endothelial monolayers. Cytometry 2000, 40:238-244.
19. Chomczynski P, Sacchi N: Single-step method of RNA isolation by acid guanidinium thiocyanate-phenol-chloroform extraction. Anal Biochem 1987, 162:156-159.
20. Corpet F: Multiple sequence alignment with hierarchical clustering. Nucl Acids Res 1988, 16:10881-10890.
21. Morgan J G, Sukiennicki T, Pereira H A, Spitznagel J K, Guerra M E, Larrick J W: Cloning of the cDNA for the serine protease homolog CAP37/Azurocidin, a microbicidal and chemotactic protein from human granulocytes. J Immunol 1991, 147:3210-3214.
22. Pereira H A, Erdem I, Pohl J, Spitznagel J K: Synthetic bactericidal peptide based on CAP37: a 37-kDa human neutrophil granule-associated cationic antimicrobial protein chemotactic for monocytes. Proc Natl Acad Sci (USA) 1993, 90:4733-4737.
23. Enk C D, Mahanty S, Blauvelt A, Katz S I: UVB induces IL-12 transcription in human keratinocytes in vivo and in vitro. Photochem Photobio 1996, 63:854-859.
24. Walter M J, Kajiwara N, Karanja P, Castro M, Holtzman M J: Interleukin 12 p40 production by barrier epithelial cells during airway inflammation. J Exp Med 2001, 193: 339-351.
25. Lonnemann G, Endres S, Van der Meer J W M, Cannon J G, Koch K M, Dinarello C A: Differences in the synthesis and kinetics of release of interleukin 1 alpha, interleukin 1 beta and tumor necrosis factor from human mononuclear cells. Eur J Immunol 1989, 19:1531-1536.

26. Sears P, Wong C-H: Enzyme action in glycoprotein synthesis. Cell Mol Life Sci 1998, 54:223-252.
27. Flodgaard H, Østergaard E, Bayne S, Svendsen A, Thomsen J, Engels M, Wollmer A: Covalent structure of two novel neutrophile leucocyte-derived proteins of porcine and human origin: neutrophil elastase homologues with strong monocyte and fibroblast chemotactic activities. Eur J Biochem 1991, 197:535-547.
28. Gautam N, Olofsson A M, Herwald H, Iversen L F, Lundgren-Akerlund E, Hedqvist P, Arfors K-E, Flodgaard H, Lindbom L: Heparin-binding protein (HBP/CAP37): A missing link in neutrophil-evoked alteration of vascular permeability. Nat Med 2001, 7:1123-1127.
29. Grammas P: A damaged microcirculation contributes to neuronal cell death in Alzheimer's disease. Neurobiol Aging 2000, 21:199-205.
30. Pereira H. A., Martin, L E, and Spitznagel, J K: Quantitation of a cationic antimicrobial granule protein of human polymorphonuclear leukocytes by ELISA. J. Immunol. Meth., 1989, 117:115-120.

What is claimed is:

1. An isolated monoclonal antibody or antigen-binding fragment thereof and/or a humanized form of the antibody/antigen-binding fragment thereof, wherein the monoclonal antibody is produced by the hybridoma D5F10, ATCC accession number PTA-122650, or the hybridoma B1B5, ATCC accession number PTA-122649.

2. The isolated monoclonal antibody or antigen-binding fragment thereof and/or a humanized form of the antibody/antigen-binding fragment thereof of claim 1, wherein the monoclonal antibody or antigen-binding fragment thereof is selected from the group consisting of a full length immunoglobulin molecule, an scFv, a Fab fragment, an Fab' fragment, an F(ab')2, an Fv, a disulfide linked Fv, and combinations thereof.

3. The isolated monoclonal antibody or antigen binding fragment thereof and/or a humanized form of the antibody/antigen-binding fragment thereof of claim 1, wherein the monoclonal antibody or antigen binding fragment thereof binds to the CAP37 epitope with a dissociation constant of less than or equal to about $10^{-7}$ M.

4. A pharmaceutical composition comprising the isolated monoclonal antibody or antigen-binding fragment thereof and/or a humanized form of the antibody/antigen-binding fragment thereof of claim 1, and a pharmaceutically acceptable carrier.

5. A hybridoma that produces the isolated monoclonal antibody or antigen binding fragment thereof and/or a humanized form of the antibody/antigen-binding fragment thereof of claim 1, wherein the hybridoma is D5F10, ATCC accession number PTA-122650, or the hybridoma is B1B5, ATCC accession number PTA-122649.

6. A method of diagnosing Alzheimer's disease in a subject, comprising:
    administering a labeled CAP37-specific antibody or labeled binding fragment thereof and/or a labeled humanized form of the antibody/antigen-binding fragment thereof to the subject, which is a monoclonal antibody produced by the hybridoma D5F10, ATCC accession number PTA-122650, or the hybridoma B1B5, ATCC accession number PTA-122649;
    imaging the brain of the subject to assess the brain for the presence of the labeled CAP37-specific antibody or labeled binding fragment thereof and/or a labeled humanized form of the antibody/antigen-binding fragment thereof in the cortical and hippocampal areas of the brain;
    detecting the presence of label in the cortical and/or hippocampal areas of the brain; and diagnosing the subject as having Alzheimer's disease when the presence of labeled CAP37-specific antibody or labeled binding fragment thereof and/or a labeled humanized form of the antibody/antigen-binding fragment thereof is detected in the cortical and/or hippocampal areas of the brain.

7. The method of claim 6, wherein the detected presence of the labeled CAP37-specific antibody or labeled binding fragment thereof and/or a labeled humanized form of the antibody/antigen-binding fragment thereof is made when the imaging technique detects at least two areas of labeled CAP37-specific antibody or labeled binding fragment thereof and/or a labeled humanized form of the antibody/antigen-binding fragment thereof in the cortical and/or hippocampal areas of the brain.

8. The method of claim 6, wherein a diagnosis of Alzheimer's disease is made for the subject when the brain is positive for both (1) the labeled CAP37-specific antibody or labeled binding fragment thereof and/or a labeled humanized form of the antibody/antigen-binding fragment thereof and (2) beta amyloid and/or tau protein.

9. A method of detecting Age-Related Macular Degeneration (AMD) in a subject suspected of having AMD, comprising:
    administering a labeled CAP37-specific antibody or labeled binding fragment thereof and/or a labeled humanized form of the antibody/antigen-binding fragment thereof to the subject, which is a monoclonal antibody produced by the hybridoma D5F10, ATCC accession number PTA-122650, or the hybridoma B1B5, ATCC accession number PTA-122649; and
    assessing at least one eye of the subject for the presence of the labeled CAP37-specific antibody or labeled binding fragment thereof and/or a labeled humanized form of the antibody/antigen-binding fragment thereof in the choroid, retinal pigment epithelium, and/or photoreceptor inner segment of the eye; and
    determining that the patient has AMD when presence of the labeled CAP37-specific antibody or labeled binding fragment thereof and/or a labeled humanized form of the antibody/antigen-binding fragment thereof is detected in the choroid, retinal pigment epithelium, and/or photoreceptor inner segment of the eye.

* * * * *

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial sequence
<220> FEATURE:
<223> OTHER INFORMATION: Completely synthesized

<400> SEQUENCE: 1
gtgctgggtg cctatgacct gagg                                          24

<210> SEQ ID NO 2
<211> LENGTH: 23
<212> TYPE: DNA
<213> ORGANISM: Artificial sequence
<220> FEATURE:
<223> OTHER INFORMATION: Completely synthesized

<400> SEQUENCE: 2
aagagcgcca ctcgggtgaa gaa                                           23

<210> SEQ ID NO 3
<211> LENGTH: 24
<212> TYPE: DNA
<213> ORGANISM: Artificial sequence
<220> FEATURE:
<223> OTHER INFORMATION: Completely synthesized

<400> SEQUENCE: 3
cagaatcaag gcaggcactt ctgc                                          24

<210> SEQ ID NO 4
<211> LENGTH: 24
<212> TYPE: DNA
<213> ORGANISM: Artificial sequence
<220> FEATURE:
<223> OTHER INFORMATION: Completely synthesized

<400> SEQUENCE: 4
gagaacacca tcgatccagt ctcg                                          24

<210> SEQ ID NO 5
<211> LENGTH: 24
<212> TYPE: DNA
<213> ORGANISM: Artificial sequence
<220> FEATURE:
<223> OTHER INFORMATION: Completely synthesized

<400> SEQUENCE: 5
ctgcagaggc agtggcagta tcgt                                          24

<210> SEQ ID NO 6
<211> LENGTH: 24
<212> TYPE: DNA
```

```
<213> ORGANISM: Artificial sequence
<220> FEATURE:
<223> OTHER INFORMATION: Completely synthesized

<400> SEQUENCE: 6
gcagaagtgc ctgccttgat tctg                                            24

<210> SEQ ID NO 7
<211> LENGTH: 24
<212> TYPE: DNA
<213> ORGANISM: Artificial sequence
<220> FEATURE:
<223> OTHER INFORMATION: Completely synthesized

<400> SEQUENCE: 7
cgagactgga tcgatggtgt tctc                                            24

<210> SEQ ID NO 8
<211> LENGTH: 199
<212> TYPE: PRT
<213> ORGANISM: Homo sapiens

<400> SEQUENCE: 8

Gln Asn Gln Gly Arg His Phe Cys Gly Gly Ala Leu Ile His Ala Arg
1               5                   10                  15

Phe Val Met Thr Ala Ala Ser Cys Phe Gln Ser Gln Asn Pro Gly Val
            20                  25                  30

Ser Thr Val Val Leu Gly Ala Tyr Asp Leu Arg Arg Arg Glu Arg Gln
        35                  40                  45

Ser Arg Gln Thr Phe Ser Ile Ser Ser Met Ser Glu Asn Gly Tyr Asp
    50                  55                  60

Pro Gln Gln Asn Leu Asn Asp Leu Met Leu Leu Gln Leu Asp Arg Glu
65                  70                  75                  80

Ala Asn Leu Thr Ser Ser Val Thr Ile Leu Pro Leu Pro Leu Gln Asn
                85                  90                  95

Ala Thr Val Glu Ala Gly Thr Arg Cys Gln Val Ala Gly Trp Gly Ser
            100                 105                 110

Gln Arg Ser Gly Gly Arg Leu Ser Arg Phe Pro Arg Phe Val Asn Val
        115                 120                 125

Thr Val Thr Pro Glu Asp Gln Cys Arg Pro Asn Asn Val Cys Thr Gly
    130                 135                 140

Val Leu Thr Arg Arg Gly Gly Ile Cys Asn Gly Asp Gly Gly Thr Pro
145                 150                 155                 160

Leu Val Cys Glu Gly Leu Ala His Gly Val Ala Ser Phe Ser Leu Gly
                165                 170                 175

Pro Cys Gly Arg Gly Pro Asp Phe Phe Thr Arg Val Ala Leu Phe Arg
            180                 185                 190

Asp Trp Ile Asp Gly Val Leu
        195

<210> SEQ ID NO 9
<211> LENGTH: 597
<212> TYPE: DNA
<213> ORGANISM: Homo sapiens

<400> SEQUENCE: 9
cagaatcaag gcaggcactt ctgcgggggt gccctgatcc atgcccgctt cgtgatgacc        60
gcggccagct gcttccaaag ccagaacccc ggggttagca ccgtggtgct gggtgcctat       120
```

```
gacctgaggc ggcgggagag gcagtcccgc cagacgtttt ccatcagcag catgagcgag    180
aatggctacg accccagca gaacctgaac gacctgatgc tgcttcagct ggaccgtgag    240
gccaacctca ccagcagcgt gacgatactg ccactgcctc tgcagaacgc cacggtggaa    300
gccggcacca gatgccaggt ggccggctgg gggagccagc gcagtggggg gcgtctctcc    360
cgttttccca ggtttgtcaa cgtgactgtg accccgagg accagtgtcg ccccaacaac     420
gtgtgcaccg gtgtgctcac ccgccgcggt ggcatctgca atggggacgg gggcacccc    480 ctcgtctgcg agggcctggc ccacggcgtg gcctcctttt ccctggggcc ctgtggccga   540
ggccctgact tcttcacccg agtggcgctc ttccgagact ggatcgatgg tgttctc       597
```